United States Patent
DeJohn et al.

(10) Patent No.: US 11,892,461 B1
(45) Date of Patent: Feb. 6, 2024

(54) PORTABLE DEVICES AND METHODS FOR ANALYZING SAMPLES

(71) Applicant: Biomeme, Inc., Philadelphia, PA (US)

(72) Inventors: Marc DeJohn, Philadelphia, PA (US); Christopher Cox, Philadelphia, PA (US); Thomas Welsh, Philadelphia, PA (US); Luke Gary, Philadelphia, PA (US); Alexia Quinn, Philadelphia, PA (US)

(73) Assignee: BIOMEME, INC., Philadelphia, PA (US)

( * ) Notice: Subject to any disclaimer, the term of this patent is extended or adjusted under 35 U.S.C. 154(b) by 0 days.

(21) Appl. No.: 18/184,806

(22) Filed: Mar. 16, 2023

Related U.S. Application Data

(63) Continuation of application No. PCT/US2021/050862, filed on Sep. 17, 2021.

(60) Provisional application No. 63/080,465, filed on Sep. 18, 2020.

(51) Int. Cl.
*G01N 35/00* (2006.01)
*G01N 35/02* (2006.01)

(52) U.S. Cl.
CPC ......... *G01N 35/0098* (2013.01); *G01N 35/02* (2013.01)

(58) Field of Classification Search
CPC .... G01N 35/0098; G01N 35/02; B01F 33/05; B01F 33/053
See application file for complete search history.

(56) References Cited

U.S. PATENT DOCUMENTS

| | | | |
|---|---|---|---|
| 3,757,780 | A | 9/1973 | Ishikawa |
| 5,151,192 | A | 9/1992 | Matkovich et al. |
| 5,529,391 | A | 6/1996 | Kindman et al. |
| 5,616,301 | A | 4/1997 | Moser et al. |
| 5,626,567 | A | 5/1997 | Gmeiner |
| 5,849,488 | A | 12/1998 | Alatossava et al. |
| 6,274,371 | B1 | 8/2001 | Colpan |
| 6,746,864 | B1 | 6/2004 | McNeil et al. |
| 7,167,755 | B2 | 1/2007 | Seeberger et al. |
| 7,759,112 | B2 | 7/2010 | Belgrader |
| 8,361,316 | B2 | 1/2013 | Siddiqi |
| 8,454,892 | B1 | 6/2013 | Rychwalski et al. |

(Continued)

FOREIGN PATENT DOCUMENTS

| | | |
|---|---|---|
| CN | 1680574 A | 10/2005 |
| CN | 1687391 A | 10/2005 |

(Continued)

OTHER PUBLICATIONS

Nov. 9, 2022 Notice of Allowance U.S. Appl. No. 17/479,391.

(Continued)

*Primary Examiner* — Jill A Warden
*Assistant Examiner* — John McGuirk
(74) *Attorney, Agent, or Firm* — Wilson Sonsini Goodrich & Rosati

(57) ABSTRACT

The present disclosure provides devices, systems, methods for processing and/or analyzing a biological sample. An analytic device for processing and/or analyzing a biological sample may comprise a moving carriage. The analytic device may be portable. The analytic device may receive instructions for performing an assay from a mobile electronic device external to a housing of the analytic device.

22 Claims, 39 Drawing Sheets

(56) References Cited

U.S. PATENT DOCUMENTS

| | | | |
|---|---|---|---|
| 8,633,032 | B2 | 1/2014 | Akashi et al. |
| 8,940,524 | B2 | 1/2015 | Cobb |
| 9,314,570 | B2 | 4/2016 | Kim |
| 9,535,676 | B1 | 1/2017 | Forehand et al. |
| 9,575,655 | B2 | 2/2017 | Rytivaara |
| 9,579,655 | B2 | 2/2017 | DeJohn et al. |
| 9,618,139 | B2 | 4/2017 | Handique |
| 9,926,553 | B2 | 3/2018 | De John et al. |
| 10,036,058 | B2 | 7/2018 | Baumgartner et al. |
| 10,457,983 | B2 | 10/2019 | DeJohn et al. |
| 10,724,032 | B2 | 7/2020 | DeJohn et al. |
| 11,299,728 | B2 | 4/2022 | DeJohn et al. |
| 2001/0003652 | A1 | 6/2001 | Freeman |
| 2001/0007062 | A1 | 7/2001 | Dumaresq-Lucas et al. |
| 2001/0012612 | A1 | 8/2001 | Petersen et al. |
| 2002/0150907 | A1 | 10/2002 | Fomovskaia et al. |
| 2004/0126279 | A1 | 7/2004 | Renzi et al. |
| 2004/0208796 | A1 | 10/2004 | Chiga |
| 2005/0033196 | A1 | 2/2005 | Alroy |
| 2006/0001870 | A1 | 1/2006 | Voigt et al. |
| 2006/0213827 | A1 | 9/2006 | Nozaki |
| 2006/0216206 | A1 | 9/2006 | Hudson et al. |
| 2006/0222567 | A1 | 10/2006 | Kloepfer et al. |
| 2007/0035732 | A1 | 2/2007 | Marsche et al. |
| 2007/0122809 | A1 | 5/2007 | Stevenson et al. |
| 2008/0145848 | A1 | 6/2008 | Stephan et al. |
| 2008/0254532 | A1 | 10/2008 | Chang et al. |
| 2009/0027998 | A1* | 1/2009 | Halaka .................. B03C 1/288 366/341 |
| 2009/0111193 | A1 | 4/2009 | Cooney et al. |
| 2009/0142333 | A1 | 6/2009 | Knopf et al. |
| 2009/0143233 | A1 | 6/2009 | Knight et al. |
| 2010/0177950 | A1 | 7/2010 | Donovan et al. |
| 2010/0204462 | A1 | 8/2010 | Walter et al. |
| 2011/0057117 | A1 | 3/2011 | Fawcett et al. |
| 2011/0076735 | A1 | 3/2011 | Jovanovich et al. |
| 2011/0201099 | A1 | 8/2011 | Anderson et al. |
| 2011/0290647 | A1 | 12/2011 | Feiglin |
| 2012/0077259 | A1 | 3/2012 | Cobb |
| 2012/0220024 | A1 | 8/2012 | Cobb |
| 2012/0288892 | A1 | 11/2012 | Maiyuran et al. |
| 2012/0288897 | A1 | 11/2012 | Ching et al. |
| 2013/0028814 | A1 | 1/2013 | Numai |
| 2013/0078619 | A1 | 3/2013 | Cooney et al. |
| 2013/0115607 | A1 | 5/2013 | Nielsen et al. |
| 2013/0230845 | A1 | 9/2013 | Egan et al. |
| 2014/0008311 | A1 | 1/2014 | Weston et al. |
| 2014/0206412 | A1 | 7/2014 | DeJohn et al. |
| 2015/0024436 | A1 | 1/2015 | Eberhart et al. |
| 2015/0111287 | A1 | 4/2015 | Rawle |
| 2015/0126724 | A1 | 5/2015 | De John et al. |
| 2016/0041095 | A1 | 2/2016 | Rothberg et al. |
| 2016/0069921 | A1 | 3/2016 | Holmes et al. |
| 2016/0115520 | A1 | 4/2016 | Krishnamurthy |
| 2016/0155120 | A1 | 6/2016 | Hurry |
| 2016/0169924 | A1 | 6/2016 | Torgerson et al. |
| 2016/0230210 | A1 | 8/2016 | Chen et al. |
| 2016/0231171 | A1 | 8/2016 | Assefa et al. |
| 2016/0265040 | A1 | 9/2016 | Baumgartner et al. |
| 2017/0066533 | A1 | 3/2017 | Long et al. |
| 2017/0068533 | A1 | 3/2017 | Kiaie et al. |
| 2017/0183713 | A1 | 6/2017 | DeJohn et al. |
| 2017/0327867 | A1 | 11/2017 | Dohale et al. |
| 2017/0333894 | A1 | 11/2017 | Khalid et al. |
| 2020/0158721 | A1* | 5/2020 | Ward .................. G01N 35/0098 |
| 2020/0276582 | A1 | 9/2020 | DeJohn et al. |
| 2020/0376494 | A1 | 12/2020 | DeJohn et al. |
| 2022/0074847 | A1 | 3/2022 | Eisenhower et al. |
| 2022/0186325 | A1 | 6/2022 | DeJohn et al. |
| 2022/0315916 | A1 | 10/2022 | DeJohn et al. |

FOREIGN PATENT DOCUMENTS

| | | |
|---|---|---|
| CN | 101722071 A | 6/2010 |
| CN | 101868721 A | 10/2010 |
| CN | 102348985 A | 2/2012 |
| CN | 102472695 A | 5/2012 |
| CN | 202379991 U | 8/2012 |
| CN | 104919035 A | 9/2015 |
| CN | 105092543 A | 11/2015 |
| EP | 0471721 B1 | 4/1995 |
| EP | 0781291 B1 | 12/2004 |
| EP | 1704922 A2 | 9/2006 |
| EP | 2174715 A1 | 4/2010 |
| EP | 2695629 A2 | 2/2014 |
| EP | 3063524 | 1/2020 |
| EP | 3685918 A1 | 7/2020 |
| GB | 2344526 A | 6/2000 |
| JP | 2013525763 A | 6/2013 |
| JP | 2016527510 A | 9/2016 |
| TW | 207958 B | 6/1993 |
| TW | 201144037 A | 12/2011 |
| WO | WO-2004045772 A2 | 6/2004 |
| WO | WO-2009036956 A1 | 3/2009 |
| WO | WO-2009047804 A2 | 4/2009 |
| WO | WO-2011106315 A1 | 9/2011 |
| WO | WO-2011106384 A1 | 9/2011 |
| WO | WO-2011130629 A1 | 10/2011 |
| WO | WO-2012138177 A2 | 10/2012 |
| WO | WO-2013010178 A1 | 1/2013 |
| WO | WO-2013052318 A1 | 4/2013 |
| WO | WO-2014100725 A1 | 6/2014 |
| WO | WO-2014113785 A1 | 7/2014 |
| WO | WO-2014188887 A1 | 11/2014 |
| WO | WO-2015015175 A1 | 2/2015 |
| WO | WO-2015054245 A1 | 4/2015 |
| WO | WO-2015066540 A1 | 5/2015 |
| WO | WO-2016124907 A1 | 8/2016 |
| WO | WO-2017112911 A1 | 6/2017 |
| WO | WO-2019055875 A2 | 3/2019 |
| WO | WO-2019118343 A2 | 6/2019 |
| WO | WO-2019143812 A1 | 7/2019 |
| WO | WO-2020191193 A1 | 9/2020 |
| WO | WO-2020257297 A1 | 12/2020 |
| WO | WO-2022061105 A1 | 3/2022 |

OTHER PUBLICATIONS

Dec. 17, 2021 Non-Final Office Action U.S. Appl. No. 16/817,733.
Feb. 1, 2023 Notice of Allowance U.S. Appl. No. 16/571,535.
Feb. 6, 2023 Final Office Action No. U.S. Appl. No. 16/899,810.
Mar. 29, 2022 Final Office Action U.S. Appl. No. 16/571,535.
Jun. 15, 2022 Non-Final Office Action U.S. Appl. No. 16/899,810.
Jun. 29, 2022 Non-Final Office Action U.S. Appl. No. 17/479,391.
Aug. 23, 2021 Non-Final Office Action U.S. Appl. No. 16/898,865.
Aug. 8, 2022 Final Office Action U.S. Appl. No. 16/817,733.
Sep. 15, 2021 Non-Final Office Action U.S. Appl. No. 16/571,535.
Sep. 30, 2022 Final Office Action U.S. Appl. No. 16/571,535.
Corrected Notice of Allowability dated Jun. 30, 2020 for U.S. Appl. No. 15/682,675.
European Examination Report dated Aug. 4, 2021, for EP Application No. 18888874.7.
European Examination Report dated Oct. 8, 2018, for EP Appl. 14740636.7.
European search report and search opinion dated Jun. 22, 2017 for EP Application No. EP14859198.5.
European search report with written opinion dated Aug. 22, 2016 for EP14740636.
Extended European Search Report dated Oct. 14, 2022 for EP20774341.0.
Extended European Search Report dated Apr. 28, 2020 for EP Application No. EP19216171.9.
Extended European Search Report dated Apr. 9, 2021 for EP Application No. EP18857231.
Extended European Search Report dated Jun. 7, 2022 for EP Application No. EP21210493.9.

(56) References Cited

OTHER PUBLICATIONS

International preliminary report on patentability and search report dated Dec. 3, 2015 for PCT Application No. PCT/US14/63552.
International Preliminary Report on Patentability dated Mar. 26, 2020 for PCT Application No. PCT/US2018/051228.
International Preliminary Report on Patentability dated Jul. 21, 2015 for International Application No. PCT/US2014/012308.
International Preliminary Report on Patentability dated Jul. 21, 2020 for International Application No. PCT/US2019/014005.
International Preliminary Report on Patentability dated Jun. 16, 2020 for International Application No. PCT/US2018/064736.
International Preliminary Report on Patentability for corresponding PCT Application No. PCT/US2020/023630 dated Sep. 30, 2021.
International Preliminary Report on Patentability for PCT/US2020/038159 dated Dec. 30, 2021.
International Search Report and Written Opinion dated Apr. 2, 2019 for PCT/US1851228.
International Search Report and Written Opinion dated May 23, 2019 for International Application No. PCT/US2019/014005.
International Search Report and Written Opinion for corresponding PCT Application No. PCT/US2020/023630 dated Jun. 16, 2020.
International Search Report and Written Opinion for PCT/US2020/038159 dated Oct. 14, 2020.
International Search Report and Written Opinion for PCT/US2021/050862 dated Dec. 30, 2021.
International Search Report dated Jan. 21, 2015 for PCT Application No. PCT/US14/63552.
International search report with written opinion dated May 23, 2014 for PCT/US2014/012308.
ISR/WO dated Apr. 19, 2019 for PCT/US18/064736.
Non-Final Office Action dated, Sep. 4, 19 for U.S. Appl. No. 15/682,675.
Notice of allowance dated Jan. 2, 2018 for U.S. Appl. No. 14/530,449.
Notice of allowance dated Jan. 17, 2017 for U.S. Appl. No. 14/159,844.
Notice of allowance dated Oct. 12, 2016 for U.S. Appl. No. 14/159,844.
Notice of allowance dated Dec. 8, 2021 for U.S. Appl. No. 16/898,865.
Notice of allowance dated Sep. 11, 2019 for U.S. Appl. No. 15/436,080.
Notice of allowance dated Sep. 27, 2019 for U.S. Appl. No. 15/436,080.
Notice of Allowance dated Jan. 30, 2018 for U.S. Appl. No. 14/530,449.
Notice of Allowance dated Mar. 18, 2020 for U.S. Appl. No. 15/682,675.
Office action dated Mar. 25, 2016 for U.S. Appl. No. 14/530,449.
Office action dated May 5, 2017 for U.S. Appl. No. 14/159,844.
Office action dated Jun. 20, 2017 for U.S. Appl. No. 14/530,449.
Office action dated Aug. 10, 2016 for U.S. Appl. No. 14/530,449.
Office action dated Nov. 5, 2015 for U.S. Appl. No. 14/159,844.
Office Action dated Jul. 27, 2016 issued in the corresponding Chinese Patent Application No. 201480010760.9.

\* cited by examiner

PORTABLE DEVICES AND METHODS FOR ANALYZING SAMPLES

CROSS-REFERENCE

This application is a continuation of International Application No, PCT/US2021/050862 filed Sep. 17, 2021, which claims the benefit of U.S. Provisional Patent Application No. 63/080,465, filed Sep. 18, 2020, each of which is entirely incorporated herein by reference.

STATEMENT REGARDING FEDERALLY SPONSORED RESEARCH OR DEVELOPMENT

This invention was made with government support under MCDC OTA No. W15QKN-16-9-1002, BASE AGREEMENT NO.: 714-111040-1 awarded by the U.S. Department of Defense. The government has certain rights in the invention.

BACKGROUND

Nucleic acid-based amplification reactions are now widely used in research and clinical laboratories for the detection of genetic and infectious diseases. However, the devices and systems used to perform these amplification reactions may be bulky. This may limit their portability and use in the field. Furthermore, the need to ship samples to a laboratory for analysis may result in contamination from handling, sample degradation, and delays in obtaining the results of the assay.

SUMMARY

Recognized herein is a need for portable analytic device for analyzing biological samples. The present disclosure provides a portable analytic device and methods for amplifying and/or detecting analytes from a sample in a substantially lab-free environment. The results of such an assay may be directed to a user, such as a subject, that may require such results. The user may then use the results of the assay for various purposes, including identifying a disease (e.g., an infectious disease or contamination).

In some aspects, the present disclosure provides a portable analytic device for processing a biological sample. In some embodiments, the portable analytic device comprises a housing. In some embodiments, the portable analytic device comprises at least one block within the housing. In some embodiments, the at least one block comprises a recess configured to contain an assay tube comprising the biological sample and a magnetic bead. In some embodiments, the portable analytic device comprises a bar within the housing. In some embodiments, the bar comprises a magnet. In some embodiments, the bar or the at least one block is configured to undergo motion such that the magnet and the assay tube move relative to one another, to thereby subject the magnetic bead to motion within the assay tube. In some embodiments, the portable analytic device has a weight of at most 15 kilograms. In some embodiments, the portable analytic device has a weight of at most 10 kilograms. In some embodiments, the portable analytic device has a weight of at most 5 kilograms. In some embodiments, the housing has a volume that is less than about 1,500 cubic centimeters. In some embodiments, the bar or the at least one block is configured to undergo linear motion. In some embodiments, the bar is configured to undergo linear motion. In some embodiments, the at least one block is configured to undergo linear motion. In some embodiments, the bar is configured to undergo motion. In some embodiments, the bar is configured to undergo motion while the at least one block is stationary. In some embodiments, the at least one block is configured to undergo motion. In some embodiments, the at least one block is configured to undergo motion while the bar is stationary. In some embodiments, the bar and the at least one block are configured to undergo motion. In some embodiments, the bar comprises a plurality of magnets, which plurality of magnets comprises said magnet. In some embodiments, the magnet is a permanent magnet. In some embodiments, the magnet is an electromagnet. In some embodiments, the portable analytic device further comprises at least one heating unit in thermal communication with the at least one block. In some embodiments, the at least one heating unit is configured to provide thermal energy to the assay tube through the at least one block. In some embodiments, the portable analytic device further comprises at least one cooling unit in thermal communication with the at least one block. In some embodiments, the cooling unit is configured to permit removal of thermal energy from the assay tube through the at least one block. In some embodiments, the cooling unit is configured to permit removal of the thermal energy using negative pressure that directs a fluid comprising at least a portion of the thermal energy away from the at least one block. In some embodiments, the portable analytic device further comprises an excitation filter and an emission filter. In some embodiments, the excitation filter and the emission filter are in optical communication with at least a portion of the recess. In some embodiments, the portable analytic device further comprises a movable carriage comprising an optical filter. In some embodiments, the movable carriage is configured to translate to bring the optical filter in optical communication with the excitation filter or the emission filter. In some embodiments, the movable carriage further comprises the bar comprising the magnet, and the movable carriage is configured to translate such that the magnet and the assay tube move relative to one another, to thereby subject the magnetic bead to motion within the assay tube. In some embodiments, the portable analytic device further comprises a power supply within the housing. In some embodiments, the power supply is configured to provide power to an actuator coupled to the bar or the at least one block, which actuator, upon receiving power from the power supply, is configured to subject the bar or the at least one block to motion such that the bar and the at least one block move relative to one another.

Another aspect of the present disclosure provides a method for processing a biological sample. In some embodiments, the method comprises providing a device. In some embodiments, the portable analytic device comprises a housing. In some embodiments, the portable analytic device comprises at least one block within the housing. In some embodiments, the at least one block comprises a recess that contains an assay tube comprising the biological sample and a magnetic bead. In some embodiments, the portable analytic device comprises a bar within the housing. In some embodiments, the bar comprises a magnet. In some embodiments, the method comprises subjecting the bar or the at least one block to motion such that the magnet and the assay tube move relative to one another, thereby subjecting the magnetic bead to motion within the assay tube. In some embodiments, the portable analytic device has a weight of at most 15 kilograms. In some embodiments, the portable analytic device has a weight of at most 10 kilograms, in some embodiments, the portable analytic device has a weight of at most 5 kilograms. In some embodiments, the housing has a volume that is less than about 1,500 cubic centimeters. In some embodiments, the bar or the at least one block is undergoes linear motion. In some embodiments, the bar undergoes linear motion. In some embodiments, the at least one block undergoes linear motion. In some embodiments, the bar undergoes motion. In some embodiments, the bar undergoes motion while the at least one block is stationary. In some embodiments, the at least one block undergoes motion. In some embodiments, the at least one block undergoes motion while the bar is stationary. In some embodiments, the bar and the at least one block undergo motion. In some embodiments, the bar comprises a plurality of magnets, which plurality of magnets comprises the magnet. In some embodiments, the magnet is a permanent magnet. In some embodiments, the magnet is an electromagnet. In some embodiments, the portable analytic device further comprises at least one heating unit in thermal communication with the at least one block. In some embodiments, the at least one heating unit provides thermal energy to the assay tube through the at least one block. In some embodiments, the portable analytic device further comprises at least one cooling unit in thermal communication with the at least one block. In some embodiments, the cooling unit permits removal of thermal energy from the assay tube through the at least one block. In some embodiments, the cooling unit permits removal of the thermal energy using negative pressure that directs a fluid comprising at least a portion of the thermal energy away from the at least one block. In some embodiments, the portable analytic device further comprises an excitation filter and an emission filter. In some embodiments, the excitation filter and the emission filter are in optical communication with at least a portion of the recess. In some embodiments, the portable analytic device further comprises a movable carriage comprising an optical filter. In some embodiments, the movable carriage translates to bring the optical filter in optical communication with the excitation filter or the emission filter. In some embodiments, the movable carriage further comprises the bar comprising the magnet, and the movable carriage is translates such that the magnet and the assay tube move relative to one another, to thereby subject the magnetic bead to motion within the assay tube. In some embodiments, the portable analytic device further comprises a power supply within the housing. In some embodiments, the power supply provides power to an actuator coupled to the bar or the at least one block, which actuator, upon receiving power from the power supply, subjects the bar or the at least one block to motion such that the bar and the at least one block move relative to one another. In some embodiments, the portable analytic device further comprises a processing unit comprising a circuit within the housing, wherein the processing unit communicates with a mobile electronic device external to the housing. In some embodiments, the method further comprises (a) receiving by the processing unit instructions from the mobile electronic device external to the housing for processing the biological sample in the assay tube; and (b) in response to the instructions, directing the at least one heating unit to provide thermal energy to the at least one block to provide heat to the biological sample within the assay tube. In some embodiments, the method further comprises, in response to the instructions, directing a cooling unit to remove thermal energy from the assay tube through the at least one block. In some embodiments, the method further comprises detecting a signal from the biological sample. In some embodiments, the method does not cause signal drift of the signal.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides devices, systems, and methods for sample processing and/or analysis. An analytic device may be portable and may comprise a housing, a block heated by a heating unit that is configured to provide thermal energy to a sample container including a sample, and a light path to provide excitation energy from an excitation source to the sample. An analytic device may be configured to accept and/or communicate with a mobile electronic device. An analytic device may also comprise a movable carriage that comprises an optical filter and an excitation source and is configured to translate to bring the optical filter in alignment with the light path. The inclusion of a movable carriage may facilitate the production of a smaller and/or less expensive analytic device as one or more excitation sources, optical filters, and light paths of the movable carriage may be used to process and/or analyze multiple sample containers including multiple samples. An analytic device may be used to analyze a biological sample including, or suspected of including, one or more nucleic acid molecules to determine the presence or an amount of the one or more nucleic acid molecules.

Analytic Device

Figure 1A:
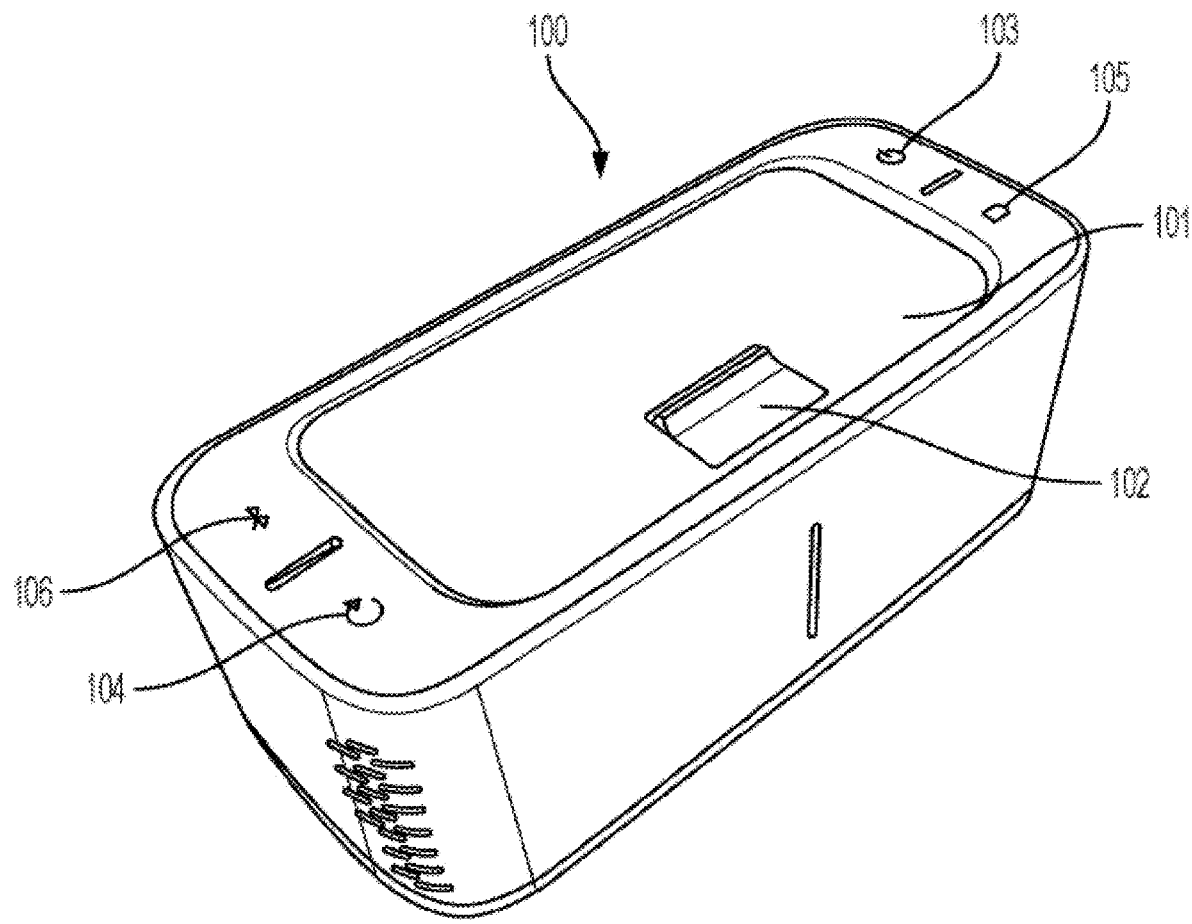
FIGS. 1A-1B show various views of a housing for a portable analytic device for analyzing a biological sample.
Figure 1B:
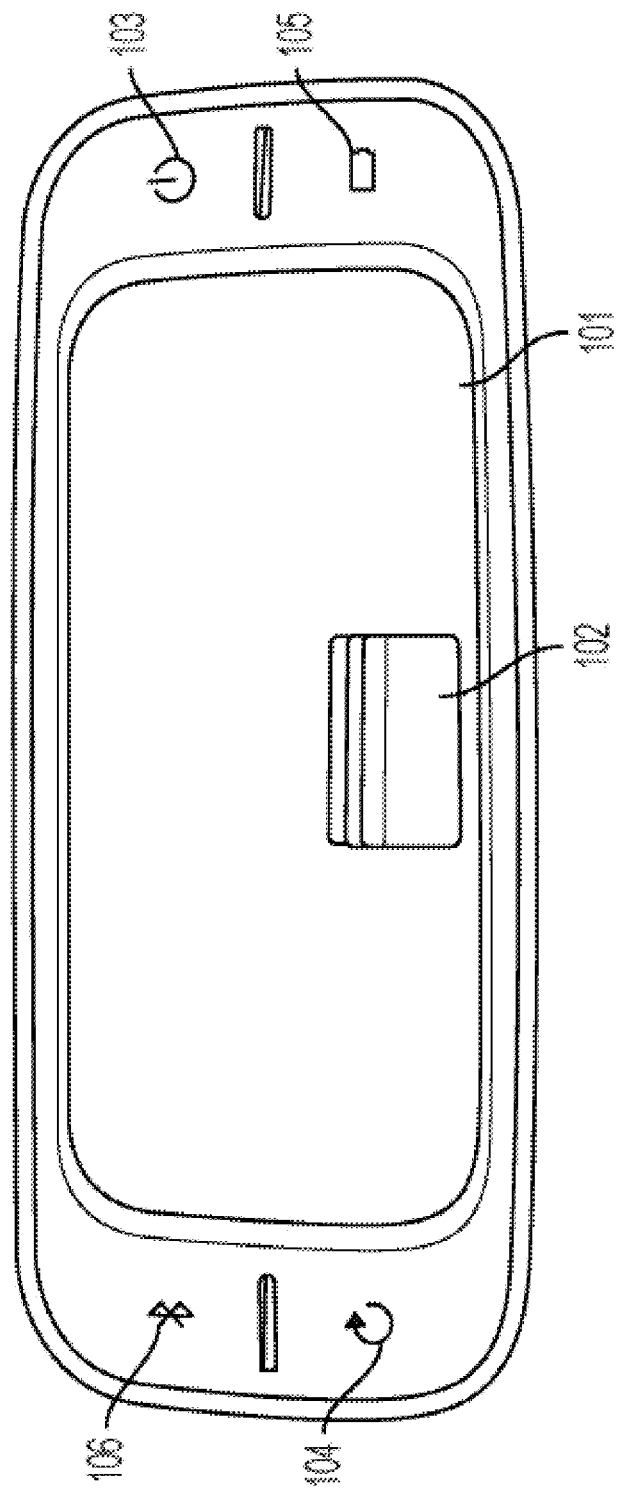

An analytic device of the present disclosure may be used for processing and/or analyzing a sample, such as a biological sample. An analytic device of the present disclosure may be portable. For example, an analytic device may be handheld. FIGS. 1A-1B show (A) perspective and (B) side views of a housing 100 for a portable analytic device for analyzing a biological sample. A housing may have a lid 101, a securing unit 102 for securing the lid in an open or closed position, and/or buttons or indicators 103406. Housing 100 may comprise a button 103 for powering on/off the portable analytic device. Housing 100 may comprise a button 104 for restarting the portable analytic device. Housing 100 may comprise an indicator 105 for notifying a user that the battery is low and/or an indicator 106 that a wireless connection (e.g., a Bluetooth or Near Field Communication connection) has been established between the analytic device and a mobile electronic device.

An analytic device may comprise at least one button capable of, upon actuation, affecting the operability of the analytic device (e.g., powering on/off the portable analytic device or connecting the analytic device to other devices). An analytic device may comprise 1, 2, 3, 4, 5, or more buttons. For example, an analytic device may comprise 4 buttons. Each button may correspond to a different function or feature of the analytic device. In some cases, pairs of buttons may correspond to the same function or feature of the analytic device. For example, an analytic device may include a button to increase a value, zoom level, volume, or other characteristic as well as a button to decrease the same value, zoom level, volume, or other characteristic.

A button mechanism may be a physical mechanism. For example, a button may comprise a depressible mechanism, such as button or micro-switch. Alternatively, a button may comprise a slidable or rotatable mechanism. For analytic devices including two or more buttons, each button may be separately selected from the group consisting of depressible mechanisms, slidable mechanisms, and rotatable mechanisms.

A button may comprise a touch-sensitive feature or mechanism. For example, buttons 103 and 104 of FIGS. 1A and 1B may comprise a touch-sensitive feature or mechanism. A touch-sensitive mechanism may be a touch-sensitive virtual mechanism (e.g., a virtual button). Such a virtual mechanism may be virtually depressible, virtually slidable, or virtually rotatable, thereby giving the illusion of a physical button. For example, the analytic device may comprise or be configured to accept a mobile electronic device communicatively coupled with a wireless connection to the analytic device, and the mobile electronic device may comprise one or more virtual buttons. Depression of a virtual button of the mobile electronic device may transmit a signal from the mobile electronic device to the analytic device, thereby affecting, e.g., a thermocycling program or other process, as described herein. A connection between an analytic device and a mobile electronic device may comprise a one-way or two-way wired or wireless connection, such as a WiFi connection, a Bluetooth connection, a Bluetooth LE connection, an ANT+connection, or a Gazell connection.

An analytic device may comprise one or more buttons disposed anywhere on the external surface of a housing of the analytic device. For example, a button may be located on a front face, a back face, a right side, a left side, a top side, or a bottom side of a housing of an analytic device. A button may be disposed in a location that is unavailable or hidden during operation of an analytic device (e.g., on the bottom side of a housing of the analytic device). In some cases, a panel may be used to cover or hide one or more buttons (e.g., when the analytic device is not in use and/or to prevent accidental actuation of a button).

Actuation or activation of one or more buttons may permit the user to cycle between a plurality of different thermocycling programs. For example, actuation of a button may cause an analytic device to switch from executing a first thermocycling program to a second thermocycling program. In another example, actuation of a button may cause an analytic device to switch from an "off" state to executing a first thermocycling program. Actuation of the button a second time may cause the analytic device to switch from executing a first thermocycling program to an "off" state. It should appreciated that an "off" state may refer to an idle state (e.g., wherein an analytic device may be on but a thermocycling program is paused, or wherein the analytic device is in a minimal power state) or a powered-down state (e.g., wherein the analytic device is powered off). Actuation of a button may affect a parameter of a thermocycling program. For example, an analytic device may comprise a depressible mechanism, and actuation of the depressible mechanism may cause a thermocycling program to switch from a denaturation step to an annealing step. In another example, an analytic device may comprise a rotatable mechanism, and rotation of the rotatable mechanism may cause a thermocycling temperature to increase. In some cases, actuation of two or more buttons may be required to affect a thermocycling program.

The degree of an input may affect the state of a thermocycling program. Non-limiting examples of a degree of an input that may be varied include a number of inputs (e.g., a number of times a button is actuated and released in succession), a speed of an input (e.g., a speed at which a button is actuated and/or released), a duration of an input (e.g., an amount of time that a button is actuated), a force exerted for the input (e.g., a force with which a button is actuated), and a direction of an input. An input may comprise actuation of a button. In one example, an analytic device may comprise a depressible mechanism, and brief (e.g., less than half of one second) depression and subsequent release of the depressible mechanism may pause a thermocycling program. In another example, a paused thermocycling program may be resumed by depressing a depressible mechanism for, e.g., 1-2 seconds.

An analytic device may be configured to accept one or more containers including a sample. For example, an analytic device may be configured to accept one or more assay tubes. An assay tube for use with an analytic device of the present disclosure may have any useful size and shape and comprise any useful material. For example, an assay tube may comprise a plastic, a polymer, or glass. An analytic device may be configured to accept an assay tube having a cross section that is substantially cylindrical, substantially rectangular, or has any other shape (e.g., a star shape). An analytic device may be configured to accept an assay tube having a mechanical key element such as a groove or protrusion disposed at one end of the assay tube or along a dimension of the assay tube to facilitate placement of the assay tube in the analytic device. For example, an assay tube may comprise a substantially rectangular protrusion along its length and the analytic device may comprise a corresponding indentation configured to accept the assay tube in a particular orientation. An analytic device may be configured to accept an assay tube having a cap or lid. Alternatively, an analytic device may comprise a component configured to cover an opening of an assay tube when the assay tube is placed in the analytic device. An analytic device may be configured to accept one or more assay tubes. For example, an analytic device may be configured to accept 1, 2, 3, 4, 5, 6, 7, 8, 9, or more assay tubes.

A device described herein can have a surface or support to receive a reagent tube or a cartridge. The cartridge can be a reagent cartridge. The surface or support can be a recessed surface or support. The surface can be a protruded surface or support. The surface can be a chamber. The cartridge can be loaded onto the surface or support. Upon loading the cartridge onto the surface or support, a lid can be closed to click the cartridge in place.

Figure 1C:
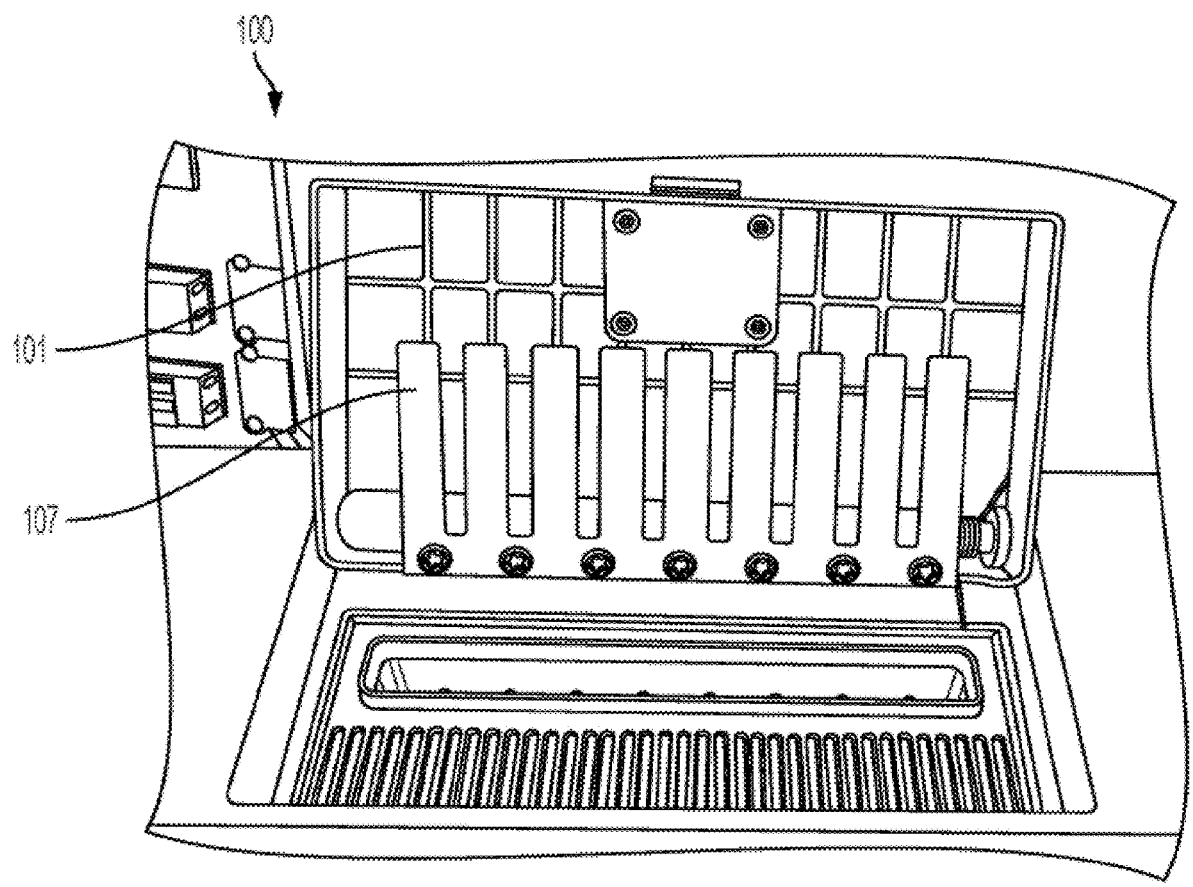
FIG. 1C shows a lid of a housing for a portable analytic device, the lid having a bendable comb capable of applying pressure and/or heat to an assay tube inserted into the analytic device.
Figure 1D:
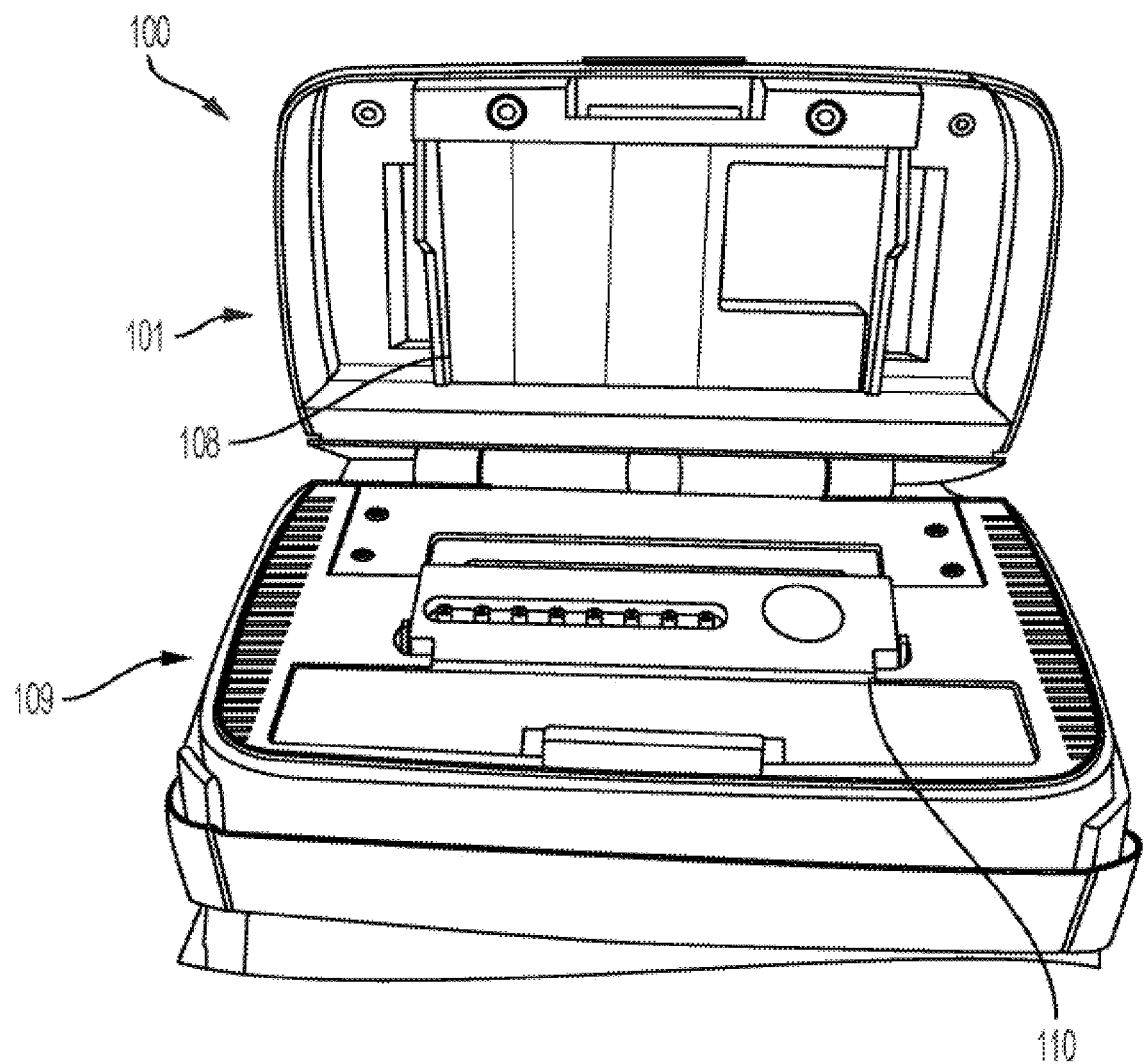
FIG. 1D shows an example of a housing for a portable analytic device with the lid open.

As shown in FIG. 1C, an inner surface of a lid 101 of housing 100 of the analytic device may comprise one or more cantilevers 107 capable of applying pressure to one or more assay tubes seated in a block of the analytic device. A cantilever may be useful for securing an assay tube containing a sample against the block, thereby increasing the efficiency of energy transfer between the block and the assay tube. A cantilever may be heated (e.g., at a temperature equal to the temperature of the block) to effect heating of a portion of the assay tube not in contact with the block. A cantilever may be heated to any temperature, and the temperature of the cantilever may change throughout a thermal cycle. For example, the temperature of a cantilever may be coordinated (e.g., to be the same as) the temperature of the block throughout a thermal cycle. As shown in FIG. 1D, an inner surface of a lid 101 of housing 100 of the analytic device may comprise a recessed surface 108 to receive or accommodate a cartridge inserted into the portable analytic device. An inner surface of the body 109 of housing 100 of the analytic device may comprise a protruded surface 110 to receive a cartridge inserted into the portable analytic device.

An analytic device may be portable. For example, an analytic device including a housing may be able to be easily carried or moved. A size, weight and/or shape of the housing and/or other components may affect the portability of the analytic device. A volume of a housing of an analytic device may be less than about 100,000 cubic centimeters, less than about 50,000 cubic centimeters, less than about 10,000 cubic centimeters, less than about 9,000 cubic centimeters, less than about 8,000 cubic centimeters, less than about 7,000 cubic centimeters, less than about 6,000 cubic centimeters, less than about 5,000 cubic centimeters, less than about 4,500 cubic centimeters, less than about 4,000 cubic centimeters, less than about 3,500 cubic centimeters, less than about 3,000 cubic centimeters, less than about 2,500 cubic centimeters, less than about 2,000 cubic centimeters, less than about 1,500 cubic centimeters, less than about 1,400 cubic centimeters, less than about 1,300 cubic centimeters, less than about 1,200 cubic centimeters, less than about 1,100 cubic centimeters, less than about 1,000 cubic centimeters, less than about 900 cubic centimeters, less than about 800 cubic centimeters, less than about 700 cubic centimeters, less than about 600 cubic centimeters, or less than about 500 cubic centimeters. For example, a volume of a housing of an analytic device may be less than about 1,500 cubic centimeters. A volume of a housing of an analytic device may fall within a range. For example, a volume of a housing of an analytic device may be between about 500 cubic centimeters and about 1,500 cubic centimeters. A dimension of the housing (e.g., length, width or height) may be at most about 50 centimeters, at most about 40 centimeters, at most about 30 centimeters, at most about 25 centimeters, at most about 24 centimeters, at most about 23 centimeters, at most about 22 centimeters, at most about 21 centimeters, at most about 20 centimeters, at most about 19 centimeters, at most about 18 centimeters, at most about 17 centimeters, at most about 16 centimeters, at most about 15 centimeters, at most about 14 centimeters, at most about 13 centimeters, at most about 12 centimeters, at most about 11 centimeters, at most about 10 centimeters, at most about 9 centimeters, at most about 8 centimeters, at most about 7 centimeters, at most about 6 centimeters, or at most about 5 centimeters.

A weight of an analytic device including the housing may be less than about 25 kilograms, less than about 20 kilograms, less than about 15 kilograms, less than about 10 kilograms, less than about 5 kilograms, less than about 4.5 kilograms, less than about 4 kilograms, less than about 3.5 kilograms, less than about 3 kilograms, less than about 2.5 kilograms, less than about 2.4 kilograms, less than about 2.3 kilograms, less than about 2.2 kilograms, less than about 2.1 kilograms, less than about 2 kilograms, less than about 1.9 kilograms, less than about 1.8 kilograms, less than about 1.7 kilograms, less than about 1.6 kilograms, less than about 1.5 kilograms, less than about 1.4 kilograms, less than about 1.3 kilograms, less than about 1.2 kilograms, less than about 1.1 kilograms, less than about 1 kilogram, less than about 0.9 kilograms, less than about 0.8 kilograms, less than about 0.7 kilograms, less than about 0.6 kilograms, less than about 0.5 kilograms, less than about 0.4 kilograms, less than about 0.3 kilograms, less than about 0.2 kilograms, or less than about 0.1 kilograms. For example, a volume of a housing of an analytic device may be less than about 1.5 kilograms. A weight of an analytic device including a housing may fall within a range of weights. For example, a weight of an analytic device including a housing may be between about 0.5 kilograms and about 1.5 kilograms.

A shape of a housing of an analytic device may also contribute to the portability of the analytic device. At least one dimension of a housing (e.g., length, width or height), may be sufficiently small such that the housing may be easily grasped by the human hand. An analytic device may have an ergonomically shaped housing of a size that enables a user to hold the analytic device with one or two hands. The housing may comprise a gripping region, e.g., a portion of the housing that is pipped by the user when the user holds the analytic device. A gripping region of a housing may be shaped to conform to the fingers of the user, thereby allowing the user to maintain a secure grip on the housing. A front surface of a housing of an analytic device may be narrower in a middle section associated with a gripping region than at a top or bottom section of the front surface. The narrower section may be conveniently and securely gripped by the user, while the relatively wider top section may include a display device or a component thereof, such as a screen. A housing may comprise a retractable handle that may be ergonomically shaped. A housing of an analytic device may feature rounded corners and/or edges (e.g., where perpendicular surfaces meet) such that when a user holds the analytic device, the user's hand may be in contact with rounded corners rather than sharp corners.

Figure 9:
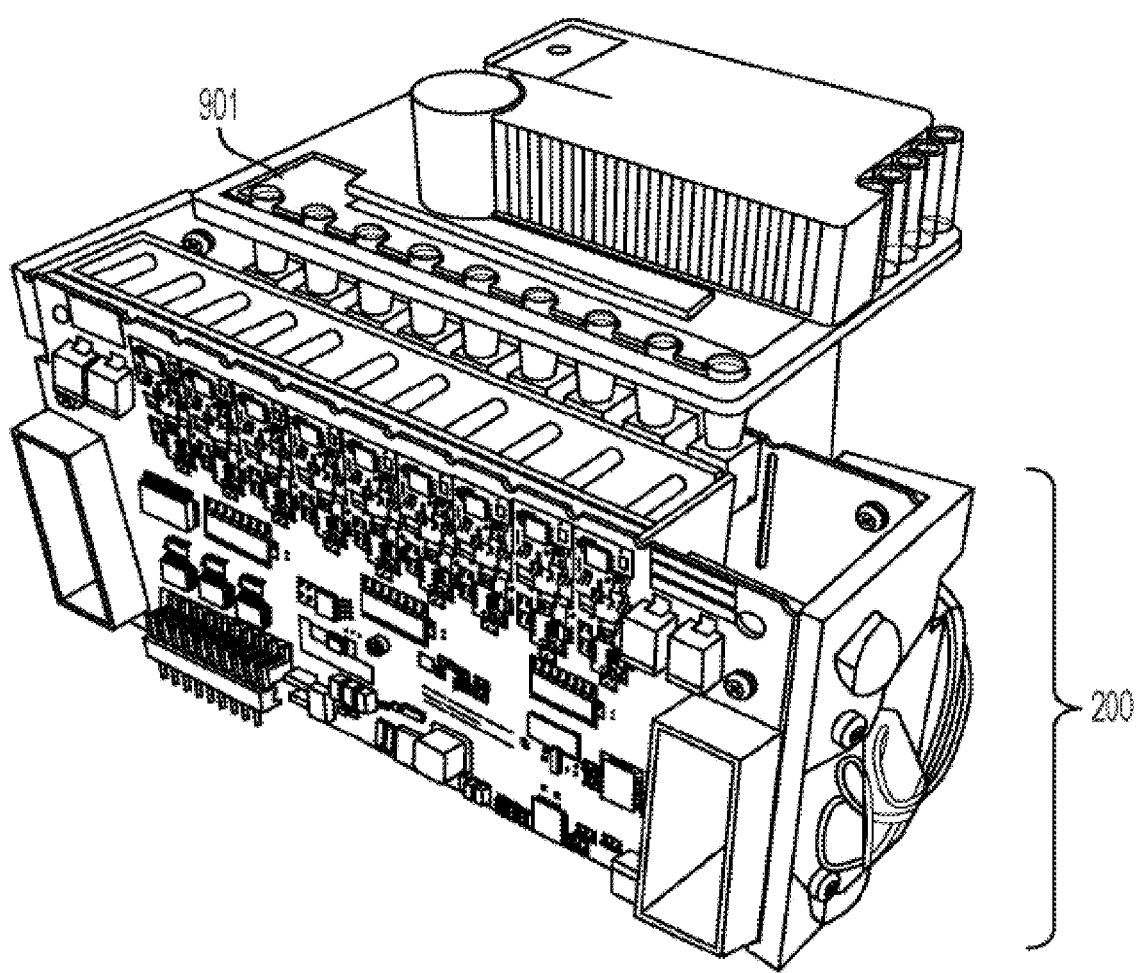
FIG. 9 shows an example portable analytic device having multiple blocks, and assay tubes inserted into the blocks.
Figure 13:
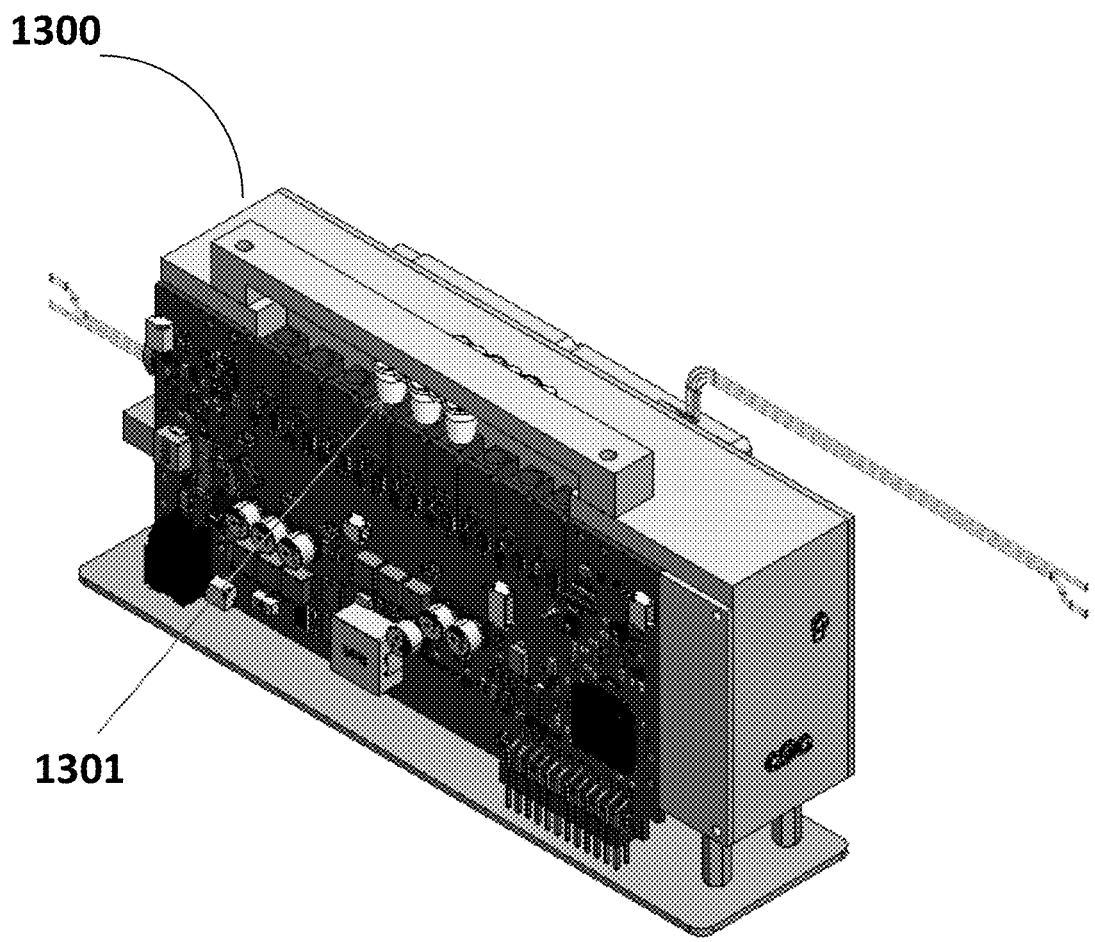
FIG. 13 shows an example portable analytic device having multiple blocks, and assay tubes inserted into the blocks.

FIG. 9 shows an example portable analytic device having a sample cartridge 901 inserted into the portable analytic device for sample analysis. A perspective view of an internal mechanism 200 is shown. FIG. 13 shows another example of the portable analytic device 1300 having sample tubes 1301 inserted into the portable analytic device for sample analysis.

Thermocycling

Figure 2:
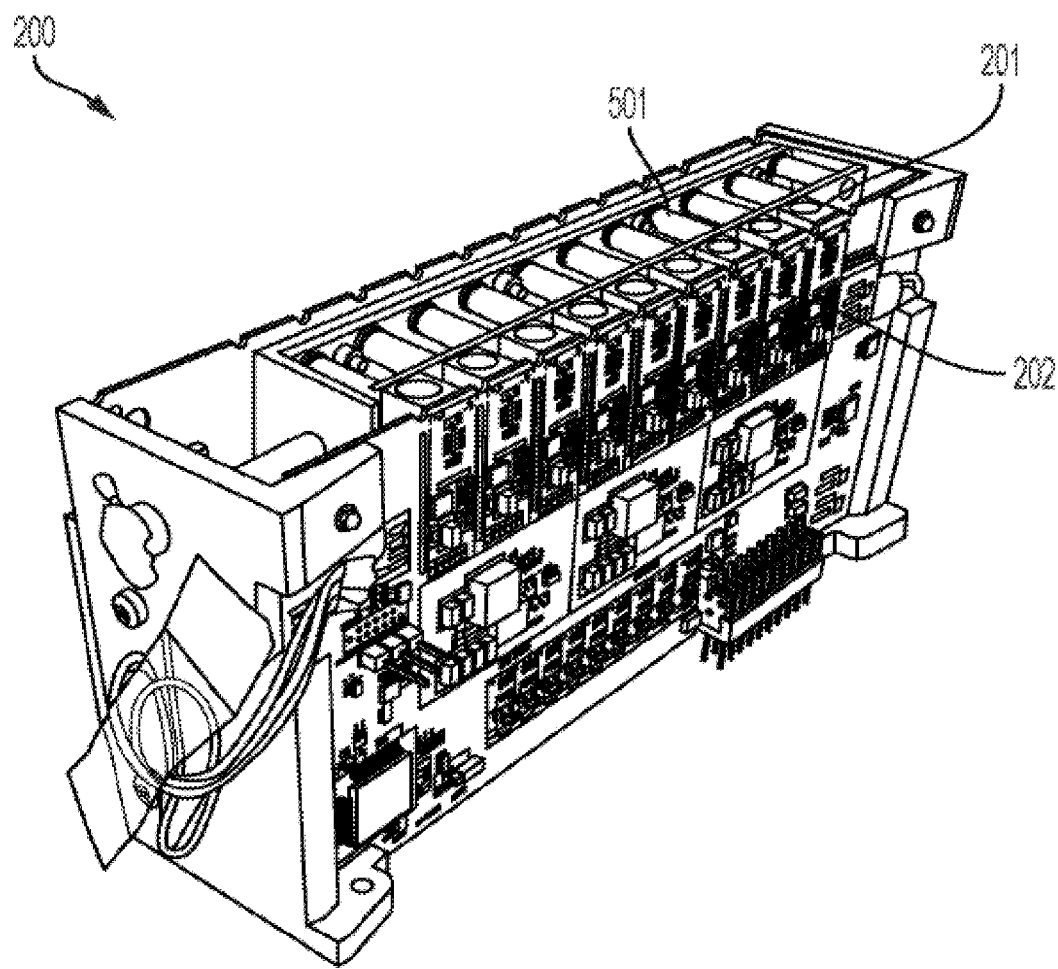
FIG. 2 shows a perspective view of an internal mechanism for a portable analytic device for analyzing a biological sample.

An analytic device may be configured to heat or cool a sample within an assay tube. As shown in FIG. 2, an analytic device 200 may comprise one or more blocks 201 within which an assay tube containing a sample is placed. The analytic device may be configured to raise or lower the temperature of the block using a heater 202 (e.g., a resistive heater) in discrete steps.

In some cases, the block can convert electrical energy into heat through the process of resistive or joule heating. The block can be a resistive heater. Heated blocks can have power resister (e.g., thermistor), thermal epoxy to bring in thermal communication with sample chambers. The blocks may be level and uniform. Cooling of the block can be achieved or controlled through a fan.

In some cases, the block can be a Peltier heater. Heating and cooling can be achieved or controlled through a Peltier controller. In some other cases, the block may not be a Peltier heater or the block may not be controlled by a Peltier controller.

The portable analytic device described herein may or may not comprise a heated lid.

Figure 3A:
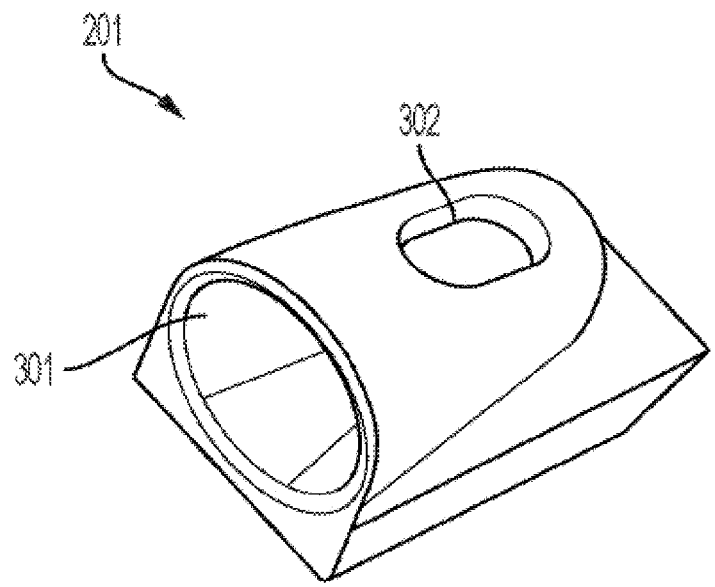
FIGS. 3A-3B show various blocks for use in a portable analytic device.
Figure 3B:
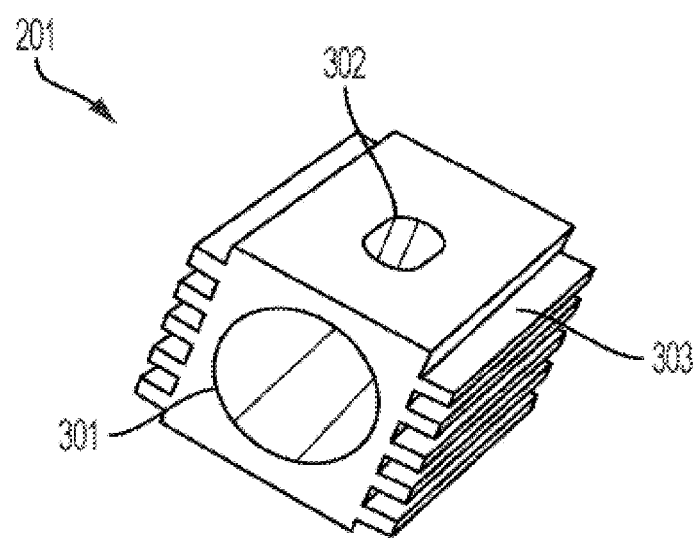

A block 201 may comprise any useful material. Non-limiting examples of materials that may be used to construct a block include aluminum, concrete, glass, quartz, steel, iron, nickel, zinc, copper, brass, silver, tin, gold, carbon, and any combination thereof (e.g., a zinc alloy such as Zamak). For example, a block may be constructed using silver, as shown in FIG. 3A, in another example, a block may be constructed using aluminum, as shown in FIG. 3B. The block may include a first opening 301 for accepting a vial containing or configured to contain a sample (e.g., biological sample), and a second opening 302 configured to be in optical communication with a detector or an optical source (e.g., for excitation). The block may include a third opening (not shown) configured to be in optical communication with a detector or an optical source. For example, the second opening 302 may be in optical communication with a detector and the third opening (not shown) may be in optical communication with an optical source for excitation. The block may comprise one or more fins 303.

A block may be formed of an alloy. For example, a block may be constructed using steel. It is contemplated that constructing the block using a material compatible with the process of die casting, (e.g., a material that that may be used in the die cast construction of a block) can allow for the blocks to be manufactured at a larger scale (e.g., at a higher volume in a shorter period of time, and/or at a reduced cost per unit). In some embodiments, a block can be constructed using a combination of materials. For example, a block can be constructed using aluminum and subsequently coated with nickel. In another example, a block can be constructed using zinc, and coated with silver. Coating the block can be advantageous for several reasons. For example, coating a block (e.g., with nickel) can allow the block to be soldered to a printed circuit board (PCB), as opposed to using thermal epoxy. Soldering the block to the PCB can allow an analytic device to be manufactured with a removable block (e.g., in the case of damage), whereas the use of a thermal epoxy can permanently affix the block to the PCB. It is contemplated that the choice of the material used to produce the block may affect the number of thermal cycles that the analytic device is capable of undergoing using a power supply (e.g., a self-contained power supply, such as a battery). In particular, the higher the specific heat capacity of the material, the more energy may be required to raise the temperature of the material. Accordingly, a block can be constructed using a material with a specific heat capacity (e.g., at 25° C., as measured in Joules per gram per ° C.; J/g° C.) of less than about 2 J/g° C., less than about 1.5 J/g° C., less than about 1 J/g° C., less than about 0.9 J/g° C., less than about 0.8 J/g° C., less than about 0.7 J/g° C., less than about 0.6 J/g° C., less than about 0.5 J/goC, less than about 0.45 J/g° C., less than about 0.4 J/g° C., less than about 0.35 J/g*C, less than about 0.3 J/g° C., less than about 0.25 J/g° C., less than about 0.2 J/g° C., less than about 0.15 J/g° C., less than about 0.1 J/g° C., less than about 0.05 J/g° C., or less than about 0.01 J/g° C. For example, a block can be constructed using a material having a specific heat capacity of less than about 1 J/g° C. at 25° C.

Additionally, the lower the thermal conductivity of a material, the more energy may be required to raise the temperature of the material. Accordingly, a block can be constructed using a material with a thermal conductivity (e.g., as measured in Watt per meter per Kelvin; W/mK) of at least about 500 W/mK, at least about 400 W/mK, at least about 300 W/mK, at least about 200 W/mK, at least about 175 W/mK, at least about 150 W/mK, at least about 125 W/mK, at least about 100 W/mK, at least about 75 W/mK, at least about 50 W/mK, at least about 25 W/mK, or at least about 10 W/mK. For example, a block can be constructed using a material having a thermal conductivity of at least about 75 W/mK. In another example, a block can be constructed using a material having a thermal conductivity of at least about 400 W/mK.

A block may also comprise one or more fins 303 to increase a surface area of the block and provide better heat dissipation from the block. It is also contemplated that the volume of the material used to form a block may affect the number of thermal cycles that the analytic device is capable of undergoing using a power supply (e.g., a self-contained power supply, such as a battery). In particular, the greater the volume of the material used to construct the block, the more energy may be required to raise the temperature of the block. Accordingly, a volume of a material used to construct a block may be less than about 20 cubic centimeters, less than about 15 cubic centimeters, less than about 10 cubic centimeters, less than about 9 cubic centimeters, less than about 8 cubic centimeters, less than about 7 cubic centimeters, less than about 6 cubic centimeters, less than about 5 cubic centimeters, less than about 4 cubic centimeters, less than about 3 cubic centimeters, less than about 2 cubic centimeters, less than about 1 cubic centimeters, less than about 0.9 cubic centimeters, less than about 0.8 cubic centimeters, less than about 0.7 cubic centimeters, less than about 0.6 cubic centimeters, less than about 0.5 cubic centimeters, less than about 0.4 cubic centimeters, less than about 0.3 cubic centimeters, less than about 0.2 cubic centimeters, or less than about 0.1 cubic centimeters. For example, a volume of a material used to construct a block may be less than about 0.5 cubic centimeters.

As described above, the material and/or volume of material used to construct the heating may be selected based on minimizing the energy required to heat or cool the block. Accordingly, an analytic device of the present disclosure may provide more energy to perform a greater number of thermal cycles, as compared to a device that uses a larger block, or a block constructed using a material with a higher specific heat capacity. An analytic device of the present disclosure may perform any number of thermal cycles. An analytic device may perform a given number of thermal cycles on a single charge of a power supply (e.g., a self-contained power supply, such as a battery). An analytic device of the present disclosure may perform at least about 1 thermal cycle, at least about 2 thermal cycles, at least about 3 thermal cycles, at least about 4 thermal cycles, at least about 5 thermal cycles, at least about 6 thermal cycles, at least about 7 thermal cycles at least about 8 thermal cycles, at least about 9 thermal cycles, at least about 10 thermal cycles, at least about 11 thermal cycles, at least about 12 thermal cycle, at least about 13 thermal cycles, at least about 14 thermal cycles, at least about 15 thermal cycles, at least about 16 thermal cycles, at least about 17 thermal cycles, at least about 18 thermal cycles at least about 19 thermal cycles, at least about 20 thermal cycles, at least about 25 thermal cycles, at least about 30 thermal cycles, at least about 35 thermal cycle, at least about 40 thermal cycles, at least about 45 thermal cycles, at least about 50 thermal cycles, or at least about 100 thermal cycles. An analytic device of the present disclosure may perform about 1 to about 10 thermal cycles, about 5 to about 15 thermal cycles, about 10 to about 20 thermal cycles, or about 15 to about 25 thermal cycles.

An analytic device of the present disclosure may be configured to perform an amplification reaction such as polymerase chain reaction (PCR)(e.g., by cycling the temperature of a sample in an assay tube). Performing PCR may involve making a series of repeated temperature changes (e.g., thermal cycles) with each series (e.g., cycle) including two or three discrete temperature steps. Thermal cycling may be preceded by a single temperature step at a higher temperature (e.g., >90° C.). Temperatures used and the length of time they are applied in each cycle may vary based on, for example, the enzyme used for deoxyribonucleic acid (DNA) synthesis, the concentration of bivalent ions and nucleotides (dNTPs) in the reaction, and the melting temperature (Tm) of one or more primers. The individual steps of an amplification reaction such as PCR may comprise initialization, denaturation, annealing, and/or extension/elongation. Initialization may be used for DNA polymerases that require heat activation (e.g., "hot start" PCR). Initialization may comprise heating a sample (e.g., a sample in an assay tube) to a high temperature (e.g., 94-96° C. [201-205° F.) or 98° C. [208° F.], if thermostable polymerases are used), which may be maintained for about 1-10 minutes. Denaturation may comprise heating (e.g., to 94-98° C. [201-208° F.]) a sample (e.g., a sample in an assay tube) for a given time such as between about 5 seconds and 5 minutes. This may result in DNA melting, or denaturation, of a double-stranded DNA template by breaking hydrogen bonds between complementary bases, yielding two single-stranded nucleic acid molecules (e.g., templates). Annealing may comprise lowering the temperature of a sample (e.g., a sample in an assay tube) to, e.g., 50-65° C. (122-149° F.) for a given time, such as between about 5 seconds and 5 minutes, thereby allowing annealing of one or more primers to each of the single-stranded nucleic acid templates. At least two different primers may be included in the reaction mixture, including one for each of the two single-stranded nucleic acid templates containing a target region. The primers may be single-stranded nucleic acid molecules themselves. Conditions suitable for effective extension/elongation may depend on the DNA polymerase used. Extension/elongation comprises synthesizing a new DNA strand complementary to a single-stranded nucleic acid template by adding, in the presence of a DNA polymerase, free dNTPs from a reaction mixture that are complementary to the template in the 5'-to-3' direction and condensing the 5'-phosphate group of the dNTPs with the 3'-hydroxy group at the end of the nascent (elongating) DNA strand. The time required for extension/elongation may depend on the DNA polymerase used and/or on the length of the DNA target region to amplify.

Denaturation, annealing, and extension/elongation may constitute a single thermal cycle. Multiple cycles may be required to amplify a DNA target to a detectable level.

Figure 4:
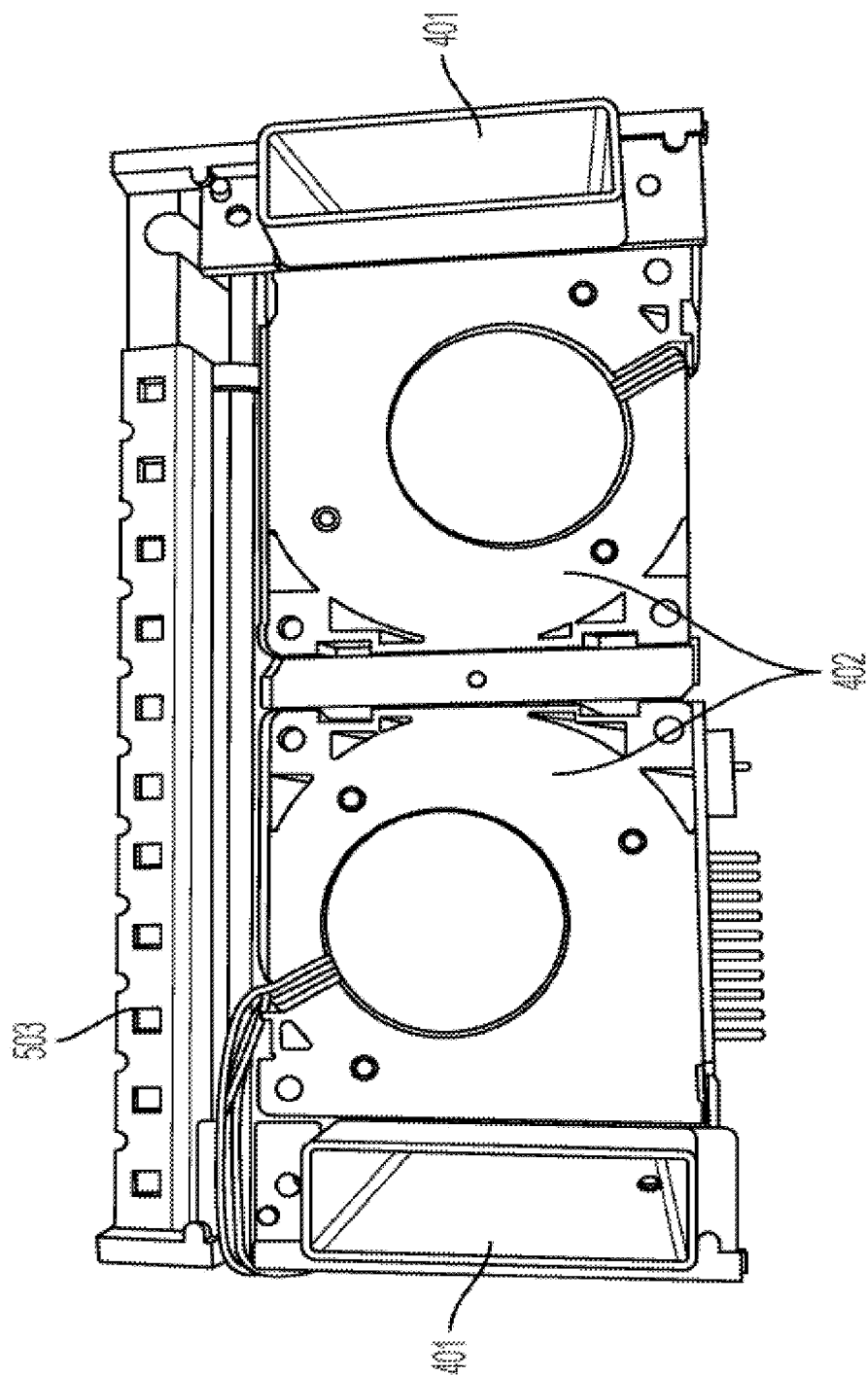
FIG. 4 shows a rear view of an internal mechanism for a portable analytic device with a circuit board removed, thereby exposing fans of the internal mechanism.

The temperature of a block may be regulated in any useful way. Thermal energy may be provided to or removed from a sample (e.g., a sample in an assay tube) by heating or cooling, respectively, the block. A temperature of a block may be controlled (e.g., increased or decreased) using a heating unit (e.g., comprising a resistive, ohmic heater, or flexible heater) and/or a cooling unit (e.g., comprising a thermoelectric cooler or a fan). Temperature monitoring may be necessary for thermocycling applications. Accordingly, a heating or cooling unit may also comprise one or more thermistors and/or temperature transducers to monitor and/or provide feedback to a heating or cooling unit to regulate the temperature of a block. A heating or cooling unit may be disposed adjacent to a block (e.g., on a surface of a block). Alternatively, a heating or cooling unit may be disposed within a recess along a surface of a block. A cooling unit may comprise a fan disposed away (e.g., not in direct contact with) a block. A fan may be used to apply a positive or negative pressure to a volume adjacent to a block, thereby evacuating the area surrounding the block. By evacuating the area surrounding the block, which may comprise air having radiant heat energy from the block, the temperature of the block may be reduced. A fan may be used to generate a vacuum to evacuate radiant heat surrounding the block. Alternatively, a fan may be used to generate positive pressure to exhaust or force radiant heat surrounding the block (e.g., a fluid comprising heat from the block) out of the analytic device. As shown in FIGS. 4A-4B, radiant heat surrounding the block may be removed from the analytic device through one or more vents 401 disposed on the analytic device. One or more fans 402 may be fluidly connected to the space surrounding the block and one or more vents. An analytic device may comprise any number of fans. For example, an analytic device may comprise 1, 2, 3, 4, 5, or more fans. An analytic device may comprise one fan for each block.

Carriage

Figure 5A:
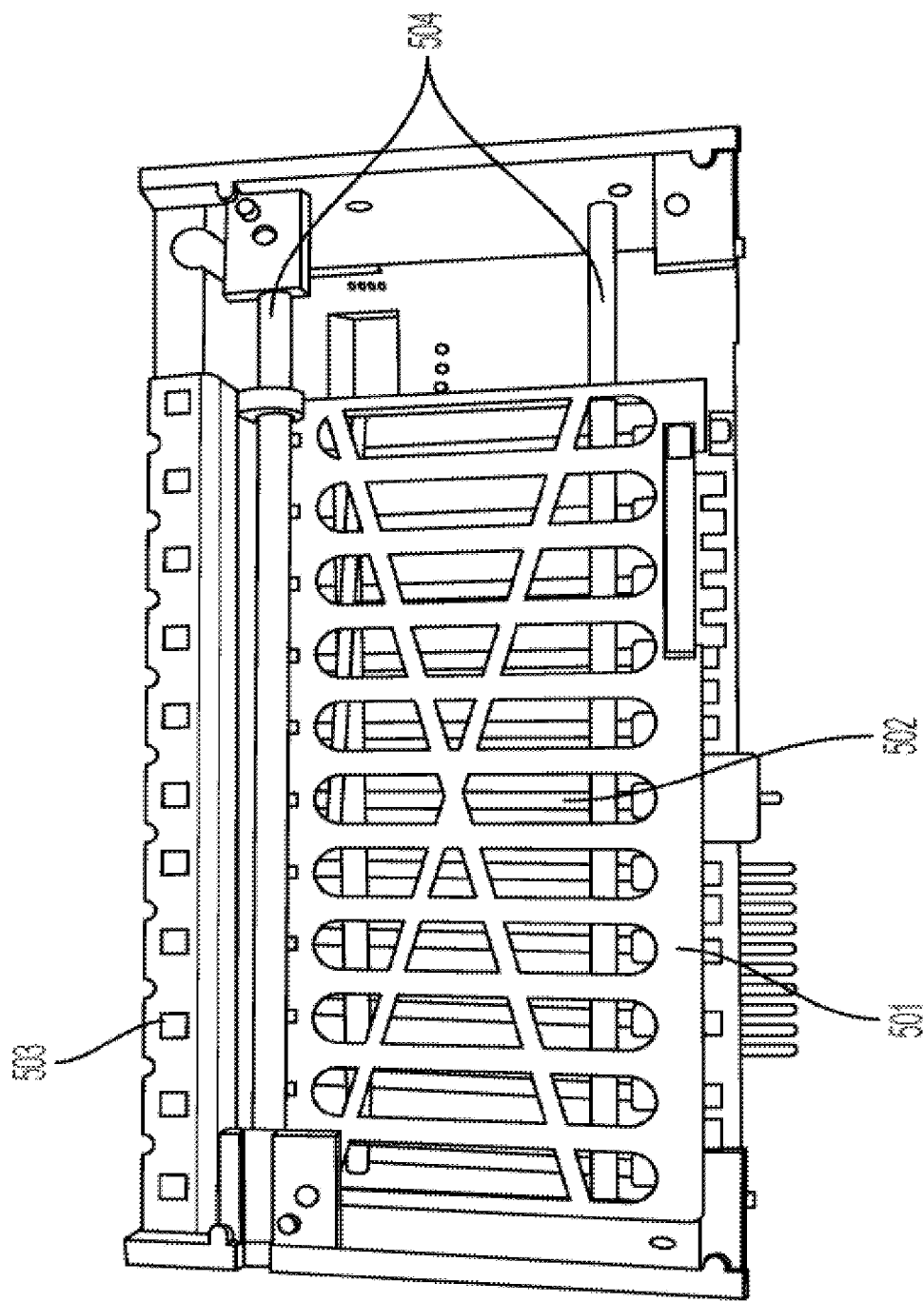
FIG. 5A shows a rear view of an internal mechanism for a portable analytic device with a circuit board and fans removed, thereby exposing a moving carriage of the internal mechanism.
Figure 5B:
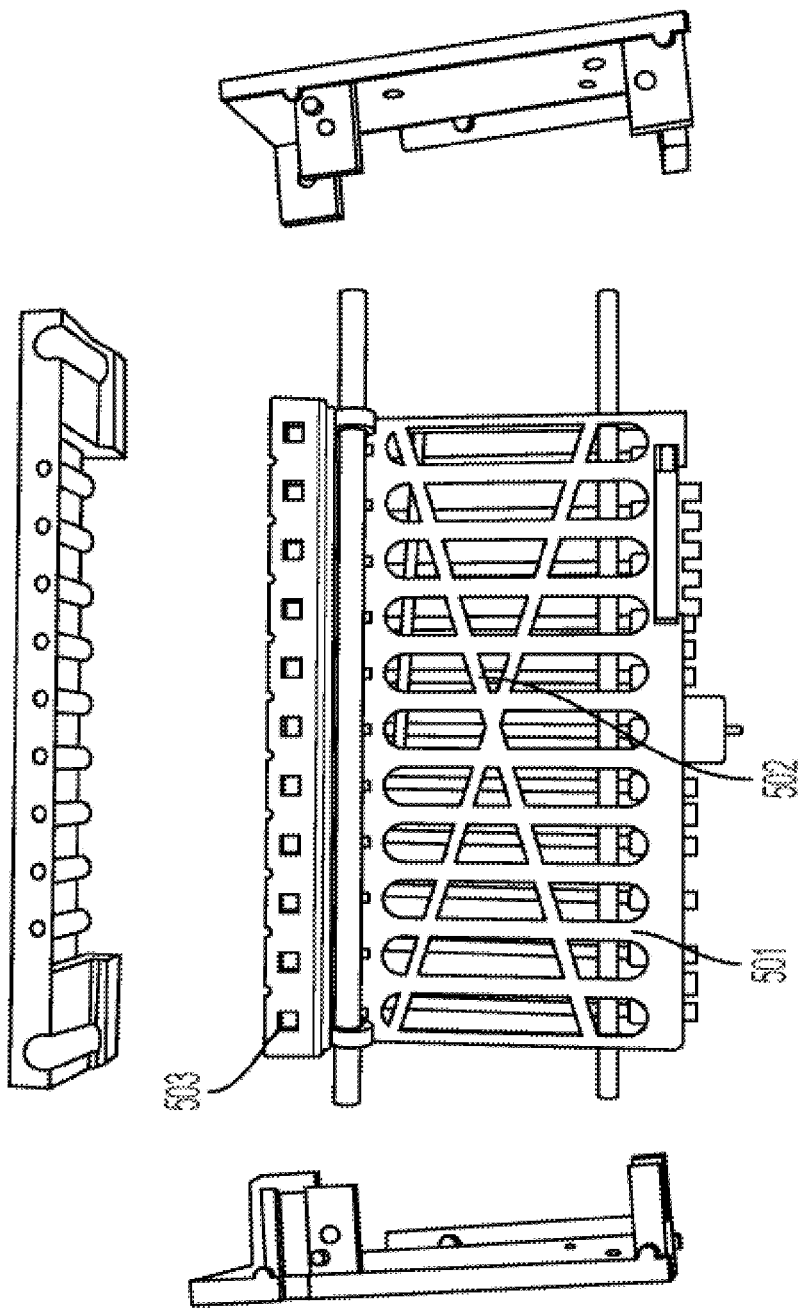
FIG. 5B shows a deconstructed view of a moving carriage of the internal mechanism.
Figure 5C:
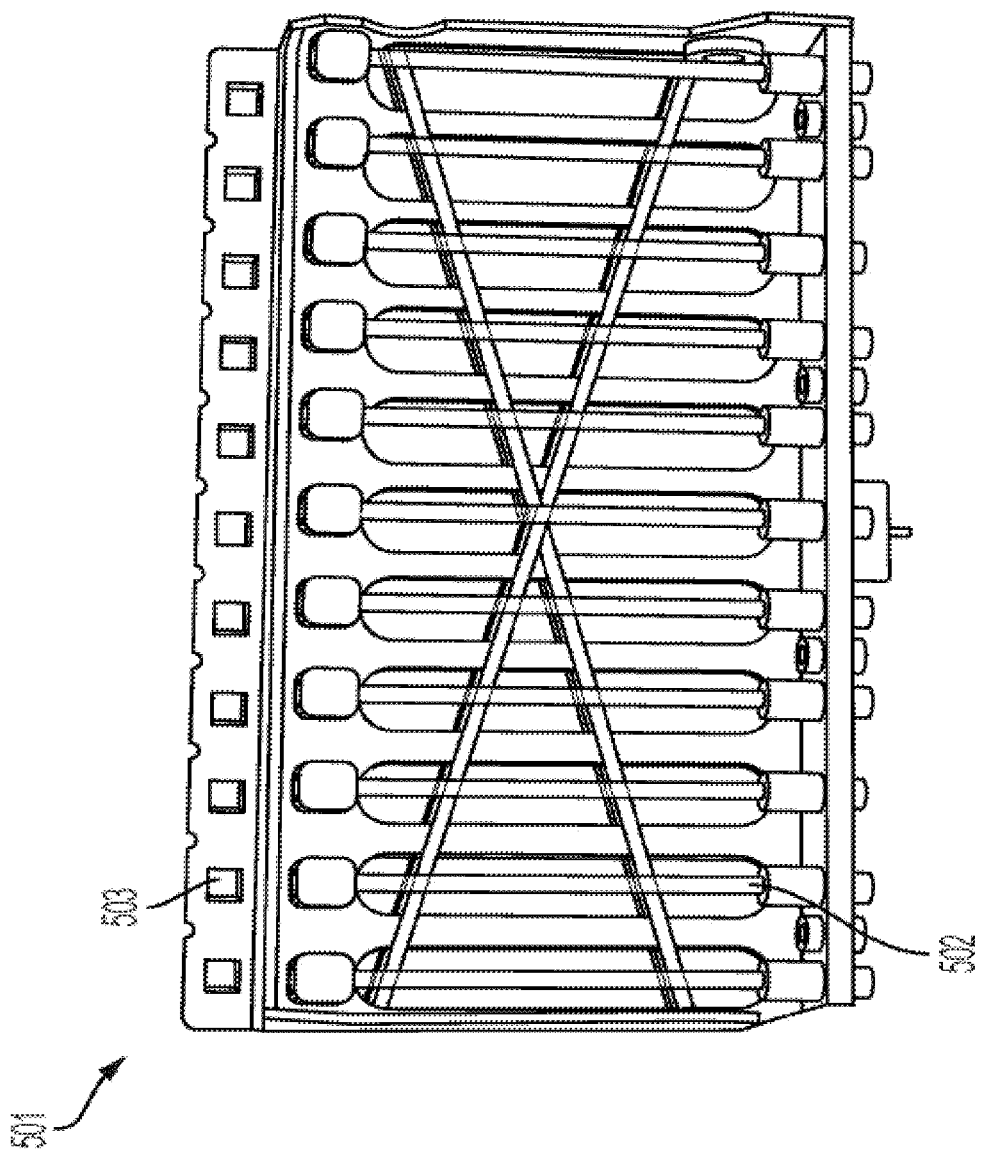
FIG. 5C shows a front view of a moving carriage of the internal mechanism, the moving carriage having multiple light paths.

An analytic device may comprise a carriage. A carriage may be used to hold in place or shift one or more optical components (e.g., an optical filter such as an emission filter or an excitation filter, a light path, and/or a light source) to align with a specified assay tube. As shown in FIG. 5A, a carriage 501 may comprise various optical components, such as an excitation filter (not shown), a light path 502 (e.g., a light pipe) to communicate filtered excitation energy to a sample (e.g., a sample in an assay tube), and an emission filter 503 to filter emission energy prior to detection by a detector. FIG. 5B shows a deconstructed view of the carriage mechanism shown in FIG. 5A. The carriage may be configured to move along one or more paths, grooves, or rails 504. The carriage may be constructed using any useful material. Non-limiting examples of materials that may be used to construct the carriage include polysiloxane, polyphosphazene, low-density polyethylene (ldpe), high-density polyethylene (hdpe), polypropylene (pp), polyvinyl chloride (pvc), polystyrene (ps), nylon, nylon 6, nylon 6,6, teflon (polytetrafluoroethylene), thermoplastic polyurethanes (tpu), polychlorotrifluoroethylene (pctfe), bakelite, kevlar, twaron, mylar, neoprene, nylon, nomex, orlon, rilsan, technora, teflon, ultem, vectran, viton, zylon, polyamides, polycarbonate, polyester, polyethylene, polyvinylidene chloride (pvdc), acrylonitrile butadiene styrene (abs), polyepoxide, polymethyl methacrylate, maleimide, polyetherimide, polylactic acid, furan, silicone, polysulfone, or a metal or metal alloy (e.g., aluminum, brass, copper, iron, and silver). A light path may comprise an open space of a particular geometry and volume. The space may be defined by a container or guide such as a pipe. A light path (e.g., a light pipe) may be constructed using any useful material. Non-limiting examples of materials that may be used to construct a light path (e.g., a light pipe) include glass, silica, fluorozirconate, fluoroaluminate, chalcogenide, plastic, PMMA, polystyrene, silicone resin, and any combination thereof.

A carriage may be a moving carriage. A moving carriage may be used to shift a light path aligning with a first light source and a first assay tube to a second light source and a second assay tube. Similarly, a moving carriage may be used to shift a sample from aligning with a first light path to align with a second light path. An analytic device comprising a moving carriage may provide certain advantages compared to an analytic device comprising, in lieu of a moving carriage, a stationary component. For example, the inclusion of a moving carriage may allow multiple assay tubes to share light paths and associated components such as optical filters (e.g., excitation and emission filters). This may reduce the cost of producing the analytic device (e.g., by requiring fewer optical filters, e.g., excitation and emission filters, which may be costly). The sharing of light paths may also reduce the overall size of the analytic device (e.g., by reducing the number of optical components necessary for analyzing the sample in each assay tube), thereby making the analytic device more portable. A moving carriage may be configured to move from a first or original position to a final position, making one or more stops at specified positions between the original and final positions. The path between the original and final positions may be a linear path and may comprise one or more grooves, tracks, or rails along which a moving carriage may travel. The path between the original and final positions may comprise one or more specified positions at which the moving carriage may stop (e.g., via a manual or automated control, as described herein). The one or more specified positions may correspond to the positions of one or more assay tubes or seats or housings therefor in an analytic device. A specified position may comprise a mechanical component such as a key to facilitate positioning of the moving carriage in the specified position (e.g., beneath an assay tube). Movement of a moving carriage may be achieved using a variety of methods. For example, an electric motor may be used to move the carriage from a first position to a second position. A motor having a cam may be used to move the carriage via a belt coupled to the carriage and the cam. Movement of a moving carriage may be achieved using a magnetic levitation system. For example, a carriage may be slidably disposed on or in one or more electrified rails or grooves, and a magnetic force generated within a rail or groove may be used to move the carriage. A spring may be used to return a moving carriage to its original position, e.g., after it has moved from its original position b a final position, such as the end of a rail, track, or groove. It is contemplated that constructing the moving carriage using lighter weight materials may reduce the energy required to move the carriage, thereby increasing the amount of energy available for heating and/or cooling the sample and/or other processes.

Figure 6A:
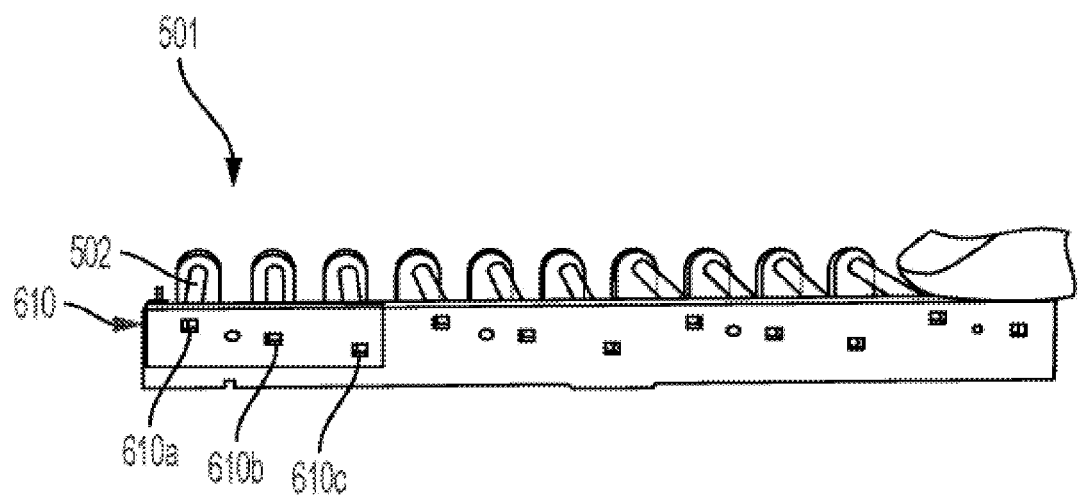
FIG. 6A shows a bottom view of a moving carriage of the internal mechanism, the bottom of the moving carriage having multiple optical filters, which may be offset from one another.

A carriage may comprise one or more optical filters (e.g., excitation or emission filters) and one or more light pipes. FIG. 6A shows a carriage comprising one or more excitation filters 610*a* (red), 610*b* (yellow), and 610*c* (blue). A carriage may also comprise one or more emission filters. A light pipe may extend from an optical filter (e.g., an excitation filter) to an assay tube containing a sample.

An analytic device may comprise any useful optical filters (e.g., excitation and/or emission filters). Filters may be optical bandpass filters (e.g., optical interference films) having a bandpass at a frequency that may be optimal for one or more of (i) the excitation wavelength of a fluorophore or dye, and (ii) the emission wavelength of a fluorophore or dye. A filter may substantially attenuate non-bandpass frequencies to prevent transmission of undesirable light. For example, when using SYBR Green dye, an excitation filter bandpass may center around a wavelength of 485 nm, and an emission filter bandpass may center around a wavelength of 555 nm. An optical filter (e.g., an excitation filter and/or an emission filter) may be tilted (e.g., a plane containing the filter may be disposed at an angle) relative to a light path.

Excitation Source

Figure 6B:
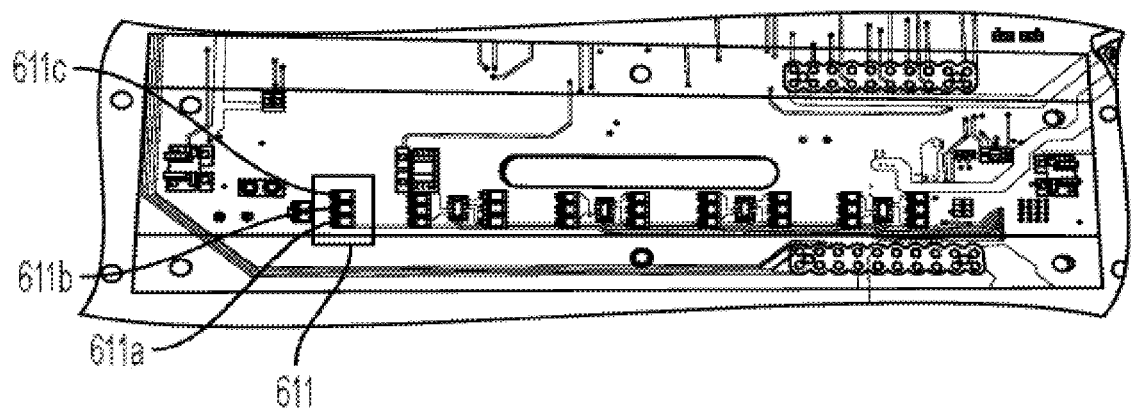
FIG. 6B shows a circuit board having multiple excitation sources (e.g., LEDs), which are spaced to correspond to the offset of the optical filters shown in FIG. 6A.

An analytic device may comprise one or more excitation sources. An excitation source may be disposed on a carriage (e.g., a moving carriage, as described herein) and may be configured to deliver excitation energy to a sample (e.g., a sample in an assay tube) through an excitation filter and a light path. For an analytic device comprising a moving carriage, a single excitation source disposed on the carriage may be configured to deliver excitation energy to two or more samples (e.g., two or more samples in two or more assay tubes) through the same excitation filter and light path (e.g., as the moving carriage aligns the excitation source and light path with different assay tubes containing different samples). As shown in FIG. 6B, an analytic device may have a dedicated set 611 of excitation sources 611*a* (blue), 611*b* (yellow), and 611*c* (red) for each assay tube.

An excitation source may comprise a Light Emitting Diode (LED) or an array of LEDs (e.g., a set of single-color LEDs). An LED may have any useful size, shape, wavelength, or other characteristic. An LED may be a high power LED that may emit greater than or equal to about 1 mW of excitation energy. A high power LED may emit at least about 5 mW of excitation energy. An LED or an array of LEDs may emit, for example, about 50 mW of excitation energy. An array of high-powered LEDs may be used that draws, for example, about 10 watts of energy or less, or about 10 watts of energy or more. The total power draw may depend on the power of each LED and the number of LEDs in the array. The use of LEDs in an analytic device as an excitation source may be beneficial, for example, because an LED array may result in a significant reduction in power requirement over other light sources such as halogen light sources. An excitation source may use a power of about 1 microwatt ($\mu$W) or less. Alternatively, an excitation source may use a power of about 1 microwatt ($\mu$W), about 5 $\mu$W, about 25 $\mu$W, about 50 $\mu$W, about 100 $\mu$W, about 1 milliwatt (mW), about 5 mW, about 25 mW, about 50 mW, about 100 mW, about 1 W, about 5 W, about 50 W, or about 100 W or more, individually or when in usedin an array. In some cases, a cooling device such as, but not limited to, a heat sink or fan may be used to cool the excitation source or a component thereof.

An excitation source may comprise an organic LED (OLED) or an array of OLEDs. An OLED may have any useful size, shape, wavelength, or other characteristic. An OLED may provide luminescence over a large area, for example, to provide excitation energy to multiple assay tubes simultaneously. Scatter or cross-talk light between multiple sample wells (e.g., seats or housings for assay tubes) for such an OLED may be reduced by overlaying a mask on the OLED or by patterning the luminescence of the OLED to operatively align with the multiple sample wells. An OLED may be a low power consumption device. An OLED may include a small-molecule OLED and/or a polymer-based OLED also known as a Light-Emitting Polymer (LEP). A small-molecule OLED that is deposited on a substrate may be used. An OLED that is deposited on a surface by vapor-deposition technique may be used. An OLED may also be deposited on a surface by, for example, silk-screening. An LEP may be used that is deposited by, for example, via solvent coating.

An excitation source may comprise an array of LEDs or OLEDs 611*a*-611*c* (e.g., multiple single-color LEDs). The array may be constructed and arranged in any configuration. For example, the excitation sources in an array may be arranged linearly along the axis of movement of a moving carriage. Alternatively, as shown in FIG. 6B, the excitation sources in an array may be arranged linearly perpendicular to the axis of movement of a moving carriage. In such a configuration, the light paths 502 may be disposed at an angle relative to the base of the moving carriage. A light path extending from the base of the moving carriage (e.g., from an excitation filter disposed in the base of the moving carriage) may be perpendicular to the base of the carriage, or not perpendicular to the base of the carriage (e.g., at an angle other than 90 degrees to the base of the carriage).

One or more lenses may be used to direct, re-direct, focus, disperse, or collimate excitation or emission energy. For example, a lens may be used to focus excitation energy onto a sample (e.g., a sample in an assay tube). In another example, a lens may be used to collimate excitation energy from an excitation source. Non-limiting examples of lenses that may be used include a biconvex lens, a plano-convex lens, a positive meniscus lens, a negative meniscus lens, a plano-concave lens, a biconcave lens, a Fresnel lens, a cylindrical lens, a lenticular lens, and a gradient index lens. For example, a Fresnel lens may be used to collimate excitation energy from an excitation source and direct the excitation energy into a light path. A Fresnel lens may be made much thinner than a comparable plano-convex lens, in some cases taking the form of a flat sheet, which may be advantageous for producing a portable analytic device.

Figure 7:
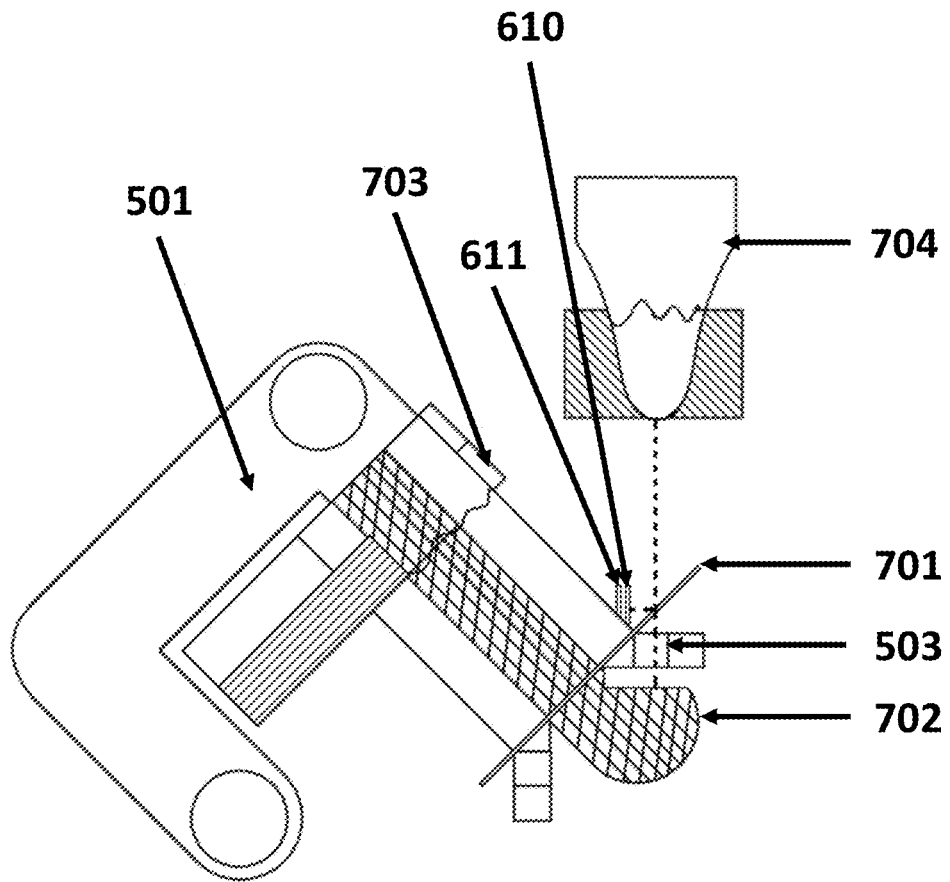
FIG. 7 shows another example of a moving carriage, having optical components (e.g., emission filters, excitation filters, LEDs and/or dichroic beam splitters) that rotate using a pinion mechanism.

FIG. 7 shows an additional configuration for moving carriage 501 in which excitation source 611, excitation filter 610, dichroic beam splitter 701, emission filter 503, and detector 702 are disposed on moving carriage 501. Excitation source 611, excitation filter 610, dichroic beam splitter 701, and emission filter 503 may be disposed on a rotating pinion mechanism 703 such that as moving carriage 501 aligns with each sample, the pinion mechanism may be used to rotate the optical components 611, 610, 701, and 503 to provide to a desired excitation energy to a sample (e.g., a sample in an assay tube), and detect an emission energy from the sample 704.

Figure 8:
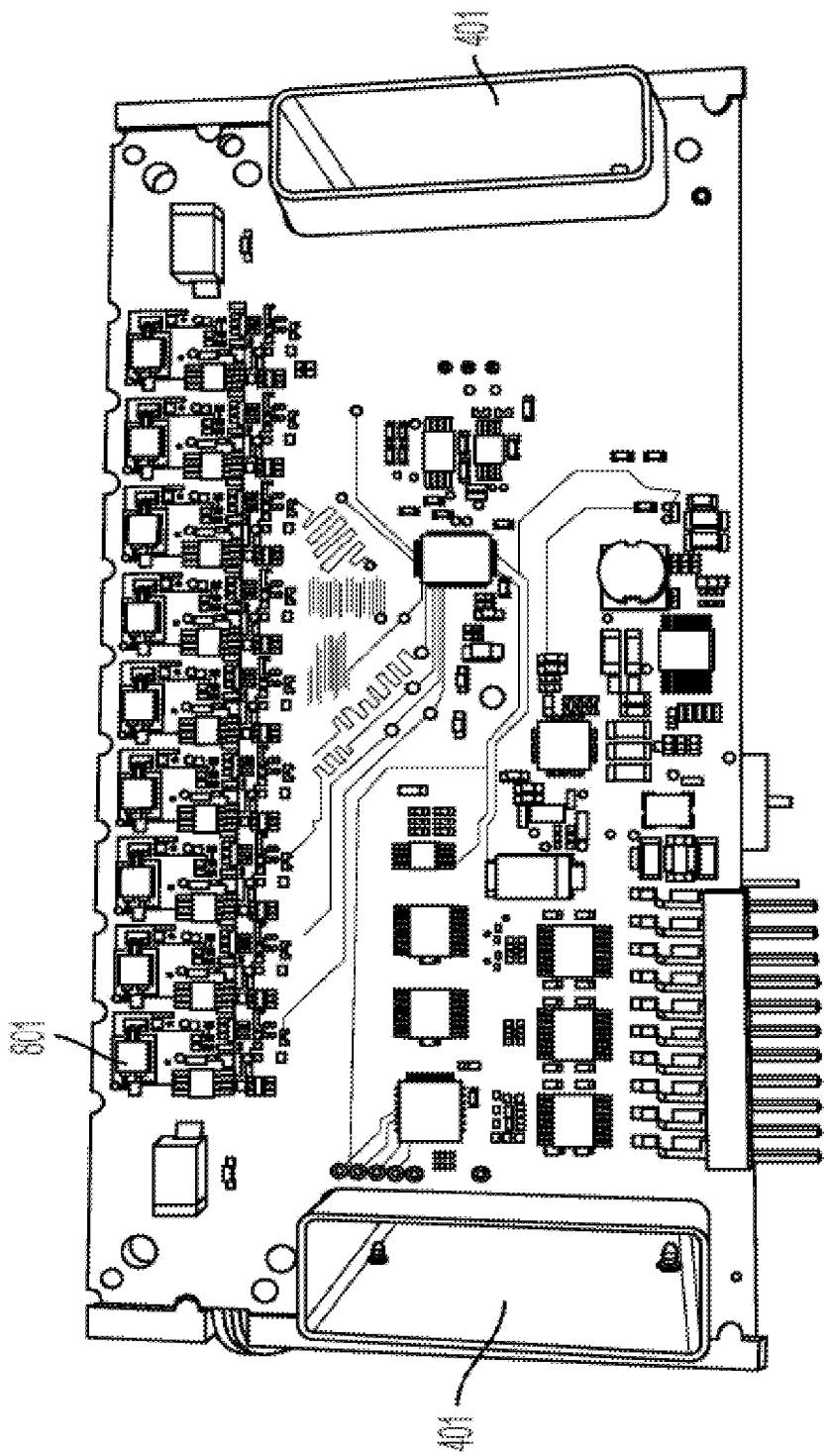
FIG. 8 shows rear view of an internal mechanism for a portable analytic device for analyzing a biological sample.

The analytic device may also comprise a detector such as detector 801, as shown in FIG. 8. The detector may be configured to receive emission energy from a sample (e.g., a sample in an assay tube), and possibly through an emission filter. Accordingly, the detector may comprise any suitable photodetector, such as, for example, an optical detector, a photoresistor, a photovoltaic cell, a photo diode, a phototube, a photomultiplier tube, a charge coupled device (CCD) camera, a complementary metal oxide semiconductor (CMOS), or any combination thereof. Emission energy may be produced by any suitable source, such as, for example, by the excitation of a component of a sample in an assay tube (e.g., an excitable fluorophore). A detector may be configured to selectively receive emission energy from a sample (e.g., energy of a particular wavelength or intensity). A detector may comprise a plurality of detectors (e.g., a series of photodetectors, each configured to receive a light beam having a different wavelength than the light beams received by the other photodetectors).

Figure 14A:
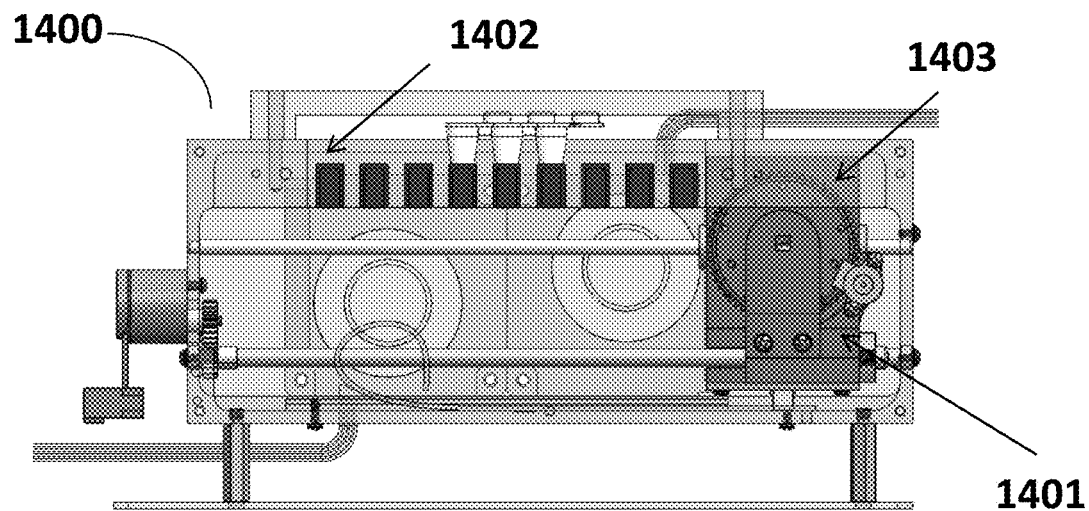
FIG. 14A shows a front view of a movable carriage inside an example portable device.
Figure 14B:
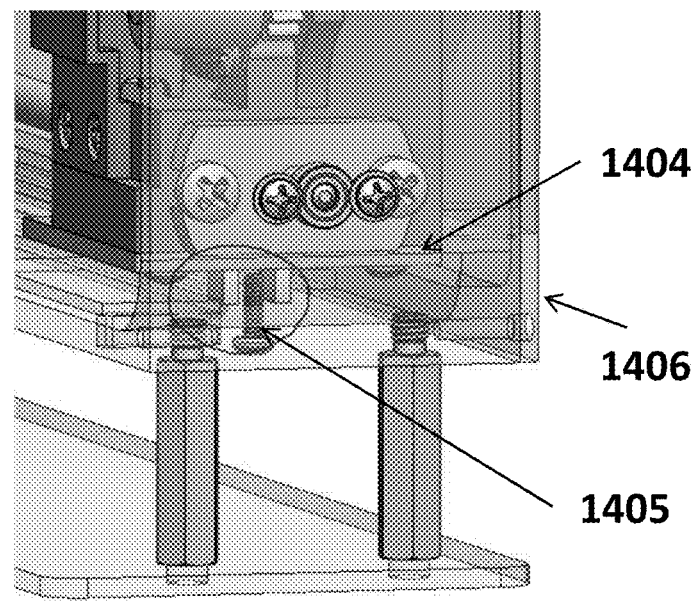
FIG. 14B shows a side view of an example portable device.
Figure 14C:
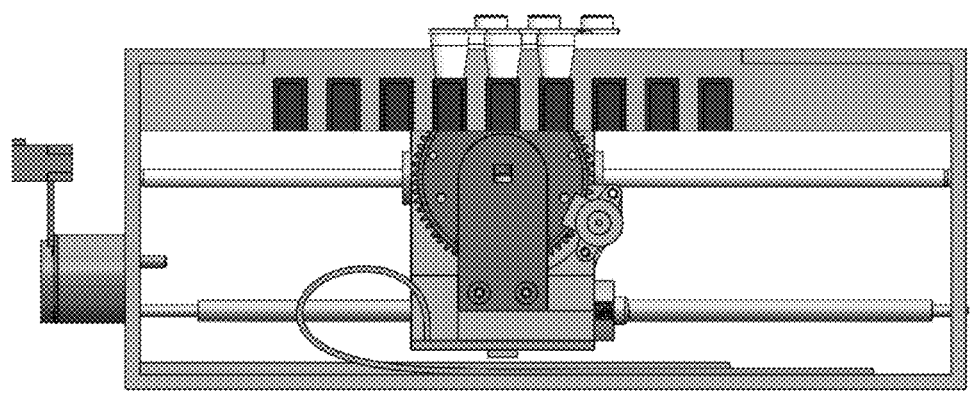
FIG. 14C shows an additional front view of the example movable carriage inside a portable device, FIG. 141) shows a back view of the example movable carriage.
Figure 14D:
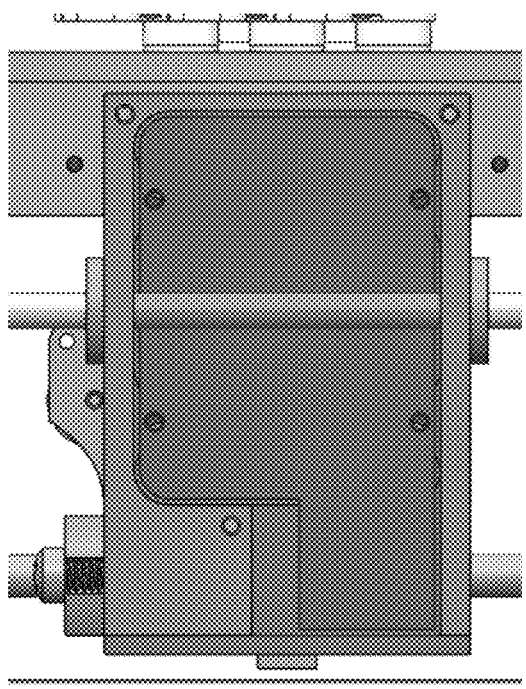

A movable carriage may comprise a wheel-shaped (or circular) component to carry one or more optical elements, such as filters. As an alternative or in addition to, the wheel-shaped component can include a mirror, light source (e.g., an LED, a single pixel LED, or a multi-pixel LED), prism, lens, or any combination thereof. The movable carriage can be configured to move in a linear path and stopped at a specific position. For example, the movable carriage can be configured to move along the axis of blocks and stopped at each block for data acquisition from a sample tube inserted into each block. The wheel-shaped component inside the movable carriage may be movable along the wheel axle to switch between different filters. For example, FIG. 14A shows a front view of a movable carriage 1401 inside a portable analytic device 1400. In this example device, the wheel-shaped component 1403 of the movable carriage 1401 carries 9 pairs of filters (a pair of filter comprises an excitation filter and an emission filter). The movable carriage can move along the different blocks 1402. FIG. 14B shows a zoom-in view of a portion of the movable carriage. The bottom PCB 1404 may comprise a break beam switch. The chassis 1406 can comprise two screws to trigger beam switch stop carriage from hitting chassis walls. One screw 1405 is shown in FIG. 14B. FIG. 14C shows an additional front view of the example movable carriage stopped at a different position inside a portable analytic device. FIG. 14D shows a back view of the example movable carriage.

The wheel-shaped component can have other shapes. For example, the elements of such wheel-shaped component may be included in a component that is triangular, square, rectangular, pentagonal, hexagonal, or any other shape or combination of shapes thereof.

Figure 15:
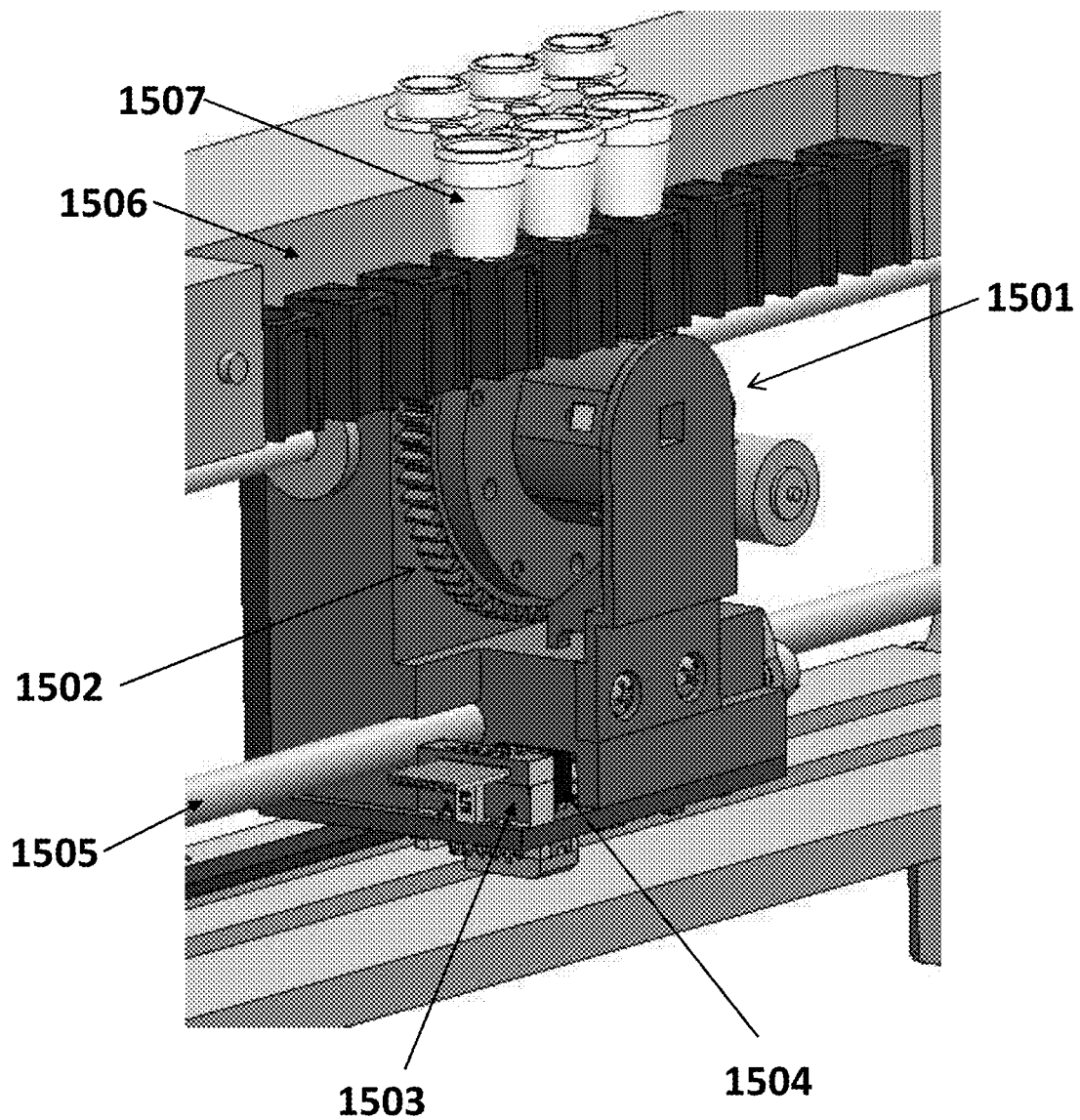
FIG. 15 shows a zoom-in view of an example movable carriage having a circular (or wheel-shaped) component.

FIG. 15 shows a zoom-in view of an example movable carriage 1501 having a wheel-shaped component 1502. The bottom portion of the movable carriage can comprise a ribbon wire 1503 and an actuator (e.g., stepper motor) 1504. The stepper motor 1504 may be used to move the movable carriage along a guide 1505 among the sample stations 1506. A given one of the sample stations 1506 may include a vial 1507 having a solution containing a biological sample and reagents necessary for sample processing (e.g., polymerase chain reaction (PCR)). The movable carriage 1501 may include another actuator (e.g., stepper motor) for rotating the movable carriage 1501 along an axis orthogonal to the guide 1505.

Figure 16:
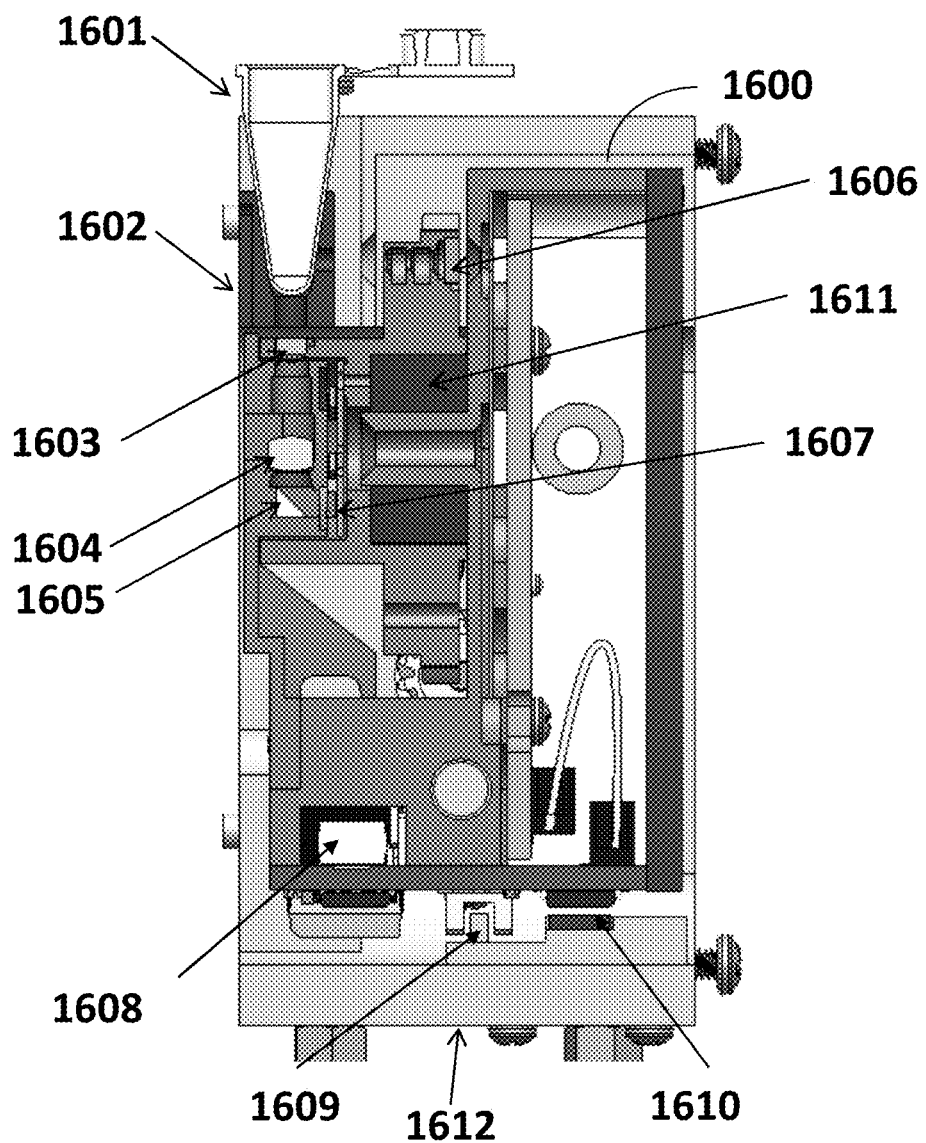
FIG. 16 shows a side view of the internal mechanism of an example movable carriage inside a portable analytic device.
Figure 17:
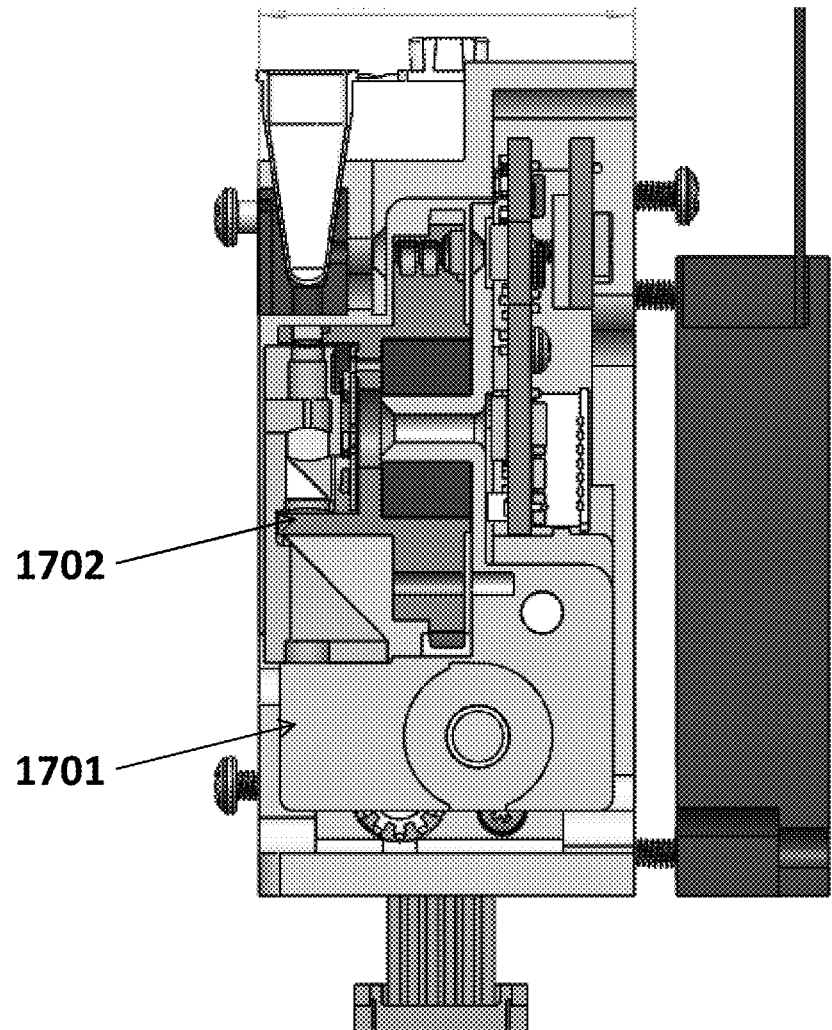
FIG. 17 shows a side view of the internal mechanism of an example movable carriage inside a portable analytic device.

FIG. 16 shows a side view of the internal mechanism of the example movable carriage 1600. The movable carriage can comprise an optical system having an excitation filter 1603, a lens 1604, a mirror 1605, an emission filter 1606, and a light source 1607 (e.g., LED). The movable carriage can comprise one or more magnetic pieces 1611. The movable carriage may comprise multiple excitation filters, emission filters, and light sources. Each light source may be configured to be used with a given pair of excitation filter and emission filter for data acquisition from a sample tube 1601 inserted in a block 1602. Shown in FIG. 16 is an example of one optical system having one given pair of excitation and emission filters. When the wheel-shaped component moves around the wheel axle, another option system having another pair of excitation and emission filters and another light source can be lined up with the sample tube for data acquisition. The movable carriage can comprise at least 1, 2, 3, 4, 5, 6, 7, 8, 9, 10, 11, 12, 13, 14, 15, 16, 17, 18, 19, 20 or more filters. The movable carriage can comprise at least one pair, two pairs, three pairs, four pairs, five pairs, six pairs, seven pairs, eight pairs, nine pairs, ten pairs, eleven pairs, twelve pairs, thirteen pairs, fourteen pairs, fifteen pairs, or more pairs of filters. The movable carriage can further comprise a big capacitor 1608. The chassis 1612 of the portable analytic device can comprise a flag to trigger photo interrupter. The chassis 1612 can comprise a magnetic strip and linear encoder (e.g., a liner encoder having a 0.4 mm gap). The movable carriage can be built with various materials or combinations of materials. For example, shown in FIG. 17, the part 1701 of the movable carriage can be built with metal. The part carrying the optical system 1702 may be built with black dyed micro fine 3D print. The detector board may be fully enclosed for EMI shielding.

Figure 18:
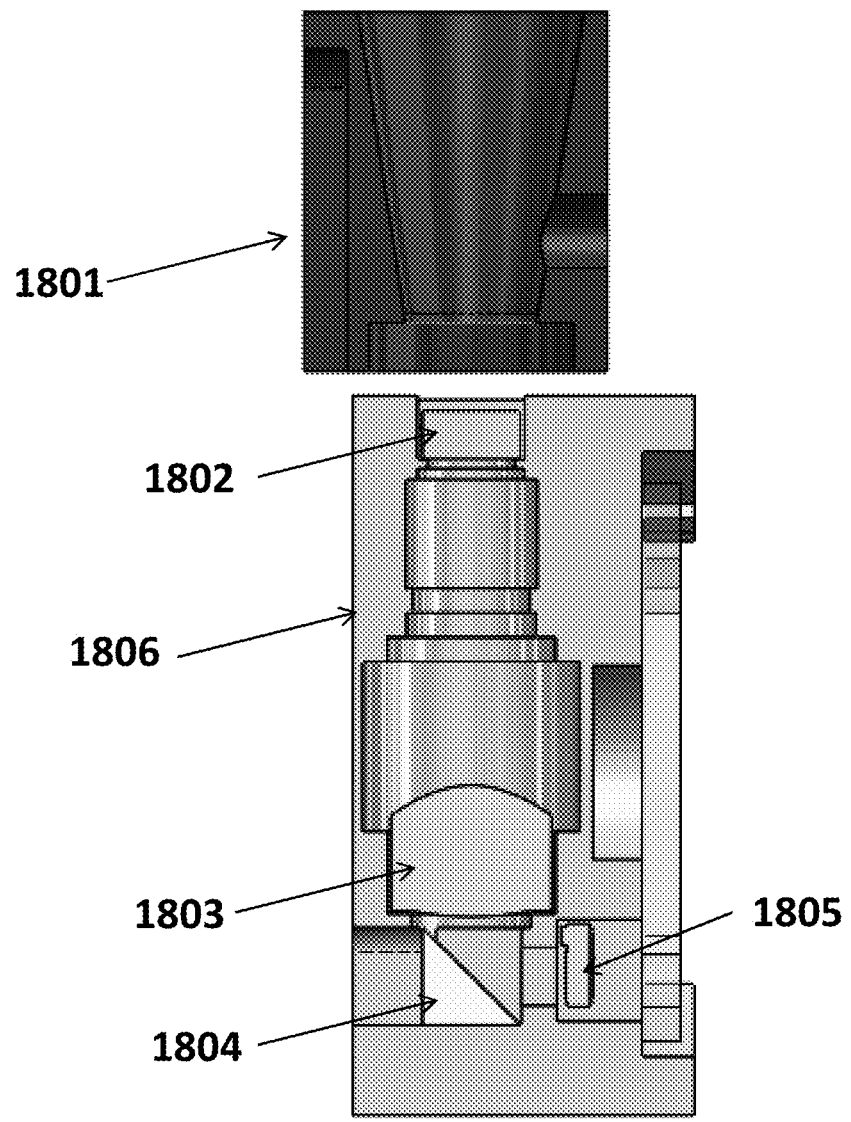
FIG. 18 shows a zoom-in view of an example optical system of the movable carriage.

FIG. 18 shows a zoom-in view of an example mechanism of an optical system of the movable carriage. The lens 1303 can be made of various materials, for example, glass or polycarbonate. The lens 1803 may be mounted in a non-rotating part of the hub 1806 of the wheel-shaped component. The light source (or excitation source) 1305 can be a LED light. The filter 1802 can be an excitation filter. The filter 1302 may provide transmission of a desired excitation wavelength. For example, the light transmitted from the excitation filter may have a center wavelength of at least about 390 nanometers(nm), 434 nm, 445 nm, 469 nm, 475 nm, 497 nm, 542 nm, 559 nm, or 565 nm. The optical system can further comprise a fold mirror 1804. The distance between the light source 1805 and the fold mirror 1804 can vary. Shown in FIG. 18, the part 1801 is a block. In addition, the optical system can comprise an emission filter. The emission filter can provide transmission of a desired emission wavelength. For example, the light transmitted from the emission filter may have a center wavelength of at least about 460 nm, 479 nm, 510 nm, 525 nm, 530 nm, 535 nm, 620 nm, or 630 nm. In some cases, the optical system inside a movable carriage may comprise one or more dichroic filters.

Figure 19A:
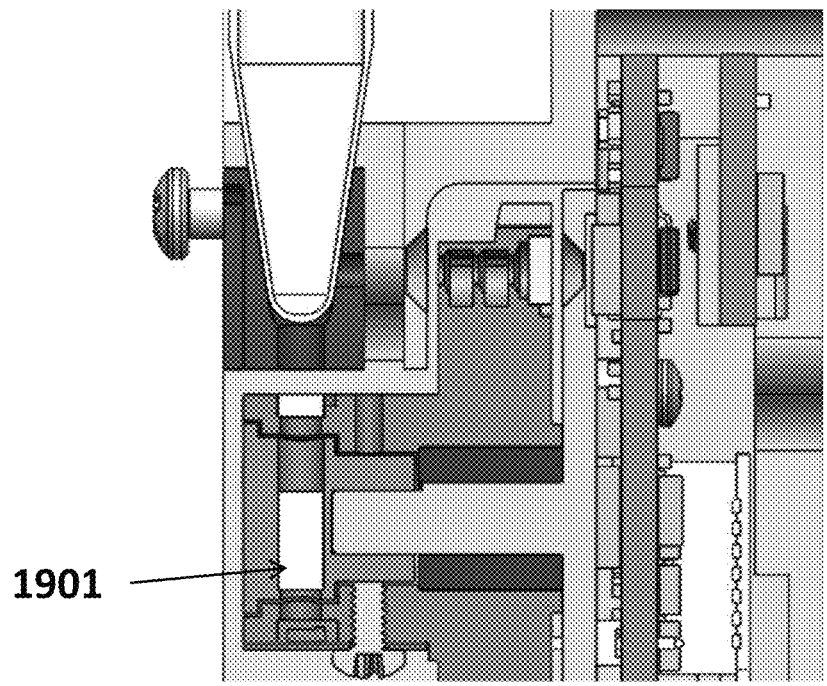
FIG. 19A shows an alternative configuration of the optical system.
Figure 19B:
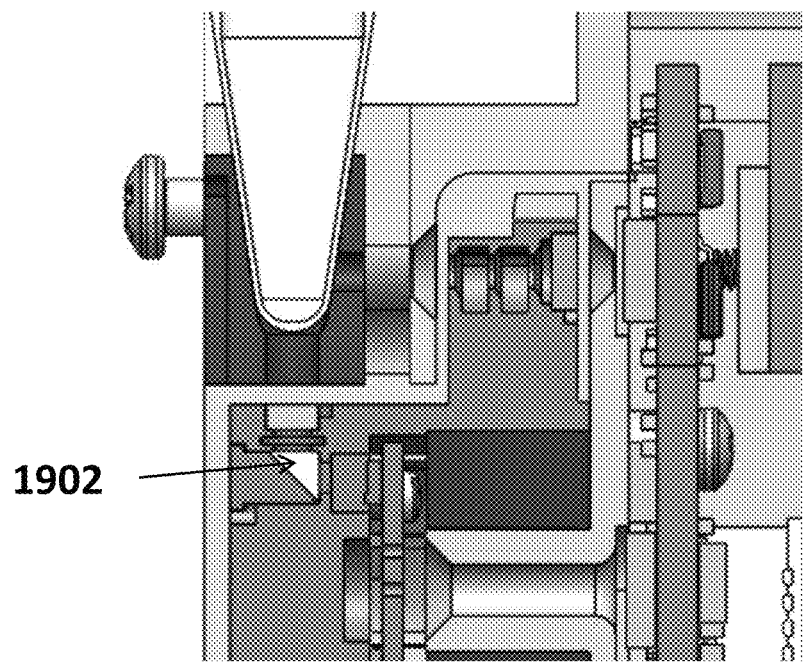
FIG. 19B shows another alternative configuration of the optical system.

The optical system may comprise different components and can be assembled in different configurations. FIGS. 19A and 19B show two additional examples of the optical systems inside of a movable carriage. For example, an optical system of the movable carriage may not comprise a mirror and lens. An optical system may comprise a light path 1901 that allow the light from a light source to reach an excitation filter. For another example, an optical system may comprise a prism 1902 to allow the light from a light source to reach the excitation filter.

Different configurations of the optical systems may result in different properties of the system as demonstrated by parameters such as power to vial, moving carriage baseline, signal to noise ratio (SNR), etc. As used herein, the SNR can be defined using the following equation:

$$SNR = \frac{\text{Total power on detector}}{\text{Power on filter outside} \times \text{degrees that reaches the detector}}$$

where, x is the incidence angle of a light.

Figure 20A:
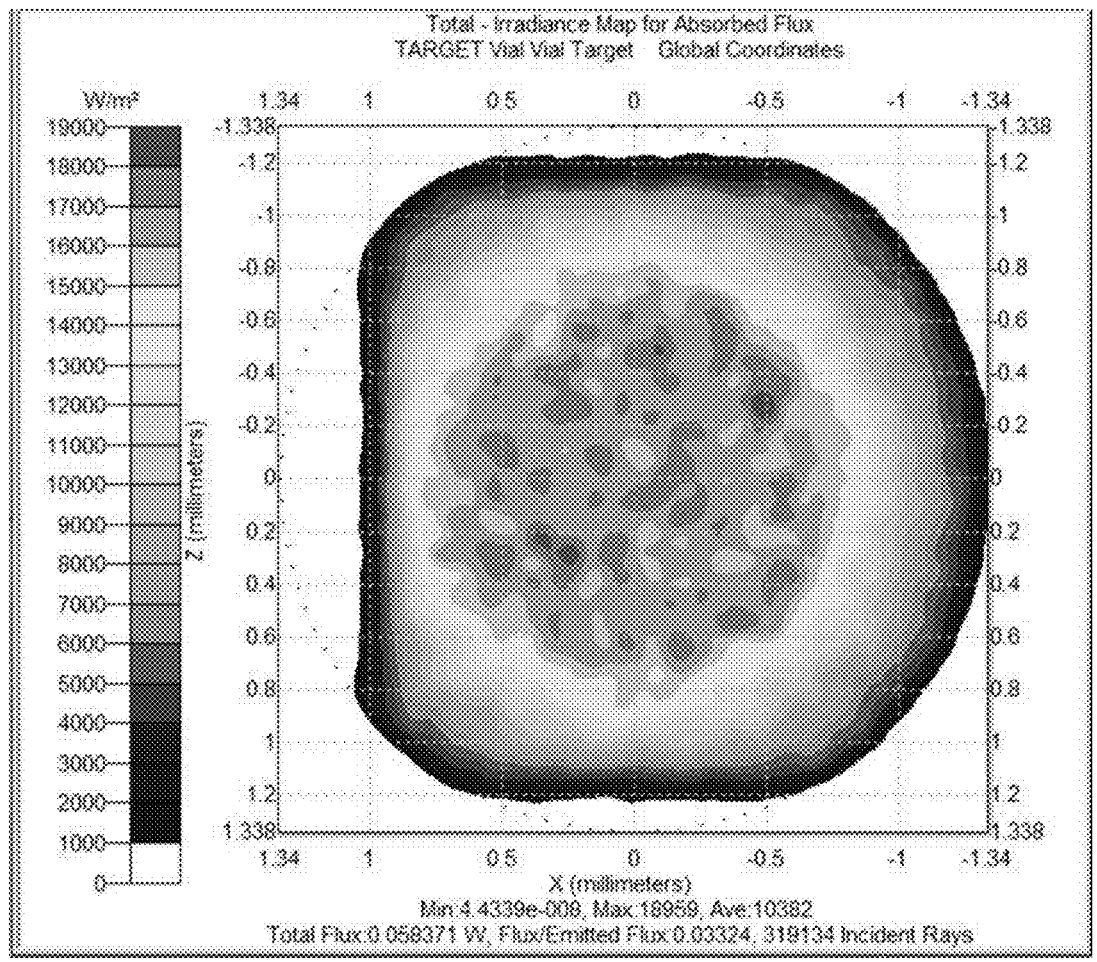
FIG. 20A shows a simulation result of an optical system.
Figure 20B:
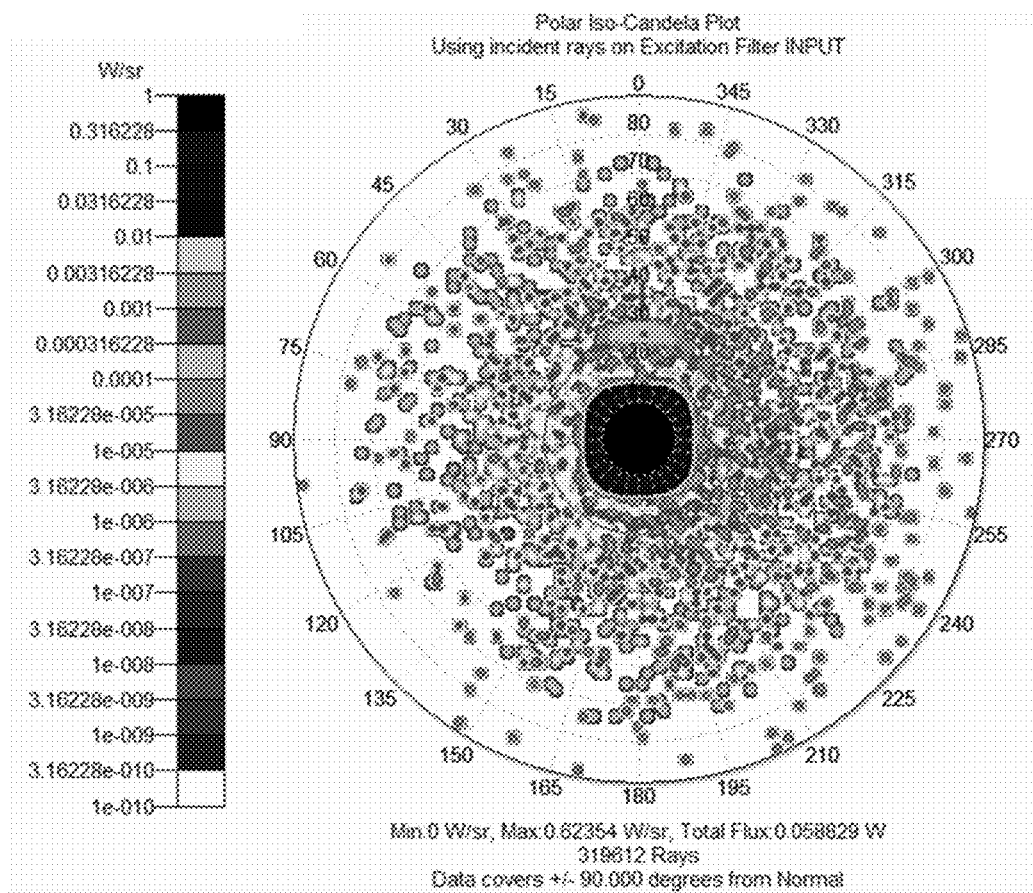
FIG. 20B shows another simulation result of an optical system.
Figure 20C:
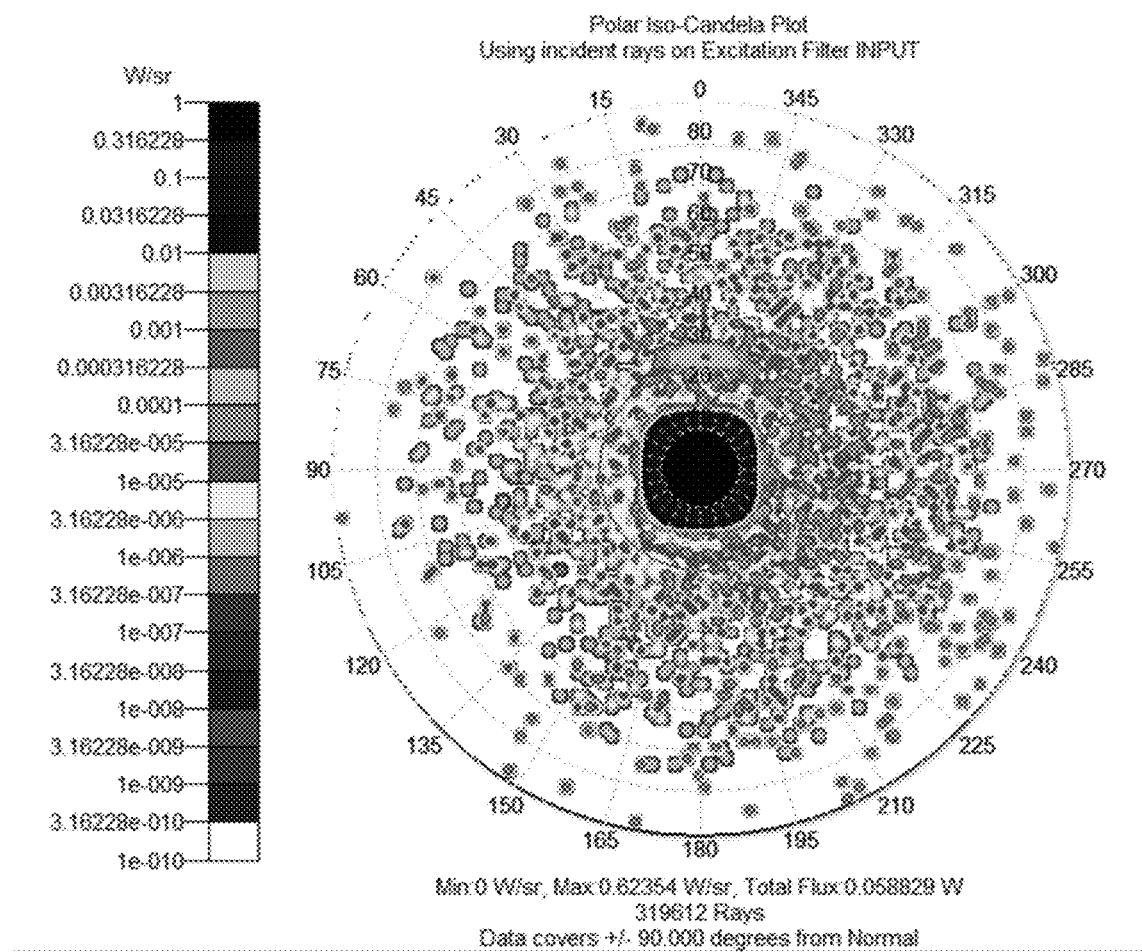
FIG. 20C shows another simulation result of an optical system.
Figure 21A:
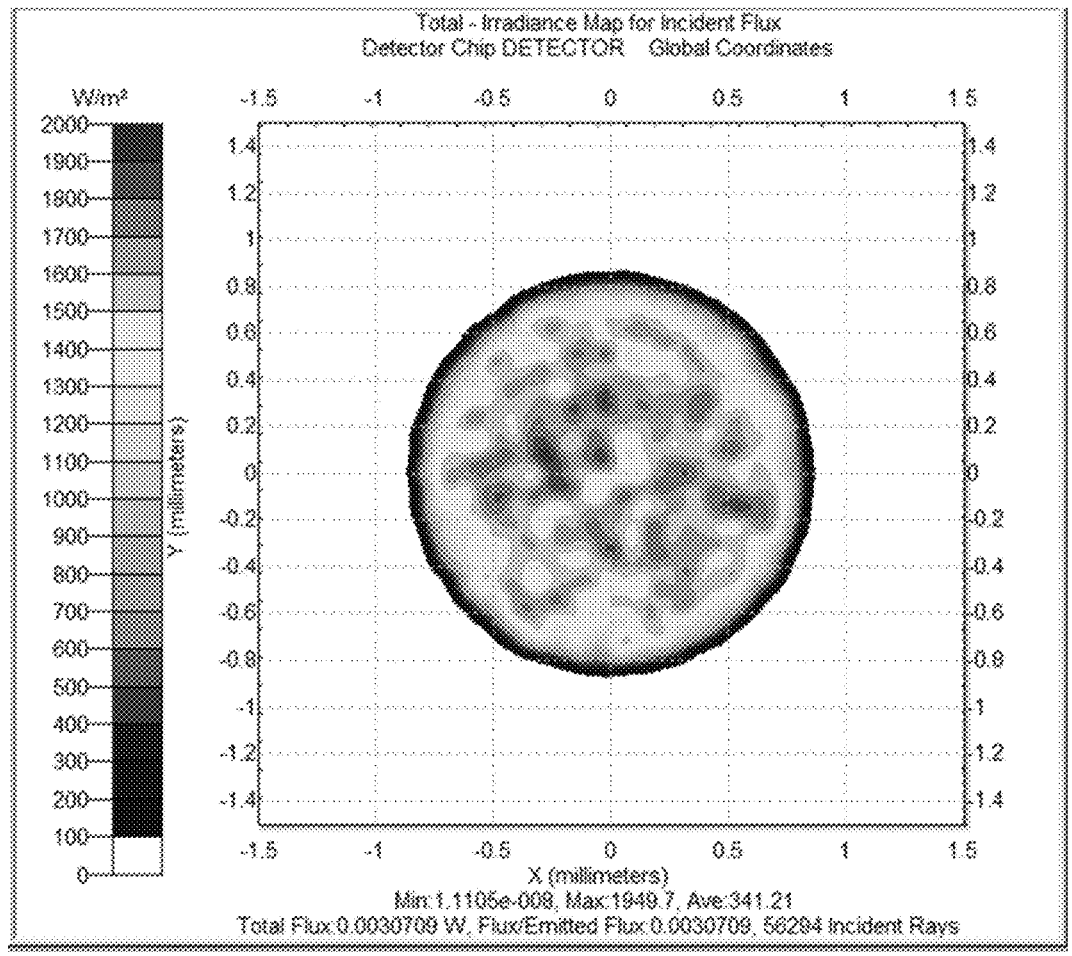
FIG. 21A shows a simulation result of an optical system.
Figure 21B:
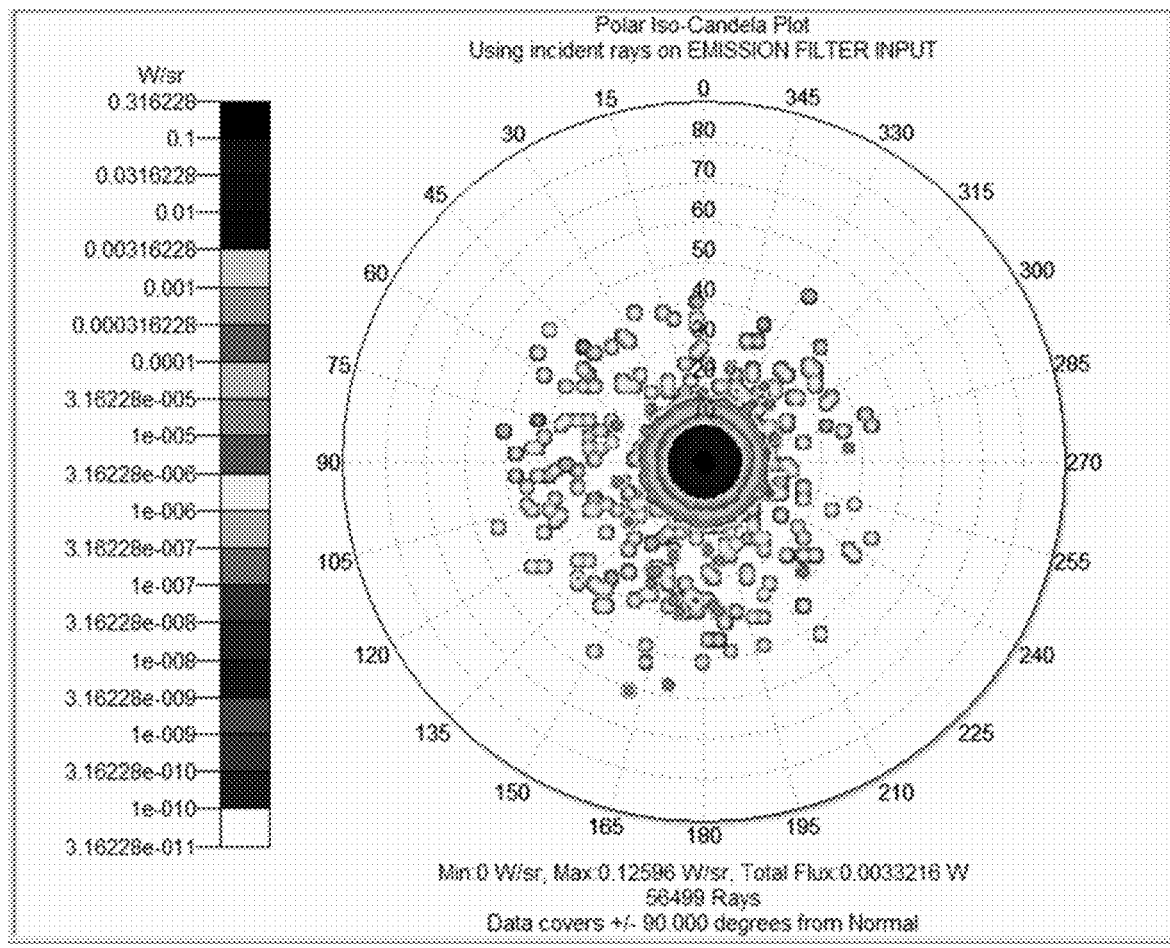
FIG. 21B shows another simulation result of an optical system.
Figure 21C:
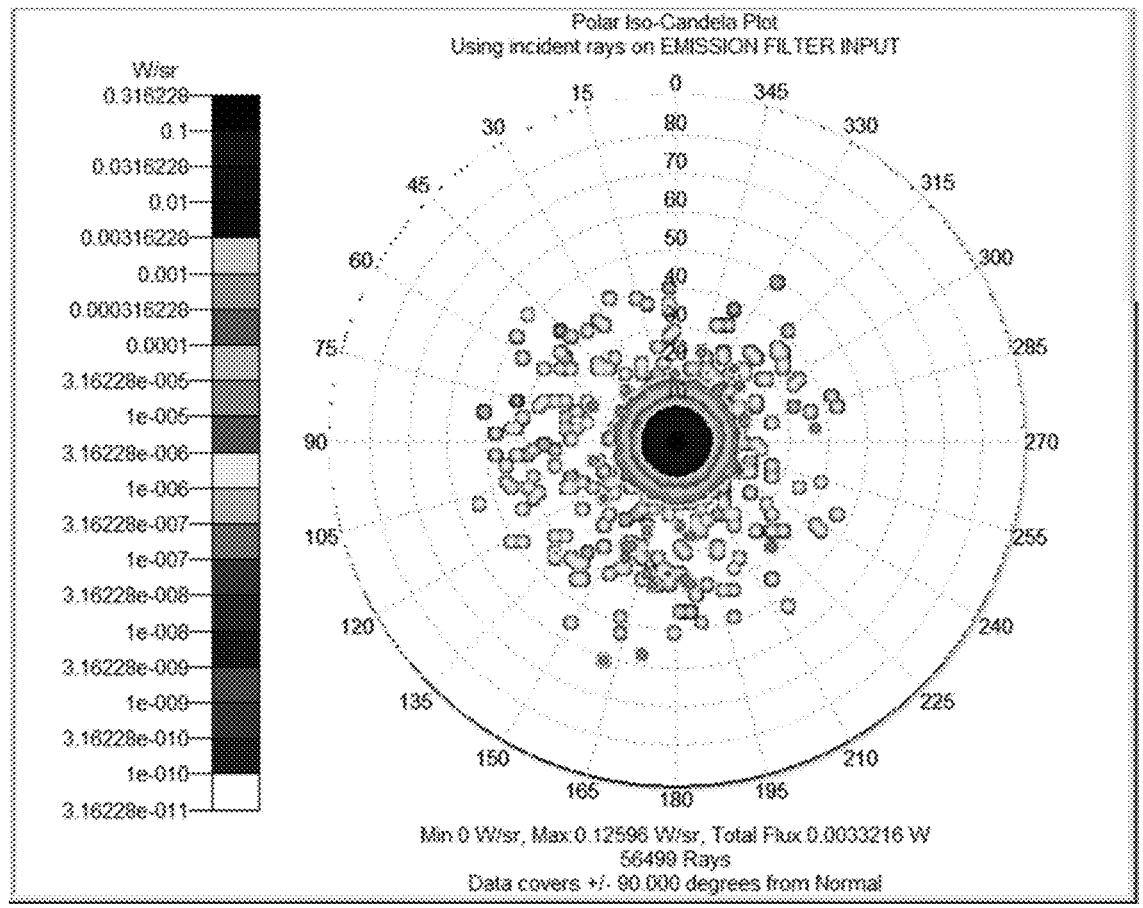
FIG. 21C shows another simulation result of an optical system.

Typically, x may be 25 degrees on excitation and 15 degrees on emission. "Power to vial" refers to the total optical power making it into the vial that is available for excitation of fluorescent probes. "Moving carriage baseline," as used herein, refers to a baseline used for comparing different configurations of the optical system. Example data shown in the present disclosure are baselined against the design without a wheel-shaped component, for example, as shown in FIGS. 7 and 8. Using the parameters described herein, the properties of different configurations can be tested by excitation simulation. For example, an optical system can have a power to vial value of about 2%, 3%, 4%, 5%, 6%, 7%, 8%, 9%, 10% or more. The optical system can be 1 fold, 1.5 fold, 2 fold, 2.5 fold, 3 fold, 3.5 fold, 4 fold, 5 fold, 6 fold, 7 fold, 8 fold, 9 fold, 10 fold, 15 fold, 20 fold, or more efficient than the moving carriage baseline. The SNR of the optical system can be at least 1,000, 1,500, 2,000, 2,500, 3,000, 3,500, 4,000, 5,000 or more. In some case, the SNR of the optical system can be at least 100, 150, 200, 250, 300, 350, 400, 450, 500 or more. For example, a configuration shown in FIG. 16 have a power to vial value of 5.8%, 2 to 20 fold more efficient than the moving carriage baseline, and have a SNR value of about 2,000. FIGS. 20A-C and 21A-C show example simulation results of the optical system. FIG. 20A shows the power to vial value of 5.8% of the tested carriage having a fold mirror configuration. FIG. 20B shows the total power on filter of 5.9%. FIG. 20C shows the SNR calculated at 25 degrees to be 2112. FIG. 21A shows the power to detector of 0.31% of the tested carriage having a fold mirror configuration. FIG. 21B shows the power on filter of 0.33%. FIG. 21C shows the SNR calculated at 15 degrees to be 3067.

Figure 10:
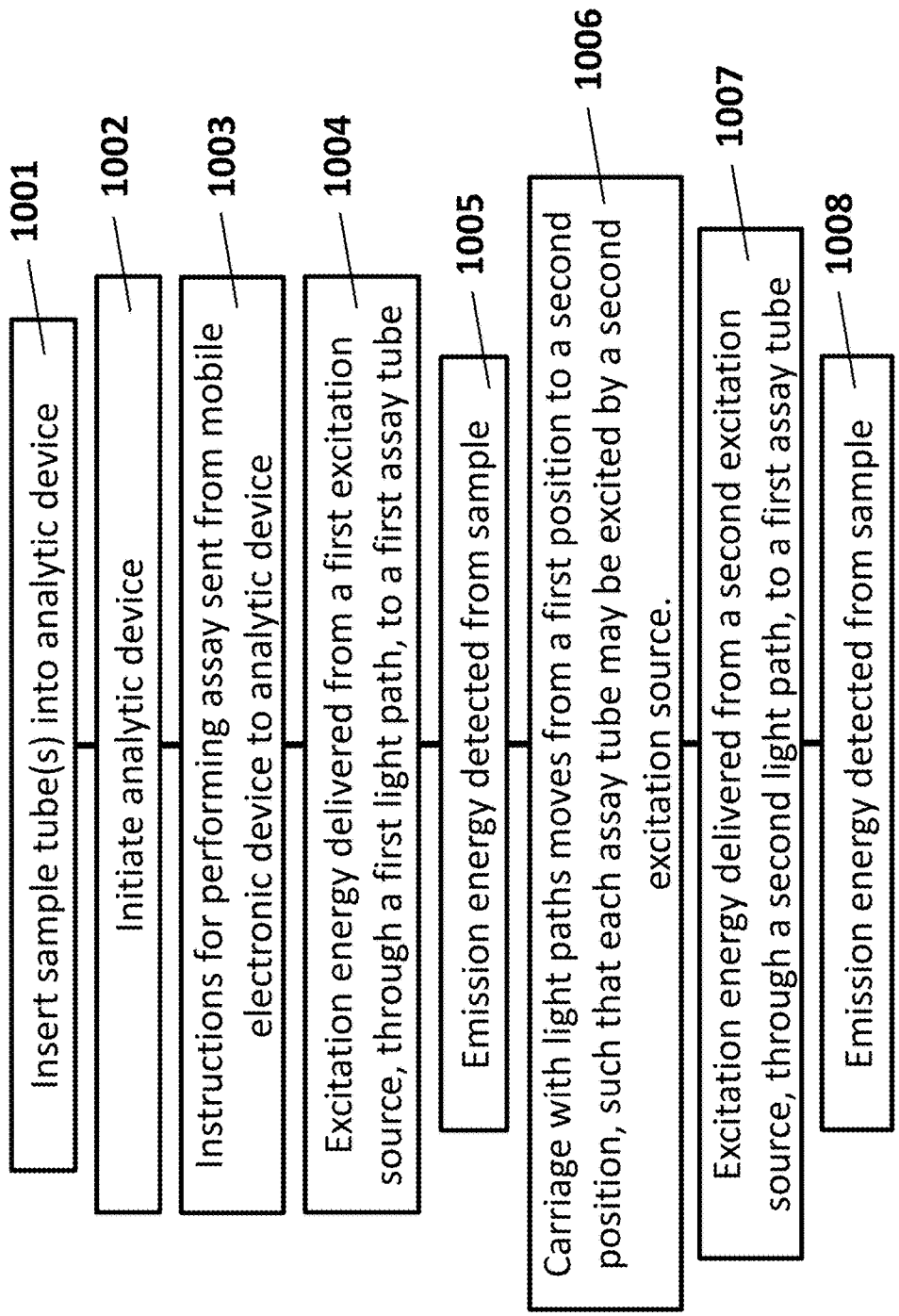
FIG. 10 shows a flow chart of an example method of analyzing a biological sample using a portable analytic device of the present disclosure, such as the portable analytic device of FIG. 2A.

FIG. 10 shows an example process flow for the analytic device of FIGS. 1A-1B. In a first operation 1001, lid 101 of housing 100 is opened, and a user inserts one or more assay tubes each containing a sample into the analytic device. In a second operation 1002, the user initiates the analytic device by pressing power button 103 located on housing 100. In a third operation 1003, the user provides instructions for performing an amplification reaction (e.g., a thermal cycling assay). The instructions may be provided using an application on a mobile electronic device (e.g., which may be physically detached from the analytic device, integrated into the analytic device, or removably disposed in or on the analytic device, for example in a housing or groove of the analytic device). Instructions provided to the application may then be communicated to the analytic device (e.g., via a wireless connection, as described herein). In a fourth operation 1004, the analytic device is initiated, and an excitation energy is delivered from excitation source 611, through excitation filter 610, through light path 502, to a first assay tube. In a fifth operation 1005, emission energy from the sample in the first assay tube is delivered from the sample through emission filter 503 to detector 801. In a sixth operation 1006, a moving carriage comprising excitation source 611, excitation filter 610, and emission filter 503 may move to a second position (e.g., aligning light path 502 with a second assay tube). In a seventh operation 1007, excitation energy is delivered from a second excitation source, through a second excitation filter, through a second light path, to the first assay tube. In an eighth operation 1008, emission energy from the sample in the first assay tube is delivered from the sample through a second emission filter and to detector 801.

Mixing

An analytic device may be configured to mix a sample within an assay tube. In some cases, reagents may not dissolve well when aqueous analyte liquid fills assay tubes (or assay cuvettes) containing lyophilized reagents. The reagents may dissolve rapidly in the incoming solution; however, they may not mix as the tube fills. After filling the assay tube, the solution can be divided into a dense concentrated solution near the bottom and less concentrated or diluted solution near the top of the tube. Poorly mixed reagents can yield poor reaction efficiency and solid precipitates which can interfere with optical signals. Diffusion alone may not achieve homogeneity or take long to achieve homogeneity. Provided herein are devices or methods comprising a mechanical mixing. For example, a bead (e.g., a stainless ferrous bead of various diameter such as ~1 mm diameter) can be added to the tube with dry reagents during assembly and packaging. During operation, the bead can be subjected to motion through the unmixed solution by magnetic fields generated by moving magnets exterior to the tube. These magnets can be fastened to an optical carriage which moves in linear fashion cycling from side to side during optical sampling. The mixing motion can be accomplished by using a linear array of magnets (e.g., rare earth magnets) of predetermined size, spacing and orientation. Magnets can be spaced with identical pitch of tubes and in an array in parallel to the tube array. Magnetic axes can be normal to the axes of the tubes and move in a plane across the upper portion of fluid level. Magnetic polarities can be aligned, yielding a zero field in the vertical plane dividing neighboring magnets. When magnets are moved along the linear array the pull force on each bead can increase as one magnet approaches and decrease as another recedes. When passing through the zero field zone between magnets, the bead can drop under force of gravity. The cycle can repeat in this manner in one direction of carriage movement and again when the direction of the optical carriage reverses. The bead path may be linear or arcing. In some cases, the bead path may be arcing.

The methods provided herein can use mechanical motion of a bead (e.g., a steel bead or various other materials) to mix a solution of solubilized reagent with a lower density analyte solution. The mixing operation can occur during the fill stage of the assay tube to mitigate density or chemical gradients. In some cases, mixing can occur throughout the duration of the test or assay since actuating magnets are fixed to the optical carriage. The mixing methods can be used to mix the analyte graded by temperature. Since heating occurs at the external heating block, a temperature gradient can be generated during thermal cycling, which can lead to inefficient PCR. In some cases, mixing of the assay mixture can occur during the thermal cycling. For example, mixing can occur during heating, during cooling or during optical sampling. Mixing of the assay mixture during the thermal cycling (e.g., during heat and cool ramping on either side of optical sampling or even during optical sampling) can homogenize the temperature throughout the assay tube, which can lead to increased PCR efficiency.

Figure 23:
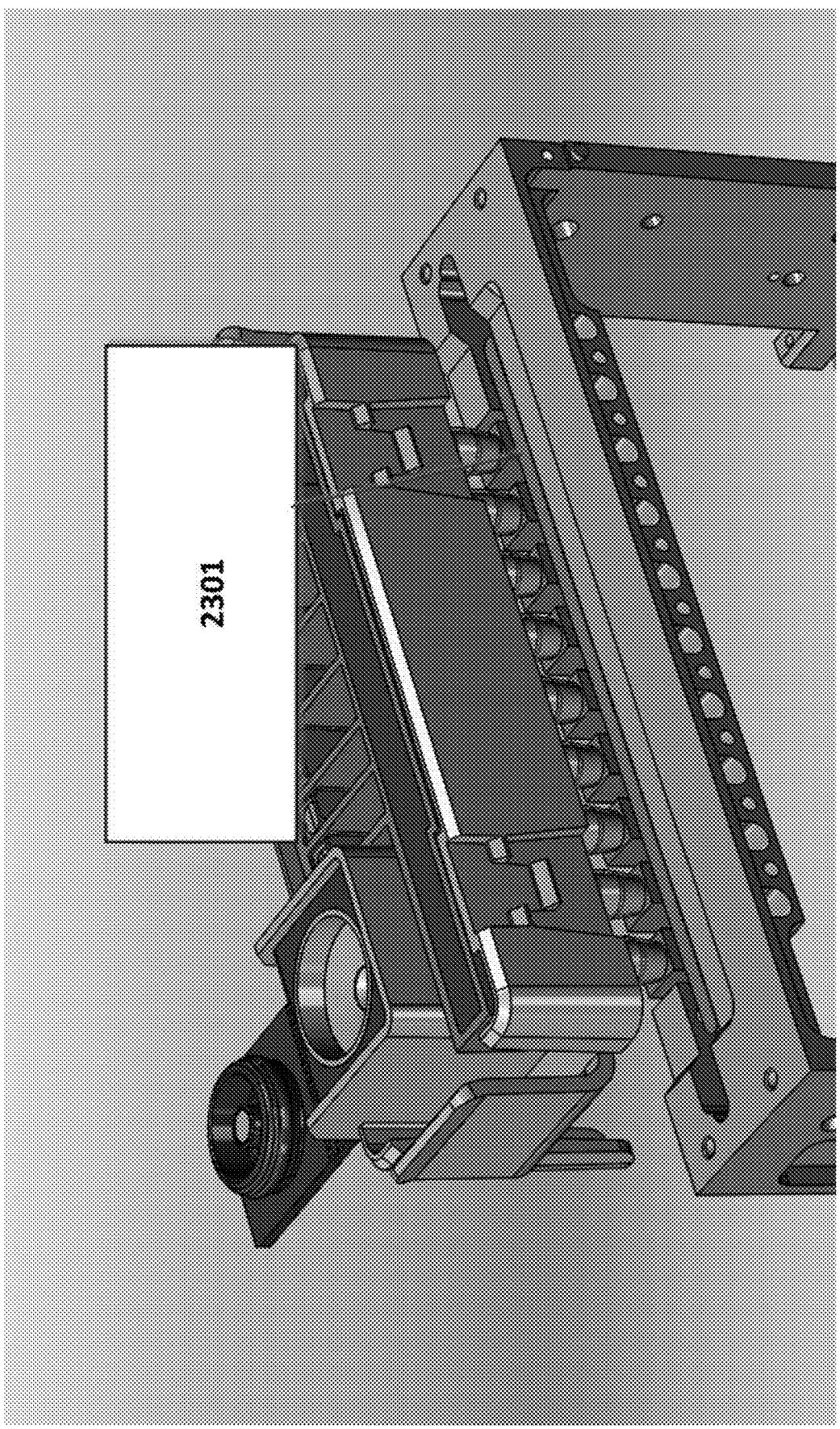
FIG. 23 shows a view of the bar in place inside the portable analytic device's housing.
Figure 24:
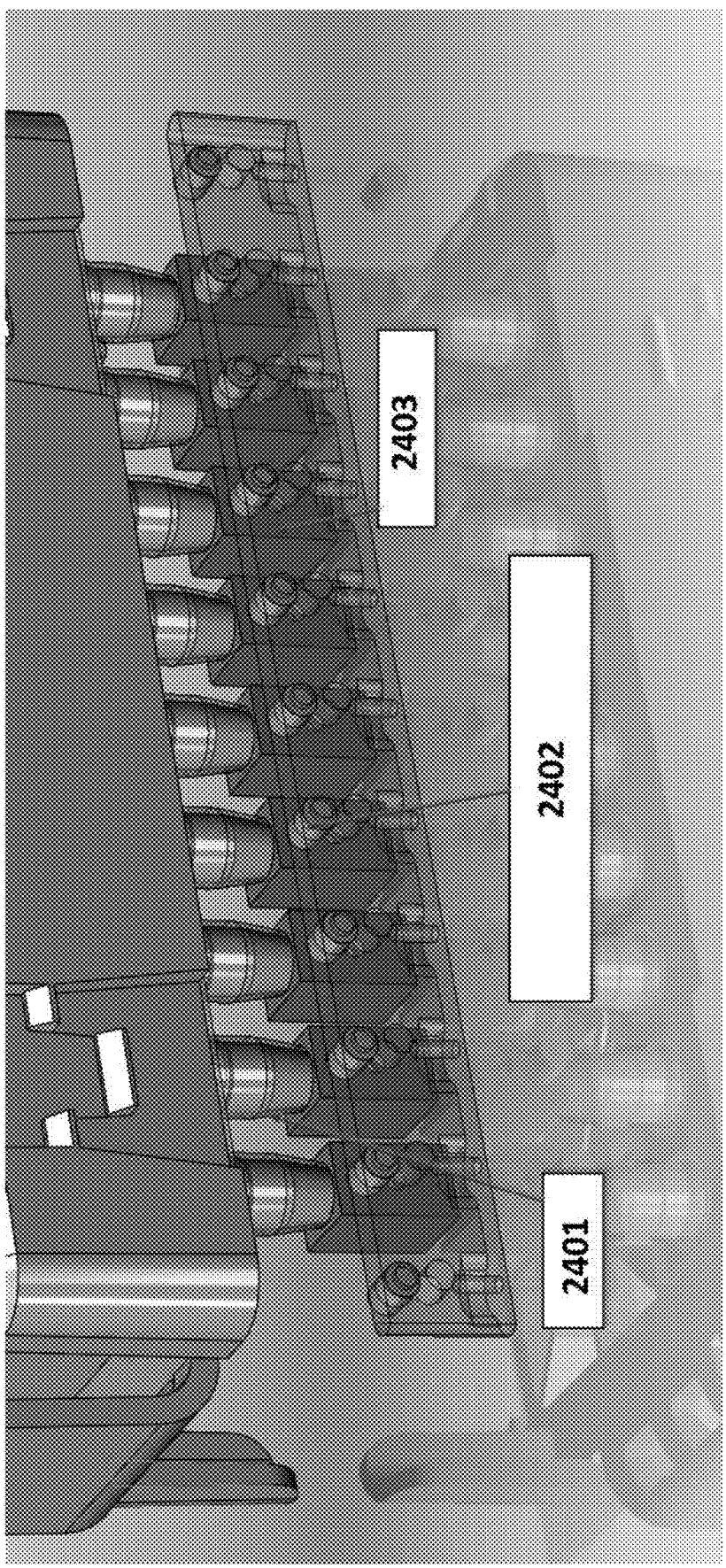
FIG. 24 shows a zoom-in view of the bar in position next to the blocks and assay tubes.

As shown in FIG. 23, an analytic device may comprise a bar 2301 within its housing. A bar can be of any appropriate material and size for inclusion within the device. The device may be constructed of metal. Alternatively, the device may be constructed of plastic. As shown in FIG. 24, a bar may comprise one or more magnets 2402 for the purposes of mixing a sample within an assay tube 2401 contained in a recess in a block 2403. For example, a bar may comprise 1, 2, 3, 4, 5, 6, 7, 8, 9, 10, 11, 12, 13, 14, 15, 16, 17, 18, 19, 20, or more magnets. The magnets may be permanent magnets. The magnets may be electromagnets. The magnets may be constructed of any appropriate ferromagnetic or paramagnetic material. For example, the magnets may be constructed from iron, cobalt, nickel, or an alloy thereof. Alternatively, the magnets may be constructed from rare-earth elements. For example, the magnets may be constructed from cerium, dysprosium, erbium, europium, gadolinium, holmium, lanthanum, lutetium, neodymium, praseodymium, promethium, samarium, scandium, terbium, thulium, ytterbium, yttrium, or an alloy thereof. The magnets may be of any size and shape appropriate to provide mixing to a sample contained within an assay tube. For example, the magnets may be circular. Alternatively, the magnets may be rectangular.

Figure 25:
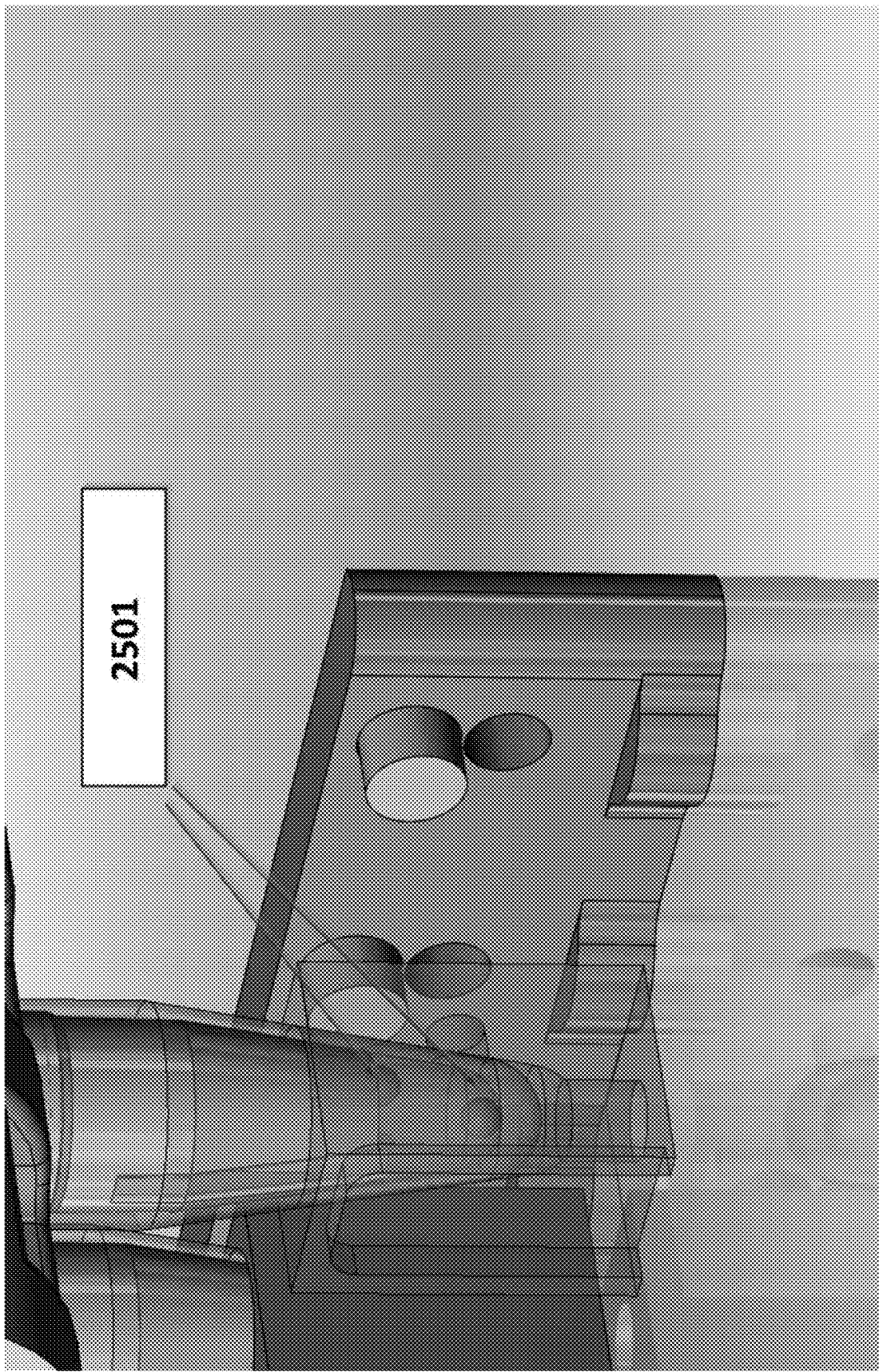
FIG. 25 shows a zoom-in view of the magnet-comprising bar and a magnetic bead inside an assay tube contained within a recess in a block.

As shown in FIG. 25, an assay tube may comprise a biological sample and a magnetic bead 2501. A magnetic bead may be constructed of any appropriate magnetic material. For example, a magnetic bead may be constructed from any ferromagnetic or paramagnetic material. For example, a magnetic bead may be constructed from iron, cobalt, nickel, or an alloy thereof. Alternatively, the magnetic beads may be constructed from rare-earth elements. For example, the magnetic beads may be constructed from cerium, dysprosium, erbium, europium, gadolinium, holmium, lanthanum, lutetium, neodymium, praseodymium, promethium, samarium, scandium, terbium, thulium, ytterbium, yttrium, or an alloy thereof. A magnetic bead may be constructed of more than one material. A magnetic bead may be of any appropriate size and shape to be contained within an assay tube. For example, a magnetic bead may be spherical. The magnetic bead can be at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 or more millimeters (mm) in size (e.g., diameter).

Figure 26:
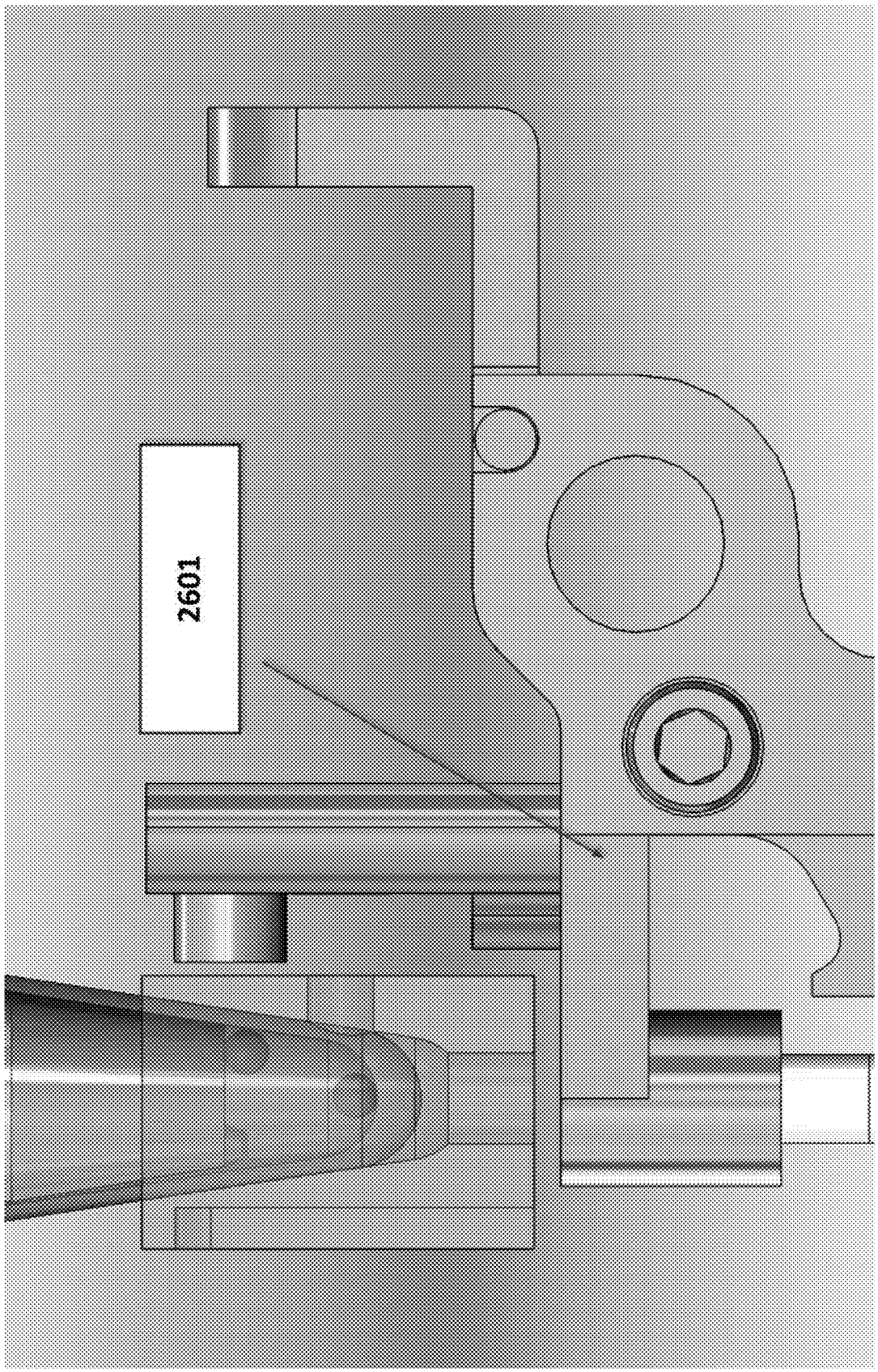
FIG. 26 shows a side view of an example of a movable carriage comprising optical elements and a magnet-comprising bar.

A bar and a block contained within an analytic device may be configured to undergo motion such that a magnet on the bar and an assay tube contained within the block move relative to one another. The device may be configured such that the bar undergoes motion. The device may be configured such that the bar undergoes motion while the block is stationary. The device may be configured such that the bar undergoes linear motion. For example, the bar can undergo linear motion from side to side during optical sampling. The device may be configured such that the bar undergoes circular motion. The block may be configured to undergo motion. The block may be configured to undergo motion while the bar is stationary. The block may be configured to undergo linear motion. The bar and the block may both be configured to undergo motion. The bar and/or the block may be configured to undergo motion in more than one direction. The bar and/or the block may be configured to undergo motion in more than one dimension at once. For example, the bar may be configured to simultaneously undergo horizontal and vertical motion. The bar and the block may both be configured to undergo linear motion. The bar and the block may both be configured to undergo circular motion. The bar may be unattached to other mobile components of the device, with the exception of the component intended to provide motion to the bar. Alternatively, the bar may be coupled to other components of the device configured to move. As shown in FIG. 26, the bar may be mounted to a movable carriage 2601 that also comprises an optical system.

The motion undergone by the bar and/or the block may subject the magnetic bead to motion within the assay tube, thereby mixing the sample contained within the assay tube. The movement of the magnetic bead within the assay tube may be at any speed and in any pattern appropriate to mix the sample. For example, the magnetic bead may move in a linear, circular, or elliptical pattern within the assay tube to subject the sample to mixing. The magnetic bead may move in one or both directions. A magnetic bead can be made to undergo motion due to the effect of any number of magnets mounted to the bar. For example, a single magnetic bead in a single assay tube may be made to undergo motion by 1, 2, 3, 4, 5, 6, 7, 8, 9, 10, 11, 12, 13, 14, 15, 16, 17, 18, 19, 20, or more magnets mounted to the bar.

Figure 27A:
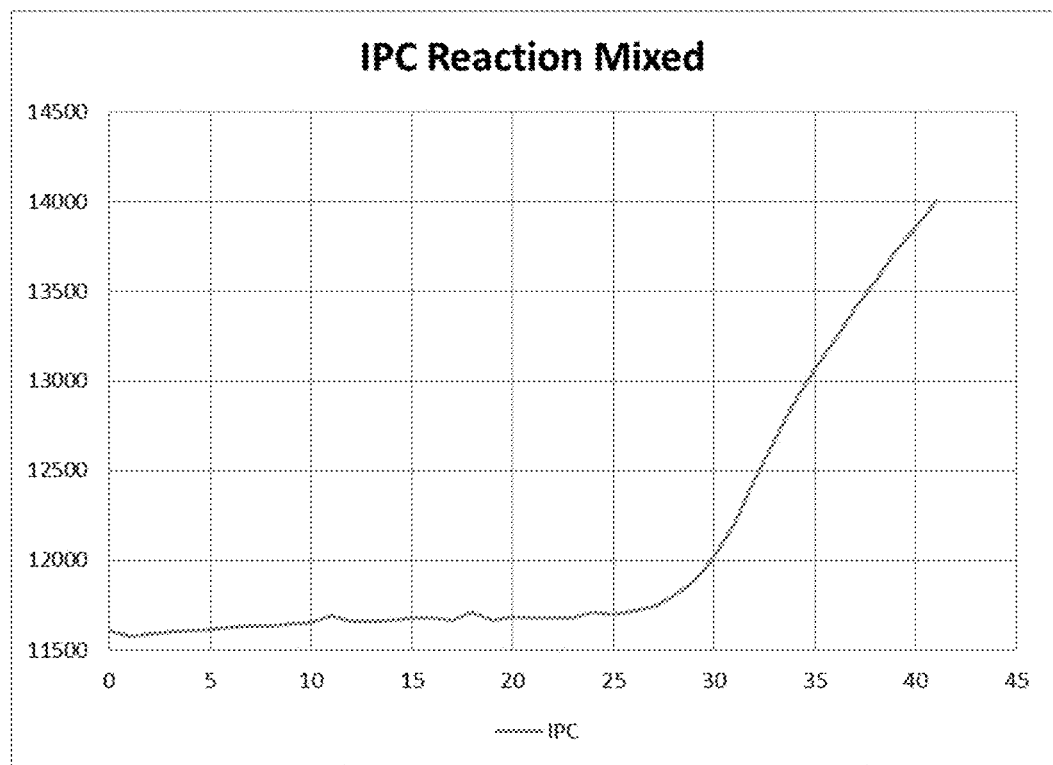
FIG. 27A shows experimental data of nucleic acid amplification using a portable analytic device of the present disclosure. The reaction mixture was subjected to mixing by the mixing methods described herein.
Figure 27B:
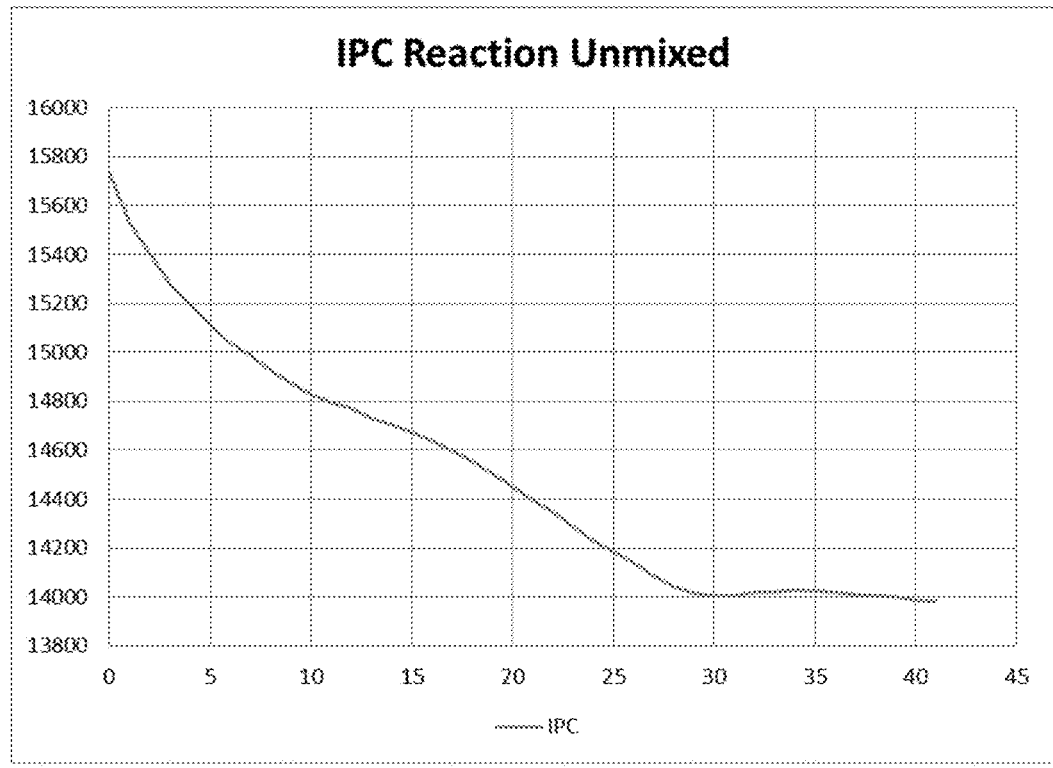
FIG. 27B shows experimental data of nucleic acid amplification using a portable analytic device of the present disclosure. The reaction mixture was the same as the mixture in FIG. 27A except that the mixture was not subjected to mixing by the mixing methods described herein.

The mixing methods provided herein can provide advantages or benefits to the mixed samples over the unmixed samples. For example, the mixing methods can maintain the reaction mixture to be homogenous to prevent signal drift (e.g., decreasing of signal). In some cases, the signal generated in the mixed samples can remain close to the background level signal before the amplification begins. In some cases, no signal drift may be observed in the mixed samples. The beginning of the amplification can be easily identified when the reaction mixture is mixed. For another example, the reaction can proceed more efficiently in the mixed sample than the reaction in the unmixed sample. In some cases, sensitivity can be increased when the reaction mixture or the sample is mixed. FIG. 27A shows experimental data of nucleic acid amplification using a portable analytic device of the present disclosure. The reaction mixture was subjected to mixing by the mixing methods described herein. The reaction mixture contained magnetic beads and was mixed prior to or during thermocycling by the bar within the analytic device described herein. In the mixed sample, the reaction was homogenous and thus the signal remained flat (e.g., close to the background level) throughout thermocycling, until amplification began, which makes it easy to identify when amplification occurs. No signal drift was observed when the reaction mixture was mixed. The reaction proceeded efficiently and increased sensitivity was observed. FIG. 27B shows experimental data of nucleic acid amplification using a portable analytic device of the present disclosure. As a control, the reaction mixture was the same as the mixture in FIG. 27A except that the mixture was not subjected to mixing by the mixing methods described herein. In the unmixed reaction, the reagents were concentrated at the bottom of the reaction tube near the detector and thus the signal started bright. As thermocycling proceeded, the reaction mixed through diffusion thus the signal started to become dimmer. This signal drift obfuscated the reaction signal, making it more difficult to identify amplification. In addition to the signal drift, the reaction proceeded less efficiently than the mixed sample.

Samples

A variety of samples (e.g., biological samples) may be analyzed. A sample may be obtained invasively (e.g., tissue biopsy) or non-invasively (e.g., venipuncture). The sample may be an environmental sample. The sample may be a water sample (e.g., a water sample obtained from a lake, stream, river, estuary, bay, or ocean). The sample may be a soil sample. The sample may be a tissue or fluid sample from a subject, such as saliva, semen, blood (e.g., whole blood), serum, synovial fluid, tear, urine, or plasma. The sample may be a tissue sample, such as a skin sample or tumor sample. The sample may be obtained from a portion of an organ of a subject. The sample may be a cellular sample. The sample may be a cell-free sample (e.g., a plasma sample comprising cell-free analytes or nucleic acids). A sample may be a solid sample or a liquid sample. A sample may be a biological sample or a non-biological sample. A sample may comprise an in-vitro sample or an ex-vivo sample. Non-limiting examples of a sample include an amniotic fluid, bile, bacterial sample, breast milk, buffy coat, cells, cerebrospinal fluid, chromatin DNA, ejaculate, nucleic acids, plant-derived materials, RNA, saliva, semen, blood, serum, soil, synovial fluid, tears, tissue, urine, water, whole blood or plasma, and/or any combination and/or any fraction thereof. In one example, the sample may be a plasma sample that may comprise DNA. In another example, the sample may comprise a cell sample that may comprise cell-free DNA.

A sample may be a mammalian sample. For example, a sample may be a human sample. Alternatively, a sample may be a non-human animal sample. Non-limiting examples of a non-human sample include a cat sample, a dog sample, a goat sample, a guinea pig sample, a hamster sample, a mouse sample, a pig sample, a non-human primate sample (e.g., a gorilla sample, an ape sample, an orangutan sample, a lemur sample, or a baboon sample), a rat sample, a sheep sample, a cow sample, and a zebrafish sample.

The portable analytic devices and methods disclosed herein may be useful for analyzing nucleic acids (e.g., circulating and/or cell-free DNA fragments). Nucleic acids may be derived from eukaryotic cells, prokaryotic cells, or non-cellular sources (e.g., viral particles). A nucleic acid may refer to a substance whose molecules consist of many nucleotides linked in a long chain. Non-limiting examples of the nucleic acid include an artificial nucleic acid analog (e.g., a peptide nucleic acid, a morpholino oligomer, a locked nucleic acid, a glycol nucleic acid, or a threose nucleic acid), chromatin, niRNA, cDNA, DNA, single stranded DNA, double stranded DNA, genomic DNA, plasmid DNA, or RNA. A nucleic acid may be double stranded or single stranded. A sample may comprise a nucleic acid that may be intracellular. Alternatively, a sample may comprise a nucleic acid that may be extracellular (e.g., cell-free). A sample may comprise a nucleic acid (e.g., chromatin) that may be fragmented.

Assays

An assay may comprise nucleic acid amplification. For example, any type of nucleic acid amplification reaction may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, asymmetric amplification, rolling circle amplification, and multiple displacement amplification (MDA). The amplified product may be DNA. In cases where a target RNA is amplified, DNA may be obtained by reverse transcription of the RNA and subsequent amplification of the DNA may be used to generate an amplified DNA product. The amplified DNA product may be indicative of the presence of the target RNA in the biological sample. In cases where DNA is amplified, various DNA amplification methods may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). DNA amplification may be linear. Alternatively, DNA amplification may be exponential. DNA amplification may be achieved with nested PCR, which may improve sensitivity of detecting amplified DNA products. Nucleic acid amplification may be isothermal. Non-limiting examples of isothermal nucleic acid amplification methods include helicase-dependent amplification, nicking enzyme amplification, recombinase polymerase amplification, loop-mediated isothermal amplification, and nucleic acid sequence based amplification.

Nucleic acid amplification reactions may be conducted in assay tubes in parallel. Nucleic acid amplification reactions may be conducted, for example, by including reagents necessary for each nucleic acid amplification reaction in a reaction vessel to obtain a reaction mixture and subjecting the reaction mixture to conditions necessary for each nucleic amplification reaction. Reverse transcription amplification and DNA amplification may be performed sequentially, such as, for example, performing reverse transcription amplification on RNA to generate complementary DNA (cDNA), and subsequently subjecting the cDNA to DNA amplification (e.g., PCR) to amplify the cDNA.

A nucleic acid sample may be amplified using reagents directed to a given target, such as, for example, a primer having sequence complementarity with a target sequence. After multiple heating and cooling cycles, any amplification products may be detected optically, such as using fluorophores. Fluorophore-labeled primers or hybridization probes and/or fluorescent dyes that bind to DNA may be excited, and an emitted fluorescence detected. Detection may comprise analyzing fluorescence emission from a dye and calculating the ratio of fluorophore emission to dye emission.

A primer may comprise a fluorophore and a quencher. In some cases, a tertiary structure of an unbound primer may be such that a quencher may be in close enough proximity to a fluorophore to prevent excitation of the fluorophore and/or the detection of an emission signal from the fluorophore.

In one example, a fluorescent DNA dye, such as SYBR Green I, may be added to a mixture containing a target nucleic acid and at least one amplification primer. In other examples, an amplification primer may be a linear single-stranded oligonucleotide that is extendable by a DNA polymerase and that is labeled with an excitable fluorophore. Upon performing an amplification reaction, such as, e.g., PCR, that includes annealing and extending the labeled primer, the fluorophore may be excited and a resultant emission detected during the amplification reaction (e.g., real-time detection) or following completion of the amplification reaction (e.g., an end-point detection at the conclusion of the amplification reaction or during a subsequent thermal analysis (melting curve)). Unincorporated primers may not fluoresce.

A wide range of fluorophores and/or dyes may be used in primers according to the present disclosure. Available fluorophores include coumarin; fluorescein; tetrachlorofluorescein; hexachlorofluorescein; Lucifer yellow; rhodamine; BODIPY; tetramethylrhodamine; Cy3; Cy5; Cy7; eosine; Texas red; SYBR Green I; SYBR Gold; 5-FAM (also called 5-carboxyfluorescein; also called Spiro(isobenzofuran-1 (3H), 9'-(9H) xanthene)-5-carboxylic acid, 3 ', 6'-dihydroxy-3-oxo-6-carboxyfluorescein); 5-Hexachloro-Fluorescein ([4,7,2',4',5', 7'-hexachloro-(3',6'-dipivaloyl-fluoresceinyl)-6-carboxylic acid]); 6-Hexachloro-Fluorescein ([4,7,2',4',5', 7'-hexachloro-(3',6'-dipivaloylfluoresceinyl)-5-carboxylic acid]); 5-Tetrachloro-Fluorescein ([4,7,2',7'-tetra-chloro-(3', 6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS(5-((((2-iodoacetyl)amino)ethyl)amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); BODIPY FL (2,6-dibromo-4,4-difluoro-5,7-dimethyl-4-bora-3a,4a-diaza-s-indacene-3-proprionic acid); Quasar-670 (Bioreseach Technologies); CalOrange (Bioresearch Technologies); and Rox as well as suitable derivatives thereof. Combination fluorophores such as fluorescein-rhodamine dimers may also be suitable. Fluorophores may be chosen to absorb and emit in the visible spectrum or outside the visible spectrum, such as in the ultraviolet or infrared ranges. Suitable quenchers may also include DABCYL and variants thereof, such as DABSYL, DABMI and Methyl Red. Fluorophores may also be used as quenchers, because they tend to quench fluorescence when touching certain other fluorophores. Preferred quenchers may be chromophores such as DABCYL or malachite green, or fluorophores that may not fluoresce in the detection range when the probe is in the open conformation.

Allele-discriminating probes useful according to the invention also include probes that bind less effectively to a target-like sequence, as compared to a target sequence. The change in the level of fluorescence in the presence or absence of a target sequence compared to the change in the level of fluorescence in the presence or absence of a target-like sequence may provide a measure of the effectiveness of binding of a probe to a target or target-like sequence.

DNA generated from reverse transcription of the RNA may be amplified to generate an amplified DNA product. Any suitable number of nucleic acid amplification reactions may be conducted. In some cases, at least 1, 2, 3, 4, 5, 6, 7, 8, 9, 10, 11, 12, 13, 14, 15, 16, 17, 18, 19, 20, or more nucleic acid amplification reactions are conducted.

For example, a target nucleic acid (e.g., target RNA, target DNA) may be extracted or released from a biological sample during heating phases of nucleic acid amplification. In the case of a target RNA, for example, the biological sample comprising the target RNA may be heated and the target RNA released from the biological sample. The released target RNA may begin reverse transcription (via reverse transcription amplification) to produce complementary DNA. The complementary DNA may then be amplified.

Primer sets directed to a target nucleic acid may be utilized to conduct nucleic acid amplification reaction. Primer sets may comprise one or more primers. For example, a primer set may comprise at least 1, 2, 3, 4, 5, 6, 7, 8, 9, 10, or more primers. A primer set may comprise primers directed to different amplified products or different nucleic acid amplification reactions. For example, a primer set may comprise a first primer necessary to generate a first strand of nucleic acid product that is complementary to at least a portion of the target nucleic acid and a second primer complementary to the nucleic acid strand product necessary to generate a second strand of nucleic acid product that is complementary to at least a portion of the first strand of nucleic acid product.

In cases in which a plurality of assay tubes is used, the plurality of assay tube may include the same primers or primer sets, or different primers or primer sets. Each assay tube may be directed to a different target, or at least a subset of the assay tubes may be directed to the same target.

For example, a primer set may be directed to a target RNA. The primer set may comprise a first primer that may be used to generate a first strand of nucleic acid product that is complementary to at least a portion the target RNA. In the case of a reverse transcription reaction, the first strand of nucleic acid product may be DNA. The primer set may also comprise a second primer that may be used to generate a second strand of nucleic acid product that is complementary to at least a portion of the first strand of nucleic acid product. In the case of a reverse transcription reaction conducted with DNA amplification, the second strand of nucleic acid product may be a strand of nucleic acid (e.g., DNA) product that is complementary to a strand of DNA generated from an RNA template.

Any suitable number of primer sets may be used. For example, at least about 1, 2, 3, 4, 5, 6, 7, 8, 9, 10, or more primer sets may be used. Where multiple primer sets are used, one or more primer sets may each correspond to a particular nucleic acid amplification reaction or amplified product.

A DNA polymerase may also be used. Any suitable DNA polymerase may be used, including commercially available DNA polymerases. A DNA polymerase may refer to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products, and derivatives thereof. A "hot start" polymerase may be used, e.g., in an amplification reaction. For certain "hot start" polymerases, a denaturation step at about 94° C.-95° C. for about 2 minutes to 10 minutes may be required, which may change the thermal profile based on different polymerases.

Figure 12A:
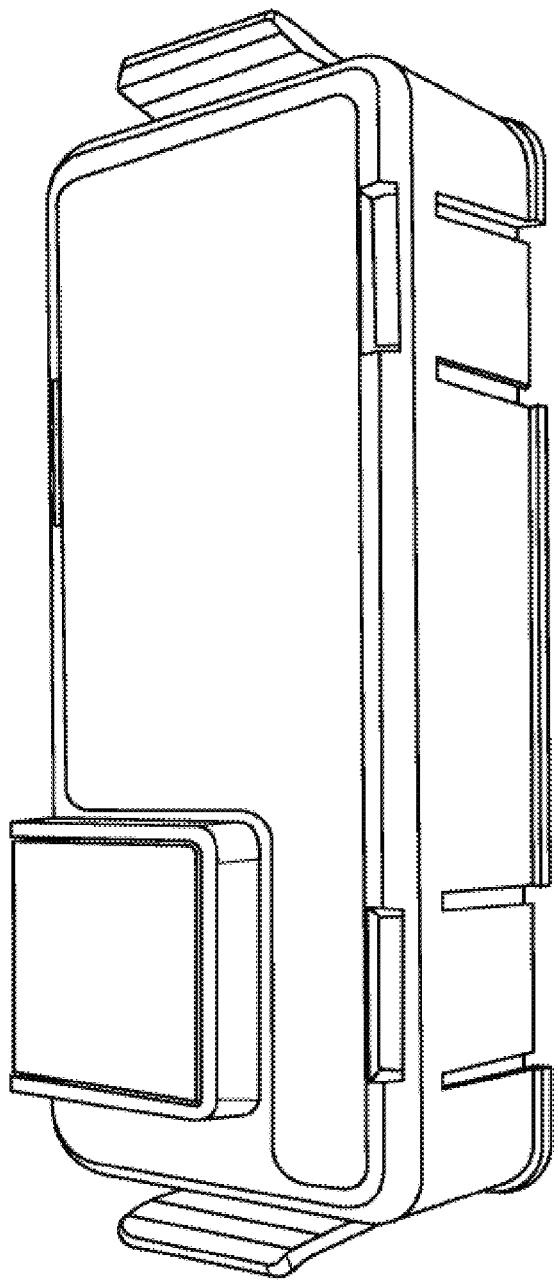
FIG. 12A shows an example cartridge that can be inserted into the analytic device for sample testing. The cartridge can contain one or more reagents to be used for nucleic acid amplification (e.g., polymerase chain reaction (PCR)).
Figure 12B:
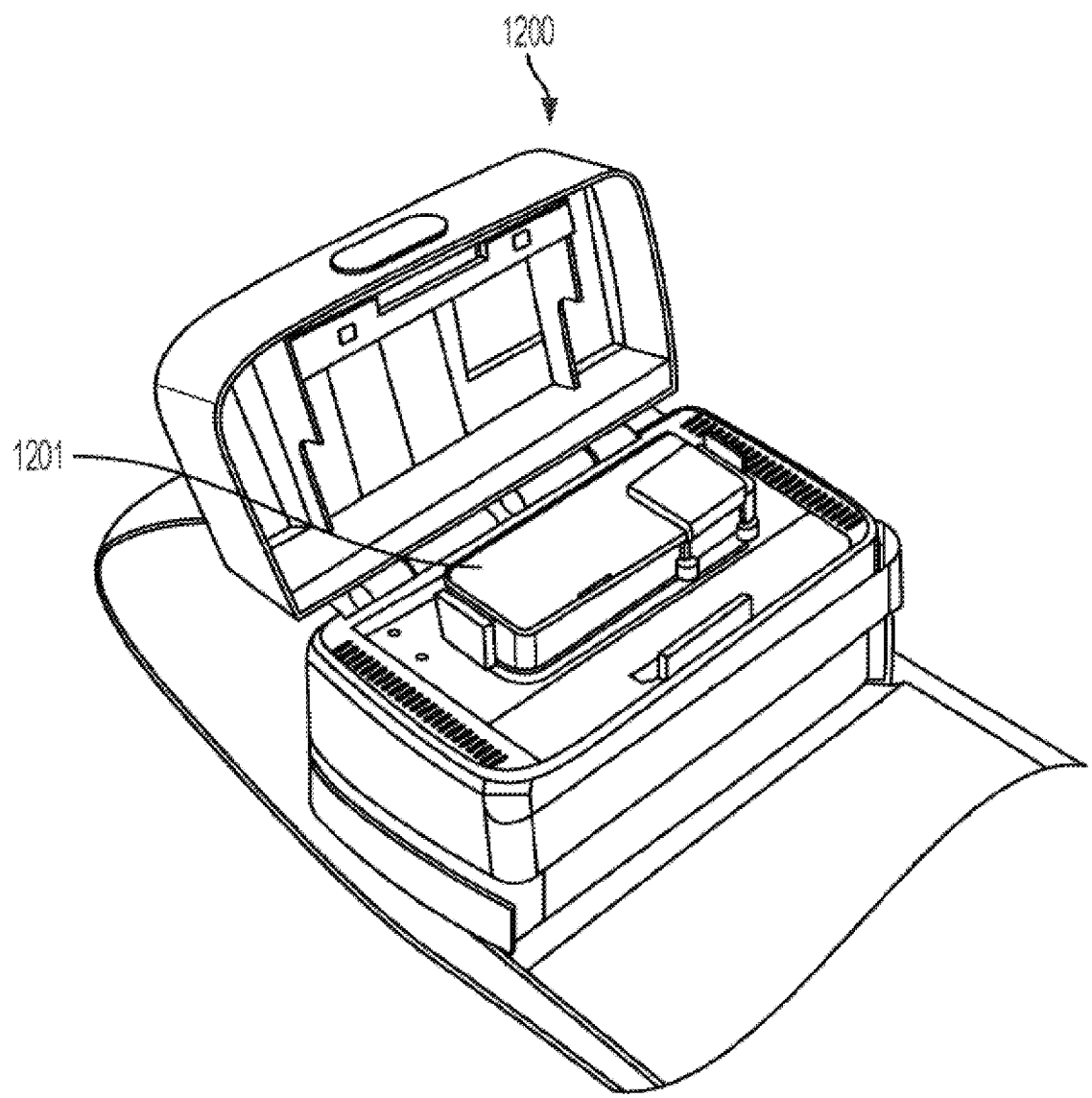
FIG. 12B shows an example cartridge inserted into the housing of the analytic device.

The reagents used for assays (e.g., thermocycling reactions or nucleic acid amplifications) can be provided in a reagent cartridge. The reagent cartridge can be premixed or prepacked. The reagent cartridge can be prepacked and ready for use. The reagent cartridge can be designed for different targets, for example, by containing primers specific for a given target or given targets. For example, the reagent cartridge can be designed for targeting microorganisms that cause a disease. In some embodiments, the reagent cartridge is designed for targeting nucleic acids from one or more microorganisms that cause fever or flu. In some embodiments, the reagent cartridge is designed for targeting nucleic acids from one or more viruses that cause fever or flu. In some embodiments, the reagent cartridge is designed for targeting nucleic acids from one or more microorganisms that cause an infectious disease. In some embodiments, the reagent cartridge is designed for targeting one or more microorganisms present in a sample. In some embodiments, the reagent cartridge is designed for targeting one or more microorganisms present in an environmental sample. The reagent cartridge can comprise a chamber for sample loading. An example cartridge is shown in FIG. 12A. The example cartridge 1201 can be inserted into the housing 1200 of the analytic device, for example, as shown in FIG. 12B.

The reagent cartridge can be stable and have a long shelf life. For example, the reagent cartridge can be stable at ambient condition or have a shelf life of at least about 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, or 30 months. For another example, the reagent cartridge can be stable at ambient condition or have a shelf life of at least 1 year, 1.5 years, 2 years, 2.5 years, 3 years, 4 years, 5 years, or longer.

In some cases, the reagent used for assays can be divided into two parts, a dry part and a wet (e.g., liquid) part. The dry part can be provided in a reagent cartridge as described herein. The wet part can be provided in the portable analytic device during an assay. The dry part and the wet part can be mixed in the portable analytic device when performing an assay.

In some embodiments, the wet part can be provided in a reagent cartridge as described herein. The dry part can be provided in the portable analytic device during an assay. The dry part and the wet part can be mixed in the portable analytic device when performing an assay.

In some embodiments, both the dry part and the wet part can be provided in a reagent cartridge without contacting or mixing with each other. In some embodiments, both the dry part and the part can be provided in separate reagent cartridges.

In some embodiments, the dry part and the wet part can be premixed before inserting into the portable analytic device. In some embodiments, the dry part and the wet part can be inserted into the portable analytic device and then mixed in the portable analytic device.

When a wet reagent is provided in a reagent cartridge, the reagent cartridge can be sealed. In some embodiments, the reagent cartridge containing the wet reagent can be sealed by laser welding. Other methods to seal the reagent cartridge include, but are not limited to, using foil, membrane, film, or valve.

Using the portable analytic device and reagent described in the present disclosure, the assay can be performed in various conditions. For example, the assay can be performed in various vibration conditions, dust levels, humidity levels, or altitudes. In some embodiments, the assay can be performed at normal ambient condition. For example, the normal ambient condition may have a temperature of about 25° C. and a pressure of about 100 kilopascal (kPa). In some other embodiments, the assay can be performed in a condition deviated from a normal ambient condition. In some cases, the assay can be performed at a pressure of at least 10 kPa, 20 kPa, 30 kPa, 40 kPa, 50 kPa, 60 kPa, 70 kPa, 80 kPa, 90 kPa, 100 kPa, 105 kPa, 110 kPa, 120 kPa, 130 kPa, or more. In some cases, the assay can be performed at a pressure of at most 70 kPa, 60 kPa, 50 kPa, 40 kPa, 30 kPa, 20 kPa, or 10 kPa. In some cases, the assay can be performed at an altitude above sea level. The altitude above sea level can be at least 500 feet, 1000 feet, 1500 feet, 2000 feet, 2500 feet, 3000 feet, 3500 feet, 4000 feet, 4500 feet, 5000 feet, 6000 feet, 7000 feet, 8000 feet, 9000 feet, 10000 feet, 15000 feet, 20000 feet, 30000 feet, 40000 feet, 50000 feet, or more. The assay described herein may be performed in space.

The assay described herein can be performed at various humidity levels. As used herein, absolute humidity (units are grams of water vapor per cubic meter volume of air) is a measure of the actual amount of water vapor in the air, regardless of the air's temperature. The higher the amount of water vapor, the higher the absolute humidity. For example, a maximum of about 30 grams of water vapor can exist in a cubic meter volume of air with a temperature of about 85° F. As used herein, relative humidity, expressed as a percent, is a measure of the amount of water vapor that air is holding compared to the amount it can hold at a specific temperature. Warm air can possess more water vapor (moisture) than cold air. For example, a relative humidity of 50% means that the air holds on that day (at a specific temperature) about 50% of the water needed for the air to be saturated. Saturated air has a relative humidity of 100%. In some embodiments, the assay can be performed at a humidity level with a relative humidity of at least 10%, 20%, 30%, 40%, 50%, 60%, 80%, 70%, 90%, 95 %, 98%, or more.

Figure 22A:
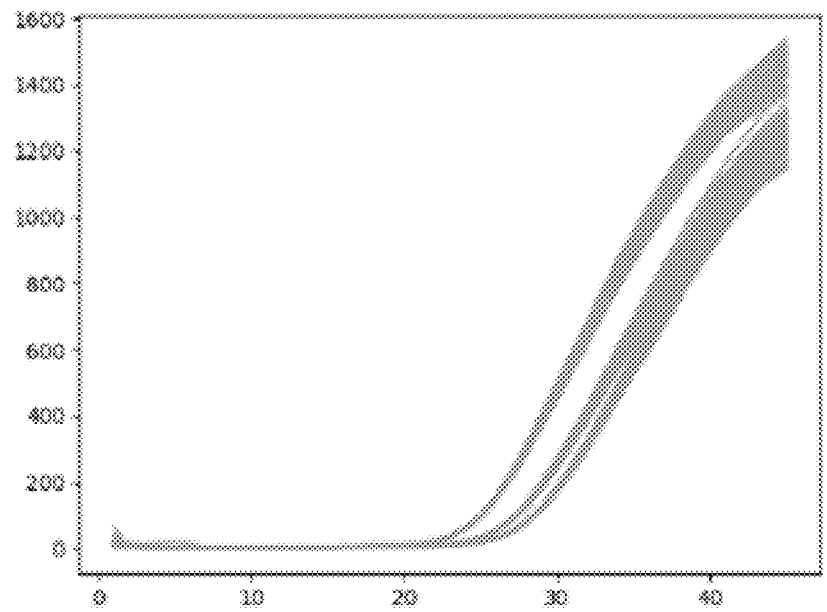
FIG. 22A shows experimental data of nucleic acid amplification using a portable analytic device of the present disclosure.
Figure 22B:
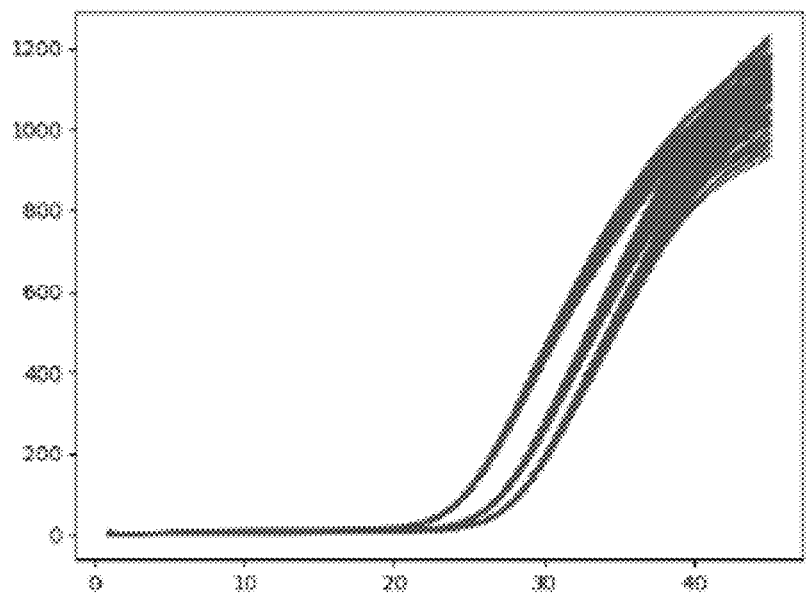
FIG. 22B shows other experimental data of nucleic acid amplification using the portable analytic device.
Figure 22C:
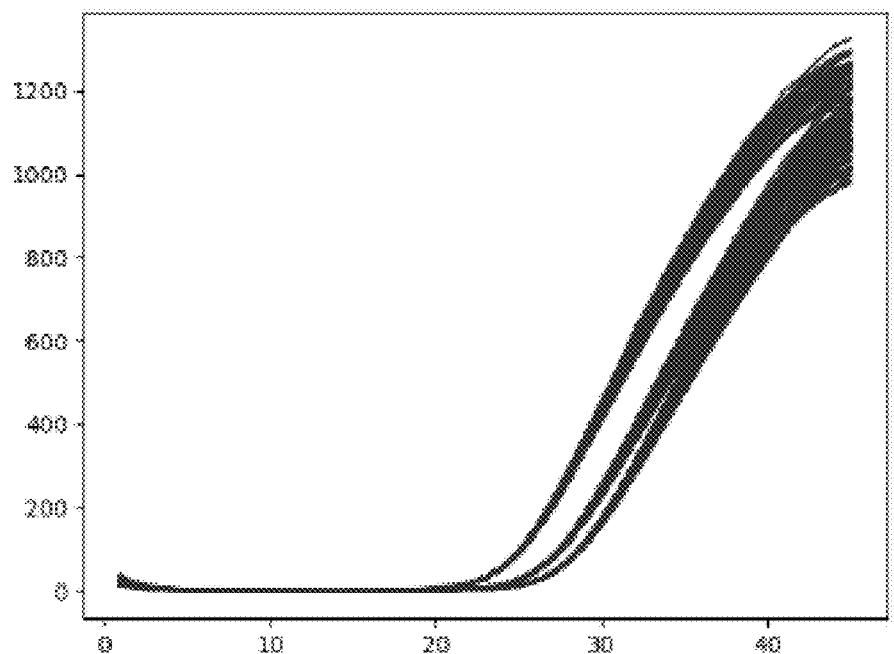
FIG. 22C shows other experimental data of nucleic acid amplification using the portable analytic device, FIG. 221) shows a Cq v. LogSQ plot of the experimental data from FIGS. 22A-C.
Figure 22D:
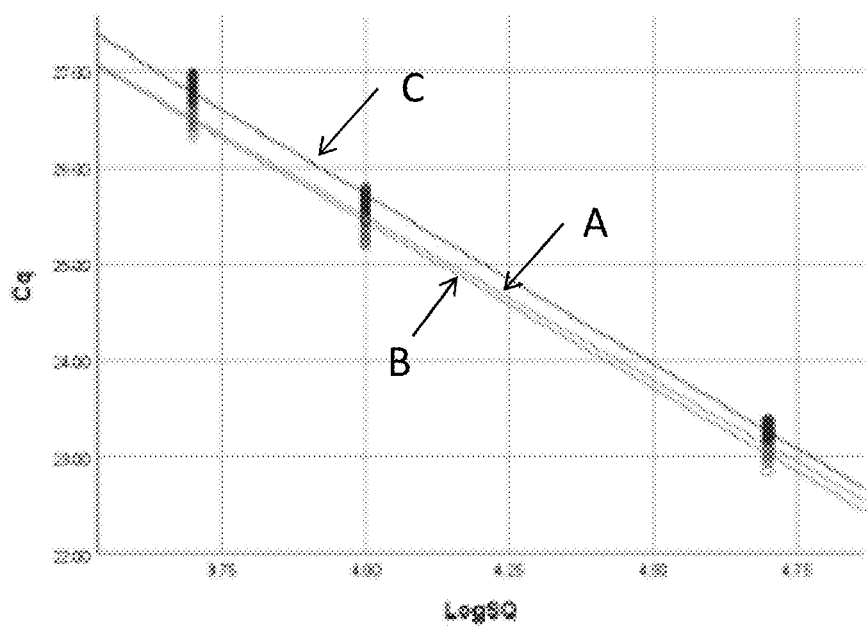

FIGS. 22A-D show example nucleic acid amplification data obtained using the portable analytic device described herein. FIG. 22A shows amplification plot on the portable analytic device described herein from multiplexed reactions using a synthetic DNA target at 50,000, 10,000 and 5,000 copies/reaction using Texas Red-X. FIG. 22B shows amplification plot on the portable analytic device described herein from multiplexed reactions using a synthetic DNA target at 50,000, 10,000 and 5,000 copies/reaction using FAM. FIG. 22C shows amplification plot on the portable analytic device described herein from multiplexed reactions using a synthetic DNA target at 50,000, 10,000 and 5,000 copies/reaction using ATTO647n. All nine wells in the system were run with each concentration 4 times, for a total n=36 per concentration (n=108 per fluorophore). FIG. 22D shows Linear Regression Curve of Cq vs. Log(SQ)(Sq=Starting Quantity) with synthetic DNA target at 50,000, 10,000 and 5,000 copies/reaction [n=36 per concentration (4 runs×9 wells per concentration), n=108 per fluorophore]. The curve A shows a plot using the data obtained in FIG. 22A ($R^2$=0.995). The curve B shows a plot using the data obtained in FIG. 22B ($R^2$=0.996). The curve C shows a plot using the data obtained in FIG. 22C($R^2$=0.996).

Computer Systems

Figure 11:
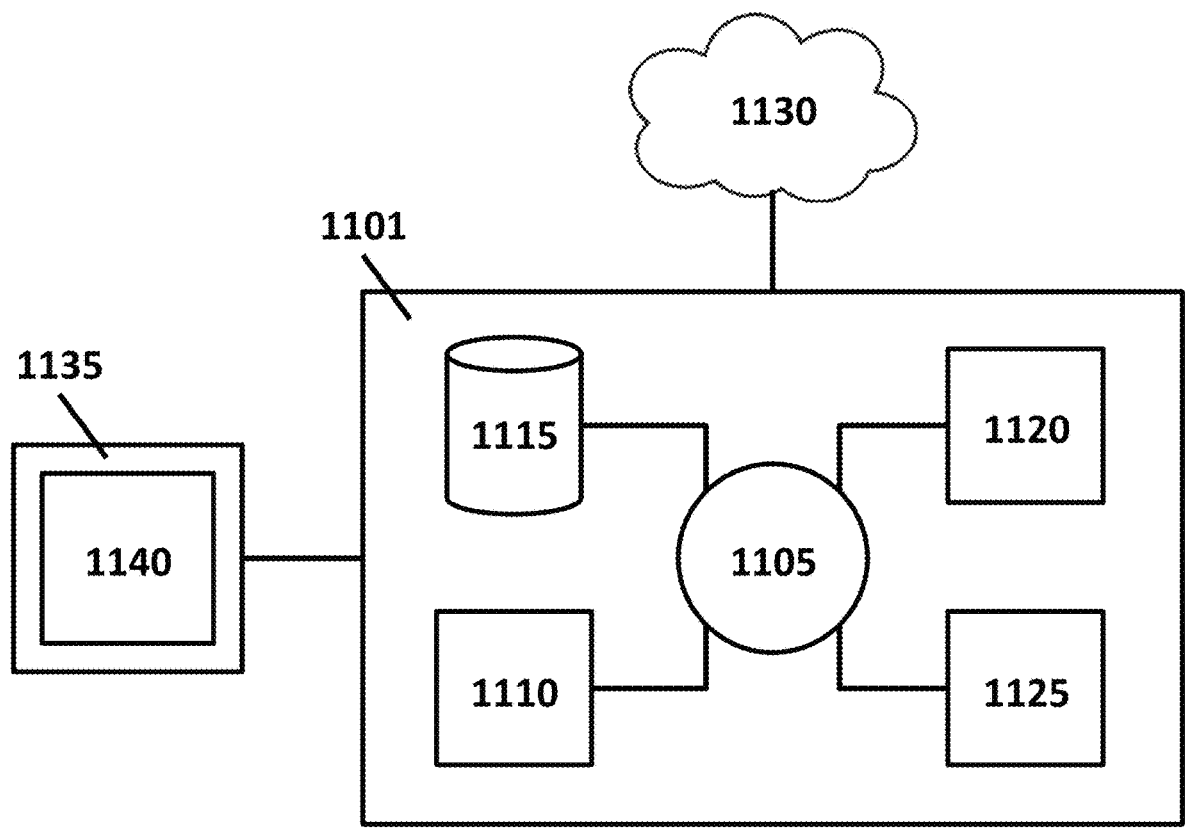
FIG. 11 shows a computer system that is programmed or otherwise configured to implement methods provided herein.

The present disclosure provides computer systems that are programmed to implement methods of the disclosure. FIG. 11 shows a computer system 1101 that is programmed or otherwise configured to analyze a sample. The computer system 1101 may regulate some aspects of the analytic device of the present disclosure, such as, for example, movement of a moving carriage, heating or cooling of a block, and/or activation/deactivation of an excitation source or detector. The computer system may control of the temperature of a block (e.g., through activation of a resistive heater or fan). The computer system 1101 may be integrated into the analytic device of the present disclosure and/or include an electronic device of a user or a computer system that is remotely located with respect to the electronic device. The electronic device may be a mobile electronic device.

The computer system 1101 includes a central processing unit (CPU, also "processor" and "computer processor" herein) 1105, which may be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 may be a data storage unit (or data repository) for storing data. The computer system 1101 may be operatively coupled to a computer network ("network") 1130 with the aid of the communication interface 1120. The network 1130 may be the Internet, an internet and/or extranet, or an intranet and/or extranet that is in communication with the Internet. The network 1130 in some cases is a telecommunication and/or data network. The network 1130 may include one or more computer servers, which may enable distributed computing, such as cloud computing. The network 1130, in some cases with the aid of the computer system 1101, may implement a peer-to-peer network, which may enable devices coupled to the computer system 1101 to behave as a client or a server.

The CPU 1105 may execute a sequence of machine-readable instructions, which may be embodied in a program or software. The instructions may be stored in a memory location, such as the memory 1110. The instructions may be directed to the CPU 1105, which may subsequently program or otherwise configure the CPU 1105 to implement methods of the present disclosure. Examples of operations performed by the CPU 1105 may include fetch, decode, execute, and writeback.

The CPU 1105 may be part of a circuit, such as an integrated circuit. One or more other components of the system 1101 may be included in the circuit. In some cases, the circuit is an application specific integrated circuit (ASIC).

The storage unit 1115 may store files, such as drivers, libraries and saved programs. The storage unit 1115 may store user data, e.g., user preferences and user programs. The computer system 1101 in some cases may include one or more additional data storage units that are external to the computer system 1101, such as located on a remote server that is in communication with the computer system 1101 through an intranet or the Internet.

The computer system 1101 may communicate with one or more remote computer systems through the network 1130. For instance, the computer system 1101 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 1101 via the network 1130.

Methods as described herein may be implemented by way of machine (e.g., computer processor) executable code stored on an electronic storage location of the computer system 1101, such as, for example, on the memory 1110 or electronic storage unit 1115. The machine executable or machine readable code may be provided in the form of software. During use, the code may be executed by the processor 1105. In some cases, the code may be retrieved from the storage unit 1115 and stored on the memory 1110 for ready access by the processor 1105. In some situations, the electronic storage unit 1115 may be precluded, and machine-executable instructions are stored on memory 1110.

The code may be pre-compiled and configured for use with a machine having a processor adapted to execute the code, or may be compiled during runtime. The code may be supplied in a programming language that may be selected to enable the code to execute in a pre-compiled or as-compiled fashion.

Aspects of the systems and methods provided herein, such as the computer system 1101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 may include or be in communication with an electronic display 1135 (UI) 1140 for providing, for example, a current stage of processing of a sample (e.g., a particular step, such as a lysis step, that is being performed). Examples of UI's include, without limitation, a graphical user interface (GUI) and web-based user interface.

Methods and systems of the present disclosure may be implemented byway of one or more algorithms. An algorithm may be implemented by way of software upon execution by the central processing unit 1105.

Methods and systems of the present disclosure may be combined with or modified by other methods or systems, such as, for example, those described in U.S. Pat. No. 9,579,655, which is entirely incorporated herein by reference.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, or within 2-fold, of a value. Where particular values are described in the application and claims, unless otherwise stated the term "about" meaning within an acceptable error range for the particular value may be assumed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A portable analytic device for processing a biological sample, comprising:
   a housing;
   at least one block within said housing, wherein said at least one block comprises a recess configured to contain an assay tube comprising said biological sample and a magnetic bead;
   an excitation filter and an emission filter, wherein said excitation filter and said emission filter are in optical communication with at least a portion of said recess;
   an excitation source configured to provide excitation energy to said biological sample when said assay tube is contained within said recess;
   a detector configured to receive emission energy from said biological sample when the assay tube is contained within said recess; and
   a movable carriage comprising a bar within said housing, wherein said bar comprises a magnet, and wherein said movable carriage is configured to translate such that said magnet and said assay tube move relative to one another, to thereby subject said magnetic bead to motion within said assay tube,
   wherein said portable analytic device has a weight of at most 15 kilograms.

2. The portable analytic device of claim 1, wherein said portable analytic device has a weight of at most 10 kilograms.

3. The portable analytic device of claim 2, wherein said portable analytic device has a weight of at most 5 kilograms.

4. The portable analytic device of claim 1, wherein said housing has a volume that is less than about 1,500 cubic centimeters.

5. The portable analytic device of claim 1, wherein said movable carriage or said at least one block is configured to undergo linear motion.

6. The portable analytic device of claim 5, wherein said movable carriage is configured to undergo linear motion.

7. The portable analytic device of claim 5, wherein said at least one block is configured to undergo linear motion.

8. The portable analytic device of claim 1, wherein said movable carriage is configured to undergo motion while said at least one block is stationary.

9. The portable analytic device of claim 1, wherein said at least one block is configured to undergo motion.

10. The portable analytic device of claim 9, wherein said at least one block is configured to undergo motion while said movable carriage is stationary.

11. The portable analytic device of claim 1, wherein said movable carriage and said at least one block are configured to undergo motion.

12. The portable analytic device of claim 1, wherein said bar comprises a plurality of magnets, which plurality of magnets comprises said magnet.

13. The portable analytic device of claim 1, wherein said magnet is a permanent magnet.

14. The portable analytic device of claim 1, wherein said magnet is an electromagnet.

15. The portable analytic device of claim 1, further comprising at least one heating unit in thermal communication with said at least one block, wherein said at least one heating unit is configured to provide thermal energy to said assay tube through said at least one block.

16. The portable analytic device of claim 1, further comprising at least one cooling unit in thermal communication with said at least one block, wherein said cooling unit is configured to permit removal of thermal energy from said assay tube through said at least one block.

17. The portable analytic device of claim 16, wherein said cooling unit is configured to permit removal of said thermal energy using positive pressure that directs a fluid comprising at least a portion of said thermal energy away from said at least one block.

18. The portable analytic device of claim 1, wherein said movable carriage comprises an optical filter, wherein said movable carriage is configured to translate to bring said optical filter in optical communication with said excitation filter or said emission filter.

19. The portable analytic device of claim 1, further comprising a power supply within said housing, wherein said power supply is configured to provide power to an actuator coupled to said movable carriage or said at least one block, which actuator, upon receiving power from said power supply, is configured to subject said movable carriage or said at least one block to motion such that said movable carriage and said at least one block move relative to one another.

20. A method for processing a biological sample, comprising:
  (a) providing a portable analytic device comprising (i) a housing, (ii) at least one block within said housing, wherein said at least one block comprises a recess that contains an assay tube comprising said biological sample and a magnetic bead, (iii) an excitation filter and an emission filter, wherein said excitation filter and said emission filter are in optical communication with at least a portion of said recess, (iv) an excitation source configured to provide excitation energy to said biological sample, (v) a detector configured to receive emission energy from said biological sample, and (vi) a movable carriage comprising a bar within said housing, wherein said bar comprises a magnet; and wherein said portable analytic device has a weight of at most 15 kilograms; and
  (b) subjecting said movable carriage or said at least one block to motion such that said magnet and said assay tube move relative to one another, thereby subjecting said magnetic bead to motion within said assay tube.

21. The method of claim 20, wherein said movable carriage or said at least one block undergoes linear motion.

22. The method of claim 20, wherein said movable carriage and said at least one block undergo motion.

* * * * *